(12) United States Patent
Hayashi et al.

(10) Patent No.: US 10,693,078 B2
(45) Date of Patent: Jun. 23, 2020

(54) ORGANIC ELECTROLUMINESCENT DEVICE

(71) Applicants: HODOGAYA CHEMICAL CO., LTD., Tokyo (JP); SFC CO., LTD., Cheongju-si (KR)

(72) Inventors: Shuichi Hayashi, Tokyo (JP); Daizou Kanda, Tokyo (JP); Soon-Wook Cha, Cheongju-si (KR); Sang-Woo Park, Cheongju-si (KR); Ju-Man Song, Cheongju-si (KR); Kyung-Seok Jeon, Cheongju-si (KR)

(73) Assignees: Hodogaya Chemical Co., Ltd., Tokyo (JP); SFC Co., Ltd., Cheongju-Si (KR)

( * ) Notice: Subject to any disclaimer, the term of this patent is extended or adjusted under 35 U.S.C. 154(b) by 385 days.

(21) Appl. No.: 15/328,566

(22) PCT Filed: Jul. 16, 2015

(86) PCT No.: PCT/JP2015/003596
§ 371 (c)(1),
(2) Date: Jan. 24, 2017

(87) PCT Pub. No.: WO2016/013184
PCT Pub. Date: Jan. 28, 2016

(65) Prior Publication Data
US 2017/0207395 A1 Jul. 20, 2017

(30) Foreign Application Priority Data
Jul. 25, 2014 (JP) .................................. 2014-151402

(51) Int. Cl.
*H01L 51/00* (2006.01)
*C07D 493/10* (2006.01)
(Continued)

(52) U.S. Cl.
CPC ........ *H01L 51/0059* (2013.01); *C07C 211/54* (2013.01); *C07C 211/58* (2013.01);
(Continued)

(58) Field of Classification Search
CPC ............... H01L 51/0059; H01L 51/006; H01L 51/0061; H01L 51/0072; H01L 51/0094; H01L 51/0052; H01L 51/0074; H01L 51/5064; H01L 51/5016; H01L 51/5056; H01L 51/0071; H01L 51/5012; H01L 51/0056; H01L 51/0058; H01L 51/5072; H01L 51/0073; C07D 307/77; C07D 209/96; C07D 495/10; C07D 493/10;
(Continued)

(56) References Cited

U.S. PATENT DOCUMENTS 6,344,283 B1 * 2/2002 Inoue ..................... C09K 11/06
                                                                 313/504
8,932,735 B2   1/2015 Mizuki et al.
(Continued)

FOREIGN PATENT DOCUMENTS

CN    102414164 A    4/2012
CN    102473856 A    5/2012

OTHER PUBLICATIONS

Office Action dated Feb. 24, 2018, issued for the corresponding Chinese Patent Application No. 201580051993.8 and Japanese translation thereof.

*Primary Examiner* — Alexander C Kollias
(74) *Attorney, Agent, or Firm* — Locke Lord LLP; James E. Armstrong, IV; Nicholas J. DiCeglie, Jr.

(57) ABSTRACT

An organic electroluminescent device having high efficiency, low driving voltage and a long lifetime is provided by combining various materials for an organic electroluminescent device, which are excellent, as materials for an organic electroluminescent device having high efficiency and high durability, in hole and electron injection/transport performances, electron blocking ability, stability in a thin-film state and durability, so as to allow the respective materials to effectively reveal their characteristics. In the organic electroluminescent device having at least an anode, a hole transport layer, a light emitting layer, an electron transport layer and a cathode in this order, the hole transport layer includes an arylamine compound represented by the following general formula (1), and the light emitting layer comprises an amine derivative of the following general formula (2) having a condensed ring structure.

[Chemical Formula 1]

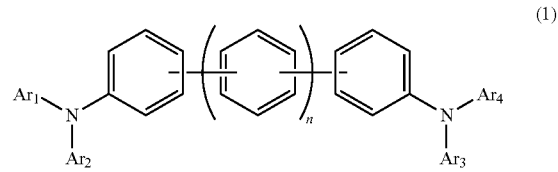

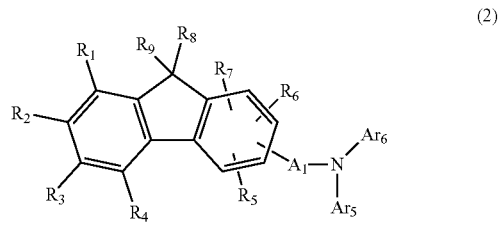

20 Claims, 1 Drawing Sheet

(51) Int. Cl.
| | |
|---|---|
| *C07D 495/10* | (2006.01) |
| *C07D 209/96* | (2006.01) |
| *C07D 307/91* | (2006.01) |
| *C09K 11/06* | (2006.01) |
| *C07D 307/94* | (2006.01) |
| *C07C 211/54* | (2006.01) |
| *C07C 211/58* | (2006.01) |
| *C07C 211/61* | (2006.01) |
| *C07D 307/77* | (2006.01) |
| *C07F 7/08* | (2006.01) |
| *C09K 11/02* | (2006.01) |
| *H01L 51/50* | (2006.01) |

(52) U.S. Cl.
CPC .......... *C07C 211/61* (2013.01); *C07D 209/96* (2013.01); *C07D 307/77* (2013.01); *C07D 307/91* (2013.01); *C07D 307/94* (2013.01); *C07D 493/10* (2013.01); *C07D 495/10* (2013.01); *C07F 7/0812* (2013.01); *C09K 11/025* (2013.01); *C09K 11/06* (2013.01); *H01L 51/006* (2013.01); *H01L 51/0052* (2013.01); *H01L 51/0061* (2013.01); *H01L 51/0072* (2013.01); *H01L 51/0094* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/1096* (2013.01); *H01L 51/0056* (2013.01); *H01L 51/0058* (2013.01); *H01L 51/0071* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5064* (2013.01); *H01L 51/5072* (2013.01)

(58) Field of Classification Search
CPC ... C07D 307/94; C07D 307/91; C07C 211/54; C07C 211/61; C07C 211/58; C07F 7/0812; C09K 11/06; C09K 2211/1014; C09K 2211/1029; C09K 2211/1088; C09K 2211/1092; C09K 2211/1096; C09K 11/025; C09K 2211/1007; C09K 2211/1011
See application file for complete search history.

(56) References Cited

U.S. PATENT DOCUMENTS

| | | | |
|---|---|---|---|
| 2006/0035109 A1* | 2/2006 | Arakane | C09K 11/06 428/690 |
| 2008/0014464 A1* | 1/2008 | Kawamura | C09K 11/06 428/690 |
| 2012/0043533 A1* | 2/2012 | Mizuki | C07C 211/56 257/40 |
| 2012/0181922 A1 | 7/2012 | Kawamura et al. | |
| 2012/0228598 A1* | 9/2012 | Yokoyama | C07D 471/04 257/40 |
| 2013/0032764 A1* | 2/2013 | Buesing | C07D 239/26 252/500 |

* cited by examiner

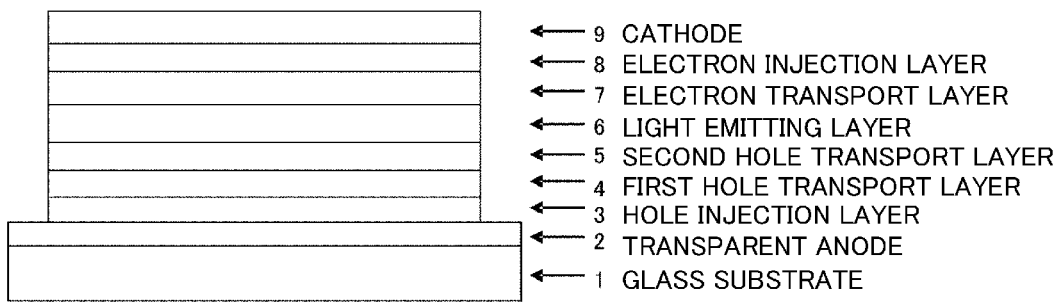

ORGANIC ELECTROLUMINESCENT DEVICE

TECHNICAL FIELD

The present invention relates to an organic electroluminescent device which is a preferred self-luminous device for various display devices. Specifically, this invention relates to organic electroluminescent devices (hereinafter referred to as organic EL devices) using specific arylamine compounds and specific amine derivatives having a condensed ring structure (and specific compounds having an anthracene ring structure).

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to Patent Documents 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to Non-Patent Document 1, for example).

Further, there have been attempts to use triplet excitons for further improvements of luminous efficiency, and the use of a phosphorescence-emitting compound has been examined (refer to Non-Patent Document 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to Non-Patent Document 3, for example).

The light emitting layer can be also fabricated by doping a charge-transporting compound generally called a host material, with a fluorescent compound, a phosphorescence-emitting compound, or a delayed fluorescent-emitting material. As described in the Non-Patent Document, the selection of organic materials in an organic EL device greatly influences various device characteristics such as efficiency and durability (refer to Non-Patent Document 2, for example).

In an organic EL device, charges injected from both electrodes recombine in a light emitting layer to cause emission. What is important here is how efficiently the hole and electron charges are transferred to the light emitting layer in order to form a device having excellent carrier balance. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di($\alpha$-naphthyl)benzidine (NPD) and various aromatic amine derivatives are known as the hole transport materials used for the organic EL device (refer to Patent Documents 1 and 2, for example). Although NPD has desirable hole transportability, its glass transition point (Tg), which is an index of heat resistance, is as low as 96° C., which causes the degradation of device characteristics by crystallization under a high-temperature condition (refer to Non-Patent Document 4, for example). The aromatic amine derivatives described in the Patent Documents include a compound known to have an excellent hole mobility of 10$^{-3}$ cm$^2$/Vs or higher (refer to Patent Documents 1 and 2, for example). However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency. Although an aromatic amine derivative having high durability is reported (refer to Patent Document 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as heat resistance and hole injectability (refer to Patent Documents 4 and 5, for example). However, while the devices using these compounds for the hole injection layer or the hole transport layer have been improved in heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport performances, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport performances, stability as a thin film and durability.

CITATION LIST

Patent Documents

Patent Document 1: JP-A-8-048656
Patent Document 2: Japanese Patent No. 3194657
Patent Document 3: Japanese Patent No. 4943840
Patent Document 4: JP-A-2006-151979
Patent Document 5: WO2008/62636
Patent Document 6: WO2011/059000
Patent Document 7: WO2003/060956
Patent Document 8: KR-A-2013-060157
Patent Document 9: JP-A-7-126615
Patent Document 10: JP-A-8-048656
Patent Document 11: JP-A-2005-108804

Non-Patent Documents

Non-Patent Document 1: The Japan Society of Applied Physics, 9th Lecture Preprints, pp. 55 to 61 (2001)
Non-Patent Document 2: The Japan Society of Applied Physics, 9th Lecture Preprints, pp. 23 to 31 (2001)
Non-Patent Document 3: Appl. Phys. Let., 98, 083302 (2011)
Non-Patent Document 4: Organic EL Symposium, the 3rd Regular presentation Preprints, pp. 13 to 14 (2006)

SUMMARY OF THE INVENTION

Problems to be Solved by the Invention

An object of the present invention is to provide an organic EL device having high efficiency, low driving voltage and a long lifetime, by combining various materials for an organic EL device, which are excellent, as materials for an organic EL device having high efficiency and high durability, in hole and electron injection/transport performances, electron blocking ability, stability in a thin-film state and durability, so as to allow the respective materials to effectively reveal their characteristics.

Physical properties of the organic EL device to be provided by the present invention include (1) high luminous efficiency and high power efficiency, (2) low turn on voltage, (3) low actual driving voltage, and (4) a long lifetime.

Means for Solving the Problems

To achieve the above object, the present inventors have noted that an arylamine material is excellent in hole injection and transport abilities, stability as a thin film and durability, specific amine derivatives having a condensed ring structure is excellent in luminous efficiency, and that a compound having an anthracene ring structure is excellent in electron injection/transport performances, stability as a thin film and durability. They have selected specific arylamine compounds and amine derivatives having specific structures and having a condensed ring structure such that holes can be efficiently injected and transported into a light emitting layer, and have produced various organic EL devices by combining a hole transport material and a light-emitting material in good carrier balance that matching characteristics of the light-emitting material. Then, they have intensively conducted characteristic evaluations of the devices. Also, they have selected specific compounds having an anthracene ring structure to improve electron injection/transport efficiency to the light emitting layer, and have produced various organic EL devices by combining a hole transport material, a light-emitting material, and an electron transport material in good carrier balance that more matching characteristics of the light-emitting material. Then, they have intensively conducted characteristic evaluations of the devices. Further, they have formed a hole transport layer having a two-layer structure of a first hole transport layer and a second hole transport layer, and have selected two specific kinds of arylamine compounds. And, they have selected a material of a first hole transport layer such that holes can be efficiently injected and transported into a light emitting layer, and have selected a material of a second hole transport layer that excels in electron blocking performance. They have produced various organic EL devices that maintain carrier balance by refining combinations of those. Then, they have intensively conducted characteristic evaluations of the devices. As a result, they have completed the present invention.

Specifically, according to the present invention, the following organic EL devices are provided.

1) An organic electroluminescent device comprising at least an anode, a hole transport layer, a light emitting layer, an electron transport layer and a cathode in this order, wherein the hole transport layer comprises an arylamine compound of the following general formula (1), and the light emitting layer comprises an amine derivative of the following general formula (2) having a condensed ring structure.

[Chemical Formula 1]

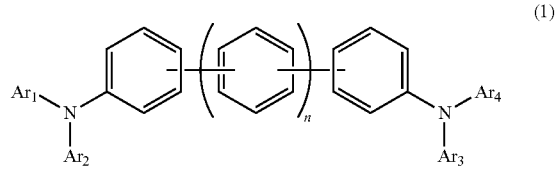

(1)

In the formula, $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group. n represents an integer of 2 to 4.

[Chemical Formula 2]

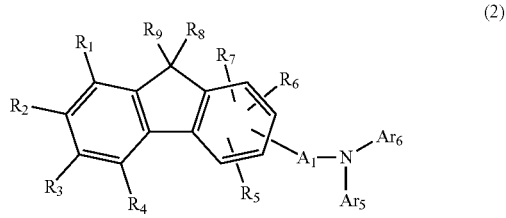

(2)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_5$ and $Ar_6$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_5$ and $Ar_6$ may bind to each other via a single bond, substituted or unsubstituted methylene, an oxygen atom, or a sulfur atom to form a ring. $R_1$ to $R_4$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R_1$ to $R_4$ may bind to each other via a single bond, substituted or unsubstituted methylene, an oxygen atom, or a sulfur atom to form a ring, and $R_1$ to $R_4$ and the benzene ring binding with $R_1$ to $R_4$ may bind to each other via substituted or unsubstituted methylene, an oxygen atom, a sulfur atom, or a mono-substituted amino group. $R_5$ to $R_7$ may be the same or different, represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_5$ to $R_7$ may bind to each other via a single bond, substituted or unsubstituted methylene, an oxygen atom, or a sulfur atom to form a ring, and $R_5$ to $R_7$ and the benzene ring binding with $R_5$ to $R_7$ may bind to each other via substituted or unsubstituted methylene, an oxygen atom, a sulfur atom, or a mono-substituted amino group. $R_8$ and $R_9$ may be the same or different, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_8$ and $R_9$ may bind to each other via a single bond, substituted or unsubstituted methylene, an oxygen atom, a sulfur atom, or a mono-substituted amino group to form a ring.

2) The organic EL device of 1), wherein the electron transport layer comprises a compound of the following general formula (3) having an anthracene ring structure.

[Chemical Formula 3]

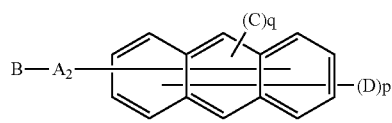
(3)

In the formula, $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. B represents a substituted or unsubstituted aromatic heterocyclic group. C represents a substituted or unsubstituted aromatic hydrocarbon group, a substituted or unsubstituted aromatic heterocyclic group, or a substituted or unsubstituted condensed polycyclic aromatic group. D may be the same or different, and represents a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group. p represents 7 or 8, and q represents 1 or 2 while maintaining a relationship that a sum of p and q is 9.

3) The organic EL device of 2), wherein the compound having an anthracene ring structure is a compound of the following general formula (3a) having an anthracene ring structure.

[Chemical Formula 4]

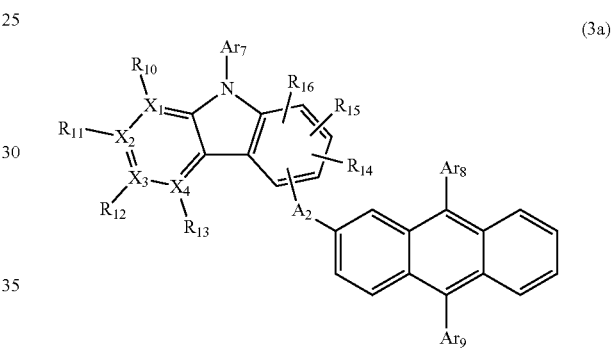
(3a)

In the formula, $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_7$, $Ar_8$, and $Ar_9$ may be the same or different, and represent a substituted or unsubstituted aromatic hydrocarbon group, a substituted or unsubstituted aromatic heterocyclic group, or a substituted or unsubstituted condensed polycyclic aromatic group. $R_{10}$ to $R_{16}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_{10}$ to $R_{16}$ may bind to each other via a single bond, substituted or unsubstituted methylene, an oxygen atom, or a sulfur atom to form a ring. $X_1$, $X_2$, $X_3$, and $X_4$ represent a carbon atom or a nitrogen atom, where only one of $X_1$, $X_2$, $X_3$, and $X_4$ is a nitrogen atom, and the nitrogen atom in this case does not have the hydrogen atom or the substituent for $R_{10}$ to $R_{13}$.

4) The organic EL device of 2), wherein the compound having an anthracene ring structure is a compound of the following general formula (3b) having an anthracene ring structure.

[Chemical Formula 5]

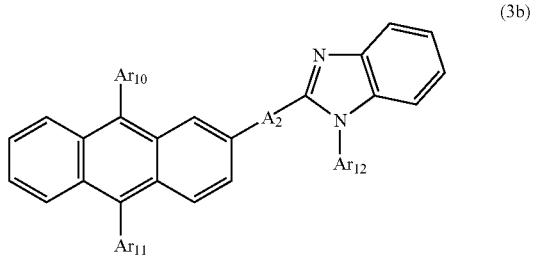

(3b)

In the formula, $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{10}$, $Ar_{11}$, and $Ar_{12}$ may be the same or different, and represent a substituted or unsubstituted aromatic hydrocarbon group, a substituted or unsubstituted aromatic heterocyclic group, or a substituted or unsubstituted condensed polycyclic aromatic group.

5) The organic EL device of 2), wherein the compound having an anthracene ring structure is a compound of the following general formula (3c) having an anthracene ring structure.

[Chemical Formula 6]

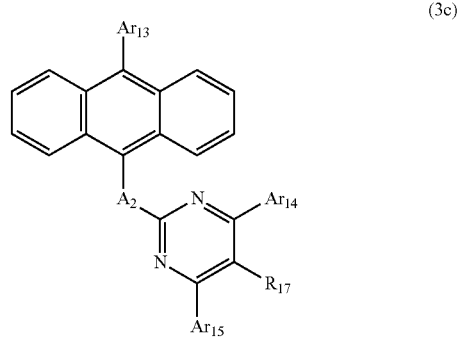

(3c)

In the formula, $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{13}$, $Ar_{14}$, and $Ar_{15}$ may be the same or different, and represent a substituted or unsubstituted aromatic hydrocarbon group, a substituted or unsubstituted aromatic heterocyclic group, or a substituted or unsubstituted condensed polycyclic aromatic group. $R_{17}$ represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy.

6) The organic EL device of any one of 1) to 5), wherein the hole transport layer has a two-layer structure of a first hole transport layer and a second hole transport layer, and the second hole transport layer comprises the arylamine compound of the general formula (1).

7) The organic EL device of any one of 1) to 6), wherein the light emitting layer comprises an anthracene derivative.

8) The organic EL device of 7), wherein the light emitting layer comprises a host material that is an anthracene derivative.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Specific examples of the "substituent" in the "substituted aromatic hydrocarbon group", the "substituted aromatic heterocyclic group", or the "substituted condensed polycyclic aromatic group" represented by $Ar_1$ to $Ar_4$ in the general formula (1) include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl; arylvinyls such as styryl and naphthylvinyl; acyl such as acetyl, and benzoyl; silyl such as trimethylsilyl and triphenylsilyl. These substituents may be further substituted with the exemplified substituents above. These substituents may bind to each other via a single bond, substituted or unsubstituted methylene, an oxygen atom, or a sulfur atom to form a ring.

Specific examples of the "aromatic hydrocarbon", the "aromatic heterocyclic ring", or the "condensed polycyclic aromatics" of the "substituted or unsubstituted aromatic hydrocarbon", the "substituted or unsubstituted aromatic heterocyclic ring", or the "substituted or unsubstituted condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_1$ in the general formula (2) include benzene, biphenyl, terphenyl, tetrakisphenyl, styrene, naphthalene, anthracene, acenaphthalene, fluorene, phenanthrene, indane, pyrene, triphenylen, pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

The "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_1$ in the general formula (2) is a divalent group that results from the removal of two hydrogen atoms from the above "aromatic hydrocarbon", "aromatic heterocyclic ring", or "condensed polycyclic aromatics".

These divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_5$ and $Ar_6$ in the general formula (2) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ to $R_7$ in the general formula (2) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring. These groups ($R_1$ to $R_7$) and the benzene ring directly binding with these groups ($R_1$ to $R_7$) may bind to each other via a linking group such as substituted or unsubstituted methylene, an oxygen atom, a sulfur atom, or a monosubstituted amino group to form a ring.

Specific examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_1$ to $R_7$ in the general formula (2) include a deuterium atom; cyano; nitro; halogen atoms such as a fluorine atom, a chlorine atom, a bromine atom, and an iodine atom; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl; disubstituted amino groups substituted with an aromatic hydrocarbon group or a condensed polycyclic aromatic group, such as diphenylamino, and dinaphthylamino; disubstituted amino groups substituted with an aromatic heterocyclic group, such as dipyridylamino, and dithienylamino; and disubstituted amino groups substituted with a substituent selected from an aromatic hydrocarbon group, a condensed polycyclic aromatic group, or an aromatic heterocyclic group. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_7$ in the general formula (2) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring. These groups ($R_1$ to $R_7$) and the benzene ring directly binding with these groups ($R_1$ to $R_7$) may bind to each other via a linking group such as substituted or unsubstituted methylene, an oxygen atom, a sulfur atom, or a monosubstituted amino group to form a ring.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_1$ to $R_7$ in the general formula (2), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_7$ in the general formula (2) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring. These groups ($R_1$ to $R_7$) and the benzene ring directly binding with these groups ($R_1$ to $R_7$) may bind to each other via a linking group such as substituted or unsubstituted methylene, an oxygen atom, a sulfur atom, or a mono-substituted amino group to form a ring.

These groups may have a substituent, and specific examples of the substituent include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl; arylvinyls such as styryl and naphthylvinyl; acyl such as acetyl, and benzoyl; silyl such as trimethylsilyl and triphenylsilyl; disubstituted amino groups substituted with an aromatic hydrocarbon group or a condensed polycyclic aromatic group, such as diphenylamino and dinaphthylamino; disubstituted amino groups substituted with an aromatic heterocyclic group, such as dipyridylamino, and dithienylamino; and disubstituted amino groups substituted with a substituent selected from an aromatic hydrocarbon group, a condensed polycyclic aromatic group, or an aromatic heterocyclic group. These substituents may be further substituted with the exemplified substituents above. These substituents may bind to each other via a single bond, substituted or unsubstituted methylene, an oxygen atom, or a sulfur atom to form a ring.

Specific examples of the "aryloxy" in the "substituted or unsubstituted aryloxy" represented by $R_1$ to $R_7$ in the general formula (2) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These groups may bind to each other via a single bond, substituted or unsubstituted methylene, an oxygen atom, or a sulfur atom to form a ring. These groups ($R_1$ to $R_7$) and the benzene ring directly binding with these groups ($R_1$ to $R_7$) may bind to each other via a linking group such as substituted or unsubstituted methylene, an oxygen atom, a sulfur atom, or a mono-substituted amino group to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $R_1$ to $R_7$ in the general formula (2), and possible embodiments may also be the same embodiments as the exemplified embodiments.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by $R_1$ to $R_4$ in the general formula (2) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the "disubstituted amino group substituted with a group selected from an aromatic hydrocarbon group, an aromatic heterocyclic group, and a condensed polycyclic aromatic group" represented by $R_1$ to $R_4$ in the general formula (2), these groups ($R_1$ to $R_4$) may bind to each other via the "aromatic hydrocarbon group", the "aromatic heterocyclic group", or the "condensed polycyclic aromatic group" of these groups ($R_1$ to $R_4$), and a single bond, substituted or unsubstituted methylene, an oxygen atom, or a sulfur atom to form a ring. These groups ($R_1$ to $R_4$) and the benzene ring directly binding with these groups ($R_1$ to $R_4$) may bind to each other via the "aromatic hydrocarbon group", the "aromatic heterocyclic group", or the "condensed polycyclic aromatic group" of these groups ($R_1$ to $R_4$), and a linking group such as substituted or unsubstituted methylene, an oxygen atom, a sulfur atom, or a mono-substituted amino group to form a ring.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_8$ and $R_9$ in the general formula (2) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ and $R_7$ in the general formula (2). These groups may bind to each other via a linking group such as a single bond, substituted or unsubstituted methylene, an oxygen atom, a sulfur atom, or a mono-substituted amino group to form a ring.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", the "linear or branched alkenyl of 2 to 6 carbon atoms having a substituent", the "substituted aromatic hydrocarbon group", the "substituted aromatic heterocyclic group", or the "substituted condensed polycyclic aromatic group" represented by $R_1$ to $R_7$ in the general formula (2), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_8$ and $R_9$ in the general formula (2) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a linking group such as a single bond, substituted or unsubstituted methylene, an oxygen atom, a sulfur atom, or a mono-substituted amino group to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $R_1$ to $R_7$ in the general formula (2), and possible embodiments may also be the same embodiments as the exemplified embodiments.

Examples of the "aryloxy" in the "substituted or unsubstituted aryloxy" represented by $R_8$ and $R_9$ in the general formula (2) include the same groups exemplified as the groups for the "aryloxy" in the "substituted or unsubstituted aryloxy" represented by $R_1$ to $R_7$ in the general formula (2). These groups may bind to each other via a linking group such as a single bond, substituted or unsubstituted methylene, an oxygen atom, a sulfur atom, or a mono-substituted amino group to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $R_1$ to $R_7$ in the general formula (2), and possible embodiments may also be the same embodiments as the exemplified embodiments.

Examples of the "substituent" in the "mono-substituted amino group" of the linking group in the general formula (2) include the same substituents exemplified as the "substituent" of the "linear or branched alkyl of 1 to 6 carbon atoms", the "cycloalkyl of 5 to 10 carbon atoms", the "aromatic hydrocarbon group", the "aromatic heterocyclic group", or the "condensed polycyclic aromatic group" in the "linear or branched alkyl of 1 to 6 carbon atoms that may have a substituent", the "cycloalkyl of 5 to 10 carbon atoms that may have a substituent", the "substituted or unsubstituted aromatic hydrocarbon group", the "substituted or unsubstituted aromatic heterocyclic group", or the "substituted or unsubstituted condensed polycyclic aromatic group" represented by $R_1$ to $R_7$ in the general formula (2).

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", the "substituted aromatic hydrocarbon group", the "substituted aromatic heterocyclic group", or the "substituted condensed polycyclic aromatic group" represented by $R_1$ to $R_7$ in the general formula (2), and possible embodiments may also be the same embodiments as the exemplified embodiments.

Examples of the "aromatic hydrocarbon", the "aromatic heterocyclic ring", or the "condensed polycyclic aromatics" of the "substituted or unsubstituted aromatic hydrocarbon", the "substituted or unsubstituted aromatic heterocyclic ring", or the "substituted or unsubstituted condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_2$ in the general formula (3), the general formula (3a), the general formula (3b), and the general formula (3c) include the same compounds exemplified as the compounds for the "aromatic hydrocarbon", the "aromatic heterocyclic ring", or the "condensed polycyclic aromatics" of the "substituted or unsubstituted aromatic hydrocarbon", the "substituted or unsubstituted aromatic heterocyclic ring", or the "substituted or unsubstituted condensed polycyclic aromatics" in the "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_1$ in the general formula (2).

The "divalent group of a substituted or unsubstituted aromatic hydrocarbon", the "divalent group of a substituted or unsubstituted aromatic heterocyclic ring", or the "divalent group of substituted or unsubstituted condensed polycyclic aromatics" represented by $A_2$ in the general formula (3), the general formula (3a), the general formula (3b), and the general formula (3c) is a divalent group that results from the removal of two hydrogen atoms from the above "aromatic hydrocarbon", "aromatic heterocyclic ring", or "condensed polycyclic aromatics".

These divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aromatic heterocyclic group" in the "substituted or unsubstituted aromatic heterocyclic group" represented by B in the general formula (3) include triazinyl, pyridyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Specific examples of the "substituent" in the "substituted aromatic heterocyclic group" represented by B in the general formula (3) include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; cycloalkyls of 5 to 10 carbon atoms such as cyclopentyl, cyclohexyl, 1-adamantyl, and 2-adamantyl; linear or branched alkyloxys of 1 to 6 carbon atoms such as methyloxy, ethyloxy, and propyloxy; cycloalkyloxys of 5 to 10 carbon atoms such as cyclopentyloxy, cyclohexyloxy, 1-adamantyloxy, and 2-adamantyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl; aryloxys such as phenyloxy, biphenylyloxy, naphthyloxy, anthracenyloxy, phenanthrenyloxy; arylvinyls such as styryl and naphthylvinyl; and acyls such as acetyl and benzoyl. These substituents may be further substituted with the exemplified substituents above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by C in the general formula (3) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). When a plurality of these groups bind to the same anthracene ring (when q is 2), these groups may be the same or different.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "linear or branched alkyl of 1 to 6 carbon atoms" represented by D in the general formula (3) include methyl, ethyl, n-propyl, isopropyl, n-butyl, isobutyl, tert-butyl, n-pentyl, isopentyl, neopentyl, and n-hexyl.

The plurality of D may be the same or different, and these groups may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by D in the general formula (3) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). The plurality of D may be the same or different, and these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_7$, $Ar_8$, and $Ar_9$ in the general formula (3a) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{10}$ to $R_{16}$ in the general formula (3a) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a) include a deuterium atom; cyano; nitro; halogen atoms such as a fluorine atom, a chlorine atom, a bromine atom, and an iodine atom; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl. These substituents may be further substituted with the substituents exemplified above. These substituents may bind to each other via a single bond, substituted or unsubstituted methylene, an oxygen atom, or a sulfur atom to form a ring.

Specific examples of the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_{10}$ to $R_{16}$ in the general formula (3a) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{10}$ to $R_{16}$ in the general formula (3a) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aryloxy" in the "substituted or unsubstituted aryloxy" represented by $R_{10}$ to $R_{16}$ in the general formula (3a) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the general formula (3a), $X_1$, $X_2$, $X_3$, and $X_4$ represent a carbon atom or a nitrogen atom, and only one of $X_1$, $X_2$, $X_3$, and $X_4$ is a nitrogen atom. The nitrogen atom in this case does not have the hydrogen atom or the substituent for $R_1$ to $R_4$. That is, $R_{10}$ does not exist when $X_1$ is a nitrogen atom, $R_{11}$ does not exist when $X_2$ is a nitrogen atom, $R_{12}$ does not exist when $X_3$ is a nitrogen atom, and $R_{13}$ does not exist when $X_4$ is a nitrogen atom.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{10}$, $Ar_{11}$, and $Ar_{12}$ in the general formula (3b) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{13}$, $Ar_{14}$, and $Ar_{15}$ in the general formula (3c) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{17}$ in the general formula (3c) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{10}$ to $R_{16}$ in the general formula (3a).

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a).

Examples of the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_{17}$ in the general formula (3c) include the same groups exemplified as the groups for the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_{10}$ to $R_{16}$ in the general formula (3a).

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a).

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{17}$ in the general formula (3c) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aryloxy" in the "substituted or unsubstituted aryloxy" represented by $R_{17}$ in the general formula (3c) include the same groups exemplified as the groups for the "aryloxy" in the "substituted or unsubstituted aryloxy" represented by $R_{10}$ to $R_{16}$ in the general formula (3a).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

$Ar_1$ to $Ar_4$ in the general formula (1) are preferably the "substituted or unsubstituted aromatic hydrocarbon group", the "substituted or unsubstituted oxygen-containing aromatic heterocyclic group", or the "substituted or unsubstituted condensed polycyclic aromatic group", far preferably, phenyl, biphenylyl, terphenylyl, naphthyl, phenanthrenyl, fluorenyl, or dibenzofuranyl.

It is preferable that $Ar_1$ and $Ar_2$, or $Ar_3$ and $Ar_4$ in the general formula (1) be different groups, and it is far preferable that $Ar_1$ and $Ar_2$, and $Ar_3$ and $Ar_4$ in the general formula (1) be different groups.

n in the general formula (1) is preferably 2 or 3. As bonding patterns of phenylene groups in the general formula (1), it is preferable that not all the bonding patterns be 1,4-bonding but the bonding patterns include 1,2-bonding or 1,3-bonding from the viewpoint of thin film stability influencing a device lifetime. As a result, aryldiamine derivatives in which four phenylene groups (when n is 2), five phenylene groups (when n is 3), or six phenylene groups (when n is 4) are bonded, are preferably aryldiamine derivatives in which the phenylene groups are not bonded linearly, such as 1,1':3',1":3",1'''-quaterphenyldiamine, 1,1':3',1":2",1'''':3''', 1''''-quinquephenyldiamine, 1,1':3',1":3",1''':3''',1''''-quinquephenyldiamine, 1,1':2',1":2",1'''-quaterphenyldiamine, 1,1':3',1":3",1'''-quaterphenyldiamine, 1,1':4',1":2",1''':4''', 1''''-quinquephenyldiamine, 1,1':2',1":3",1''':2''',1''''-quinquephenyldiamine, 1,1':4',1":3",1''':4''',1''''-quinquephenyldiamine, and 1,1':2',1":2",1''':2''',1''''-quinquephenyldiamine.

$A_1$ in the general formula (2) is preferably the "divalent group of a substituted or unsubstituted aromatic hydrocarbon" or a single bond, far preferably, a divalent group that results from the removal of two hydrogen atoms from benzene, biphenyl, or naphthalene; or a single bond, particularly preferably a single bond.

$Ar_5$ and $Ar_6$ in the general formula (2) are preferably phenyl, biphenylyl, naphthyl, fluorenyl, indenyl, pyridyl, dibenzofuranyl, pyridobenzofuranyl.

$Ar_5$ and $Ar_6$ in the general formula (2) may directly bind to each other via a single bond, substituted or unsubstituted methylene, an oxygen atom, or a sulfur atom to form a ring, or $Ar_5$ and $Ar_6$ in the general formula (2) may bind to each other via substituents of these groups, and single bond, substituted or unsubstituted methylene, an oxygen atom, or a sulfur atom to form a ring.

At least one of $R_1$ to $R_4$ in the general formula (2) is preferably the "disubstituted amino group substituted with a group selected from an aromatic hydrocarbon group, an aromatic heterocyclic group, and a condensed polycyclic aromatic group"; or the "aromatic hydrocarbon group", the "aromatic heterocyclic group", or the "condensed polycyclic aromatic group" having, as a substituent, the "disubstituted amino group substituted with a group selected from an aromatic hydrocarbon group, an aromatic heterocyclic group, and a condensed polycyclic aromatic group", far preferably, the "disubstituted amino group substituted with a group selected from an aromatic hydrocarbon group, an aromatic heterocyclic group, and a condensed polycyclic aromatic group". In this case, $R_2$ is preferably the "disubstituted amino group substituted with a group selected from an aromatic hydrocarbon group, an aromatic heterocyclic group, and a condensed polycyclic aromatic group", only $R_2$ is far preferably the "disubstituted amino group substituted with a group selected from an aromatic hydrocarbon group, an aromatic heterocyclic group, and a condensed polycyclic aromatic group".

The "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" in this case is preferably phenyl, biphenylyl, naphthyl, fluorenyl, indenyl, pyridyl, dibenzofuranyl, pyridobenzofuranyl.

In the general formula (2), it is preferable that adjacent two groups of $R_1$ to $R_4$ or all groups of $R_1$ to $R_4$ are vinyl, and adjacent two vinyl groups may bind to each other via a single bond to form a condensed ring, that is, to form a naphthalene ring or a phenanthrene ring with the benzene ring binding with $R_1$ to $R_4$.

In the general formula (2), it is preferable that one of $R_1$ to $R_4$ is the "aromatic hydrocarbon group", and the group and the benzene ring binding with $R_1$ to $R_4$ may bind to each other via substituted or unsubstituted methylene, an oxygen atom, or a sulfur atom to form a ring. It is far preferred that the "aromatic hydrocarbon group" in this case is phenyl, and the group and the benzene ring binding with $R_1$ to $R_4$ may bind to each other via an oxygen atom, or a sulfur atom to form a ring, that is, to form a dibenzofuran ring or a dibenzothiophene ring with the benzene ring binding with $R_1$ to $R_4$.

In the general formula (2), it is preferable that one of $R_5$ to $R_7$ is the "aromatic hydrocarbon group", and the group and the benzene ring binding with $R_5$ to $R_7$ may bind to each other via substituted or unsubstituted methylene, an oxygen atom, or a sulfur atom to form a ring. It is far preferred that the "aromatic hydrocarbon group" in this case is phenyl, and the group and the benzene ring binding with $R_5$ to $R_7$ may bind to each other via an oxygen atom, or a sulfur atom to form a ring, that is, to form a dibenzofuran ring or a dibenzothiophene ring.

As described above, among the amine derivatives of the general formula (2) having a condensed ring structure, the embodiments represented by the following general formulas (2a-a), (2a-b), (2b-a), (2b-b), (2b-c), (2b-d), (2c-a), or (2c-b) as the embodiments in which $R_1$ to $R_7$ may bind to each other to form a ring, or $R_1$ to $R_7$ and the benzene ring binding with $R_1$ to $R_7$ may bind to each other to form a ring are preferable.

[Chemical Formula 7]

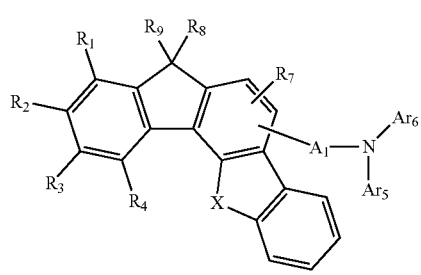

(2a-a)

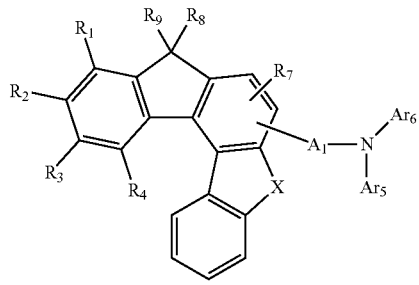

(2a-b)

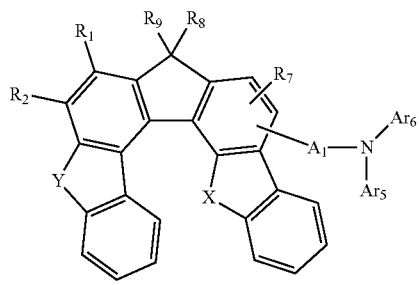

(2b-a)

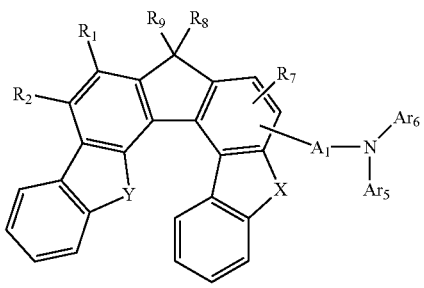

(2b-b)

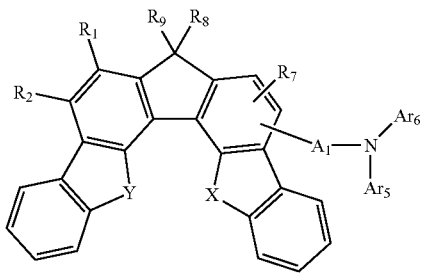

(2b-c)

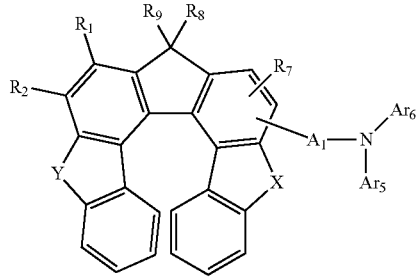

(2b-d)

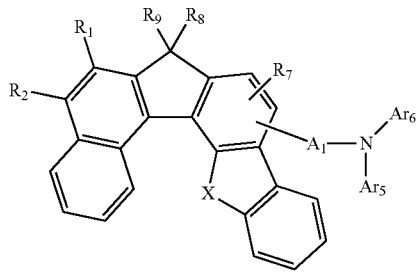
(2c-a)

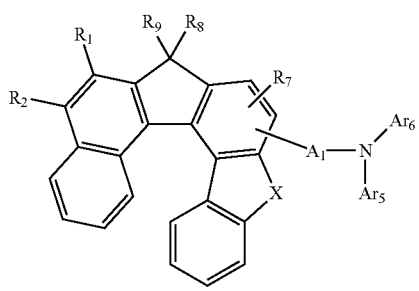
(2c-b)

In the formula, X and Y may be the same or different, each representing an oxygen atom or a sulfur atom. $A_1$, $Ar_5$, $Ar_6$, $R_1$ to $R_4$, $R_7$, $R_8$, and $R_9$ are as defined in the general formula (2).

$R_8$ and $R_9$ in the general formula (2) are preferably the "substituted or unsubstituted aromatic hydrocarbon group", the "substituted or unsubstituted oxygen-containing aromatic heterocyclic group", or the "substituted or unsubstituted condensed polycyclic aromatic group", far preferably, phenyl, naphthyl, phenanthrenyl, pyridyl, quinolyl, isoquinolyl, dibenzofuranyl, particularly preferably phenyl.

Further, it is preferable that $R_8$ and $R_9$ may bind to each other via a linking group such as a single bond, substituted or unsubstituted methylene, an oxygen atom, or a sulfur atom or a mono-substituted amino group to form a ring, and it is far preferred that these groups may bind to each other via a single bond to form a ring.

As described above, among the amine derivatives of the general formula (2) having a condensed ring structure, the embodiments represented by the following general formulas (2a-a1), (2a-b1), (2b-b1), (2b-c1), (2b-d1), (2c-a1), or (2c-b1) as the embodiments in which $R_8$ and $R_9$ may bind to each other to form a ring are preferable.

[Chemical Formula 8]

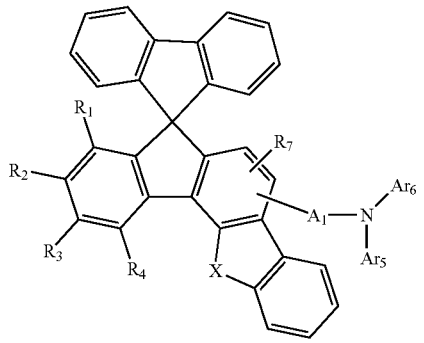
(2a-a1)

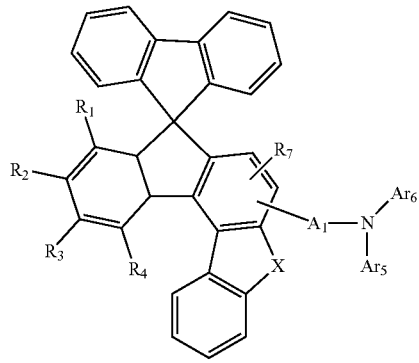
(2a-b1)

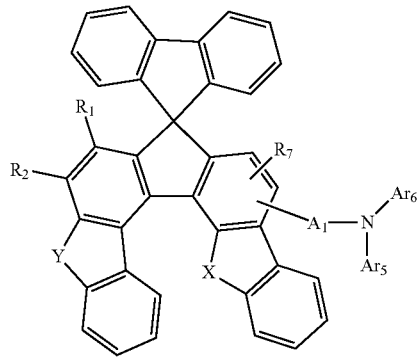
(2b-a1)

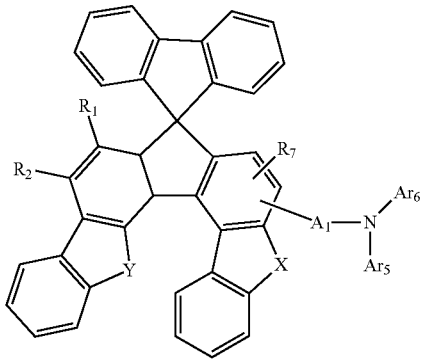
(2b-b1)

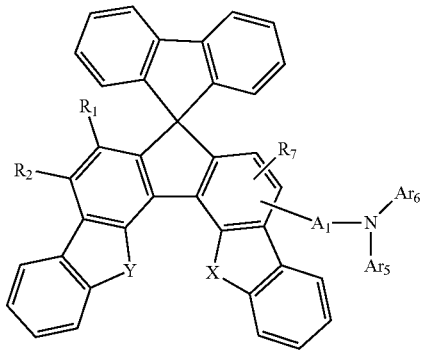
(2b-c1)

-continued

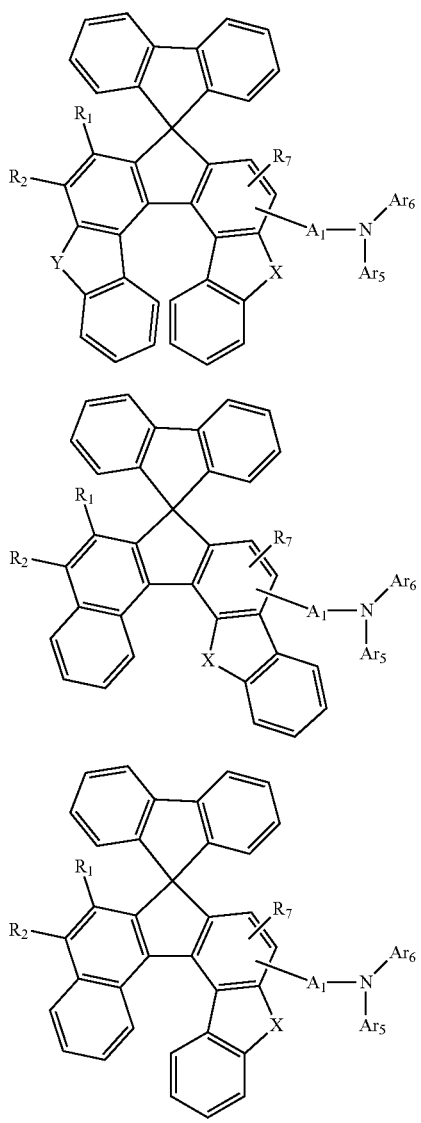

(2b-d1)

(2c-a1)

(2c-b1)

In the formula, X and Y may be the same or different, each representing an oxygen atom or a sulfur atom. $A_1$, $Ar_5$, $Ar_6$, $R_1$ to $R_4$, and $R_7$ are as defined in the general formula (2).

$A_1$ is preferably bonded to the 2-position (or 7-position) of the fluorene ring.

In this case, the amine derivatives of the general formula (2) having a condensed ring structure are represented by the following general formula (2').

[Chemical Formula 9]

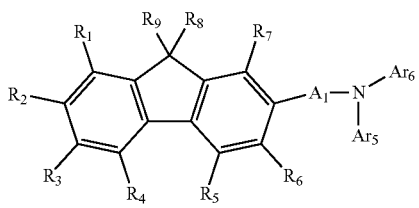

(2')

Examples of the "aromatic heterocyclic group" in the "substituted or unsubstituted aromatic heterocyclic group" represented by B in the general formula (3) is preferably a nitrogen-containing aromatic heterocyclic group such as pyridyl, pyrimidinyl, pyrrolyl, quinolyl, isoquinolyl, indolyl, carbazolyl, benzoxazolyl, benzothiazolyl, quinoxalinyl, benzoimidazolyl, pyrazolyl, or carbolinyl, far preferably, pyridyl, pyrimidinyl, quinolyl, isoquinolyl, indolyl, pyrazolyl, benzoimidazolyl or carbolinyl.

With respect to p and q in the general formula (3), p represents 7 or 8, and q represents 1 or 2 while maintaining a relationship that a sum of p and q (p+q) is 9.

Among the compounds of the general formula (3) having an anthracene ring structure, the compounds of the general formula (3a), the general formula (3b) or the general formula (3c) having an anthracene ring structure are far preferably used.

$A_2$ in the general formula (3), the general formula (3a), the general formula (3b), or the general formula (3c) is preferably the "divalent group of a substituted or unsubstituted aromatic hydrocarbon" or the "divalent group of substituted or unsubstituted condensed polycyclic aromatics", far preferably, a divalent group that results from the removal of two hydrogen atoms from benzene, biphenyl, naphthalene, or phenanthrene.

In the organic EL device of the present invention, it is preferable that two hole transport layers are laminated. That is, the organic EL device of the present invention in this case have an anode, a first hole transport layer, a second hole transport layer, a light emitting layer, an electron transport layer and a cathode in this order. In this case, the second hole transport layer preferably includes the arylamine compounds of the general formula (1). Further, the first hole transport layer far preferably includes an arylamine compound having a structure in which two to six triphenylamine structures are joined within a molecule via a single bond or a divalent group that does not contain a heteroatom.

The arylamine compounds having a structure in which two to six triphenylamine structures are joined within a molecule via a single bond or a divalent group that does not contain a heteroatom is preferably the arylamine compounds of the general formula (4) having two triphenylamine structures within a molecule or the arylamine compounds of the general formula (5) having four triphenylamine structures within a molecule.

[Chemical Formula 10]

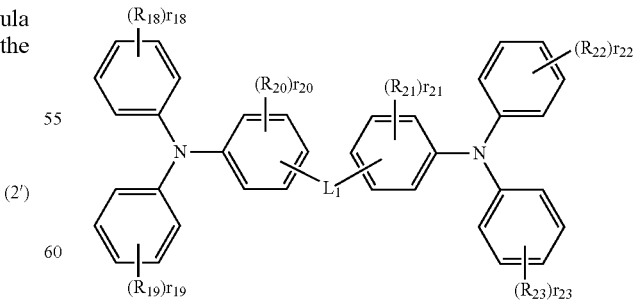

(4)

In the formula, $R_{18}$ to $R_{23}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_{18}$ to $r_{23}$ may be the same or different, $r_{18}$, $r_{19}$, $r_{22}$, and $r_{23}$ representing an integer of 0 to 5, and $r_{20}$ and $r_{21}$ representing an integer of 0 to 4. When $r_{18}$, $r_{19}$, $r_{22}$, and $r_{23}$ are an integer of 2 to 5, or when $r_{20}$ and $r_{21}$ are an integer of 2 to 4, $r_{18}$ to $r_{23}$, a plurality of which bind to the same benzene ring, may be the same or different and may bind to each other via a single bond, substituted or unsubstituted methylene, an oxygen atom, or a sulfur atom to form a ring. $L_1$ represent a divalent group represented by the following structural formulas (C) to (G), or a single bond.

In the formula, $R_{24}$ to R35 represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_{24}$ to $r_{35}$ may be the same or different, $r_{24}$, $r_{25}$, $r_{28}$, $r_{31}$, $r_{34}$, and $r_{35}$ representing an integer of 0 to 5, and $r_{26}$, $r_{27}$, $r_{29}$, $r_{30}$, $r_{32}$, and $r_{33}$ representing an integer of 0 to 4. When $r_{24}$, $r_{25}$, $r_{29}$, $r_{31}$, $r_{34}$, and $r_{35}$ are an integer of 2 to 5, or when $r_{26}$, $r_{27}$, $r_{29}$, $r_{30}$, $r_{32}$, and $r_{33}$ are an integer of 2 to 4, $R_{24}$ to $R_{35}$, a plurality of which bind to the same benzene ring, may

[Chemical Formula 11]

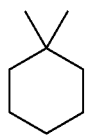

(C)

[Chemical Formula 12]

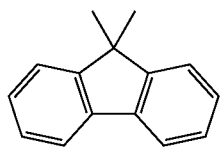

(D)

[Chemical Formula 13]

(E)

[Chemical Formula 14]

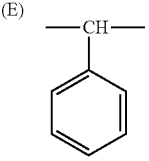

(F)

[Chemical Formula 15]

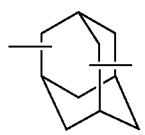

(G)

[Chemical Formula 16]

(5)

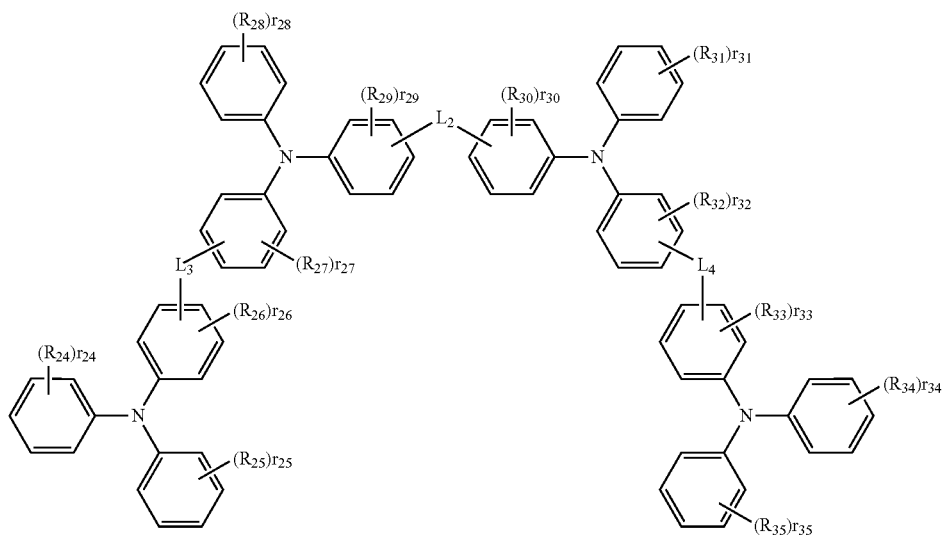

be the same or different and may bind to each other via a single bond, substituted or unsubstituted methylene, an oxygen atom, or a sulfur atom to form a ring. $L_2$, $L_3$, and $L_4$ may be the same or different, and represents a divalent group represented by the following structural formulas (B) to (G), or a single bond.

[Chemical Formula 17]

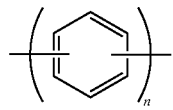
(B)

In the formula, n represents an integer of 1 to 3.

[Chemical Formula 18]

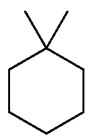
(C)

[Chemical Formula 19]

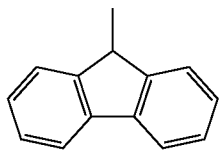
(D)

[Chemical Formula 20]

(E)
—CH$_2$—

[Chemical Formula 21]

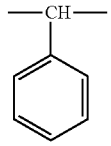
(F)
—CH—

[Chemical Formula 22]

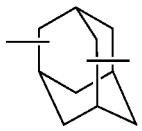
(G)

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{18}$ to $R_{23}$ in the general formula (4) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{10}$ to $R_{16}$ in the general formula (3a), and possible embodiments may also be the same embodiments as the exemplified embodiments.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{18}$ to $R_{23}$ in the general formula (4) include the same groups exemplified as the groups for the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{10}$ to $R_{16}$ in the general formula (3a), and possible embodiments may also be the same embodiments as the exemplified embodiments.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{18}$ to $R_{23}$ in the general formula (4) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aryloxy" in the "substituted or unsubstituted aryloxy" represented by $R_{18}$ to $R_{23}$ in the general formula (4) include the same groups exemplified as the groups for the "aryloxy" in the "substituted or unsubstituted aryloxy" represented by $R_{10}$ to $R_{16}$ in the general formula (3a), and possible embodiments may also be the same embodiments as the exemplified embodiments.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the general formula (4), $r_{18}$ to $r_{23}$ may be the same or different, $r_{18}$, $r_{19}$, $r_{22}$, and $r_{23}$ representing an integer of 0 to 5, and $r_{20}$ and $r_{21}$ representing an integer of 0 to 4. When $r_{18}$, $r_{19}$, $r_{22}$, and $r_{23}$ are an integer of 2 to 5, when $r_{20}$ and $r_{21}$ are an integer of 2 to 4, $R_{18}$ to $R_{23}$, a plurality of which bind to the same benzene ring, may be the same or different and may bind to each other via a single bond, substituted or unsubstituted methylene, an oxygen atom, or a sulfur atom to form a ring.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{24}$ to $R_{35}$ in the general formula (5) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{10}$ to $R_{16}$ in the general formula (3a) and possible embodiments may also be the same embodiments as the exemplified embodiments.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{24}$ to $R_{35}$ in the general formula (5) include the same groups exemplified as the groups for the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{10}$ to $R_{16}$ in the general formula (3a), and possible embodiments may also be the same embodiments as the exemplified embodiments.

These groups may have a substituent, and examples of the substituent include the same substituents exemplified as the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R_{10}$ to $R_{16}$ in the general formula (3a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{24}$ to $R_{35}$ in the general formula (5) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1), these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aryloxy" in the "substituted or unsubstituted aryloxy" represented by $R_{24}$ to $R_{35}$ in the general formula (5) include the same groups exemplified as the groups for the "aryloxy" in the "substituted or unsubstituted aryloxy" represented by $R_{10}$ to $R_{16}$ in the general formula (3a), and possible embodiments may also be the same embodiments as the exemplified embodiments.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

$r_{24}$ to $r_{35}$ in the general formula (5) may be the same or different, $r_{24}$, $r_{25}$, $r_{29}$, $r_{31}$, $r_{34}$, and $r_{35}$ representing an integer of 0 to 5, and $r_{26}$, $r_{27}$, $r_{29}$, $r_{30}$, $r_{32}$, and $r_{33}$ representing an integer of 0 to 4. When $r_{24}$, $r_{25}$, $r_{26}$, $r_{31}$, $r_{34}$, and $r_{35}$ are an integer of 2 to 5, or when $r_{26}$, $r_{27}$, $r_{29}$, $r_{60}$, $r_{32}$, and $r_{33}$ are an integer of 2 to 4, $R_{24}$ to $R_{35}$, a plurality of which bind to the same benzene ring, may be the same or different and may bind to each other via a single bond, substituted or unsubstituted methylene, an oxygen atom, or a sulfur atom to form a ring.

In the structural formula (B), n represents an integer of 1 to 3.

The arylamine compounds of the general formula (1), for preferred use in the organic EL device of the present invention, can be used as a constitutive material of a hole injection layer, an electron blocking layer, or a hole transport layer of an organic EL device. The arylamine compounds of the general formula (1) have high hole mobility and are therefore preferred compounds as material of a hole injection layer or a hole transport layer. Further, the arylamine compounds of the general formula (1) have high electron blocking performance and are therefore preferred compounds as material of an electron blocking layer.

The amine derivatives of the general formula (2) having a condensed ring structure, for preferred use in the organic EL device of the present invention, can be used as a constitutive material of a light emitting layer of an organic EL device. The amine derivatives of the general formula (2) having a condensed ring structure excel in luminous efficiency compared with conventional materials and are therefore preferred compounds as dopant material of a light emitting layer.

The compounds of the general formula (3) having an anthracene ring structure, for preferable use in the organic EL device of the present invention, can be used as a constitutive material of an electron transport layer of an organic EL device.

The compounds of the general formula (3) having an anthracene ring structure excel in electron injection and transport abilities and further excel in stability as a thin film and durability. The compounds are therefore preferred compounds as material of an electron transport layer.

The arylamine compounds of the general formula (4) having two triphenylamine structures within a molecule and the arylamine compounds of the general formula (5) having four triphenylamine structures within a molecule, for preferable use in a first hole transport layer, are preferred compounds as a constitutive material of a hole injection layer or a hole transport layer of an organic EL device in the case where a hole transport layer has a two-layer structure of a first hole transport layer and a second hole transport layer for preferable form in the organic EL device of the present invention.

A second hole transport layer, in the case where a hole transport layer has a two-layer structure of a first hole transport layer and a second hole transport layer for preferable embodiments in the organic EL device of the present invention, preferably includes the arylamine compounds of the general formula (1).

The organic EL device of the present invention combines materials for an organic EL device excelling in hole and electron injection/transport performances, stability as a thin film and durability, taking carrier balance that matching characteristics of a light-emitting material having a specific structure into consideration. Therefore, compared with the conventional organic EL devices, hole transport efficiency to the light emitting layer from the hole transport layer is improved and electron transport efficiency to the light emitting layer from the electron transport layer is also improved (and the organic EL device of the present invention combines two kinds of arylamine compounds having specific structures taking carrier balance and characteristics of materials into consideration). As a result, luminous efficiency is improved and driving voltage is decreased, and durability of the organic EL device can thereby be improved.

Thus, an organic EL device having high efficiency, low driving voltage, and a long lifetime can be attained in the present invention.

Effects of the Invention

The organic EL device of the present invention can achieve an organic EL device having high efficiency, low driving voltage and a long lifetime as a result of attaining efficient hole injection/transport into a light emitting layer by selecting specific arylamine compounds which excel in hole and electron injection/transport performances, stability as a thin film and durability and can effectively exhibit hole injection/transport roles. An organic EL device having high efficiency, low driving voltage, and a long lifetime can be achieved by selecting specific arylamine compounds, and combining those compounds and a specific electron transport material so as to achieve good carrier balance that matching characteristics of a light-emitting material having a specific structure. Furthermore, in the case where a hole transport layer has a two-layer structure of a first hole transport layer and a second hole transport layer, the organic EL device of the present invention can achieve an organic EL device having high efficiency and a long lifetime by combining two kinds of arylamine compounds having specific structures taking carrier balance and characteristics of materials into consideration. The organic EL device of the present invention can improve luminous efficiency, driving voltage, and durability of the conventional organic EL devices.

BRIEF DESCRIPTION OF THE DRAWINGS

FIG. 1 is a diagram illustrating the configuration of the organic EL devices of Examples 32 to 46 and Comparative Examples 1 to 3.

MODE FOR CARRYING OUT THE INVENTION

The following presents specific examples of preferred compounds among the arylamine compounds of the general formula (1) preferably used in the organic EL device of the present invention. The present invention, however, is not restricted to these compounds.

[Chemical Formula 23]

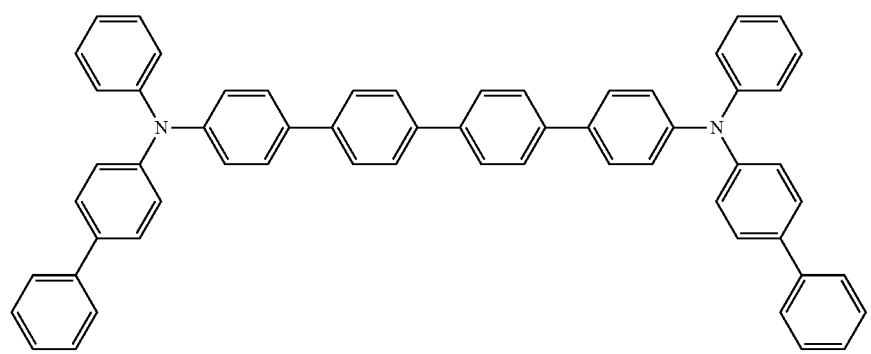

(1-1)

[Chemical Formula 24]
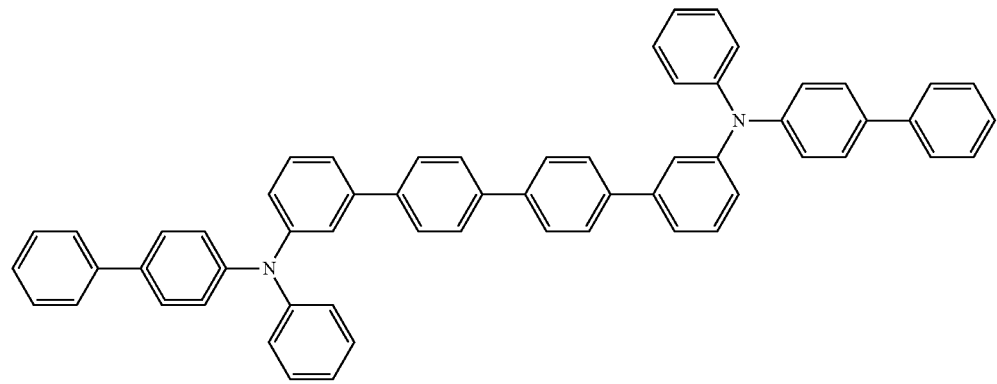
(1-2)
[Chemical Formula 25]
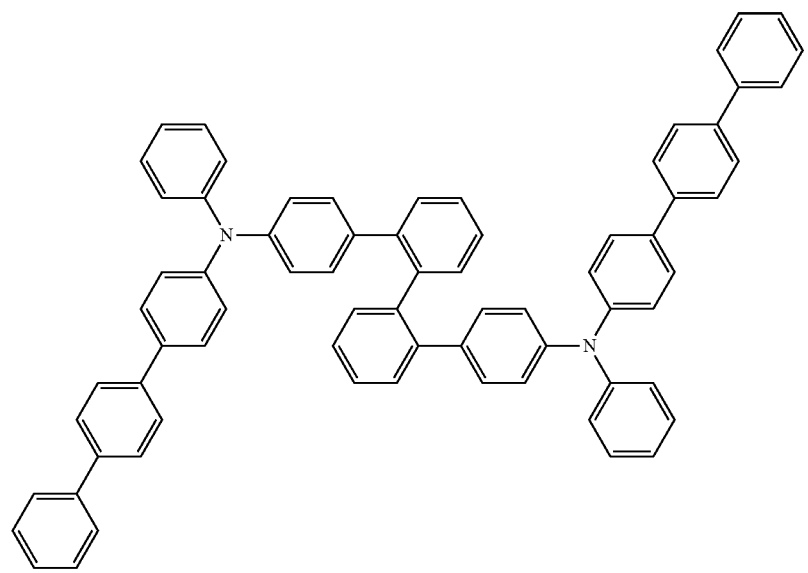
(1-3)
[Chemical Formula 26]
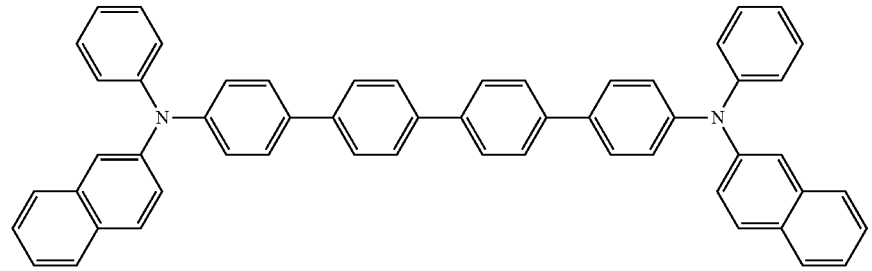
(1-4)

[Chemical Formula 27]
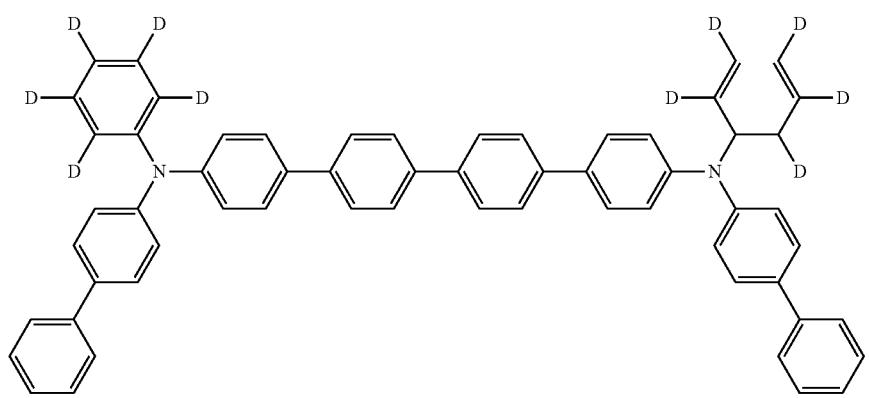
(1-5)
[Chemical Formula 28]
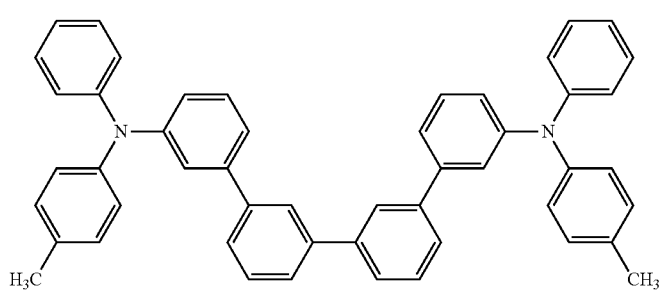
(1-6)
[Chemical Formula 29]
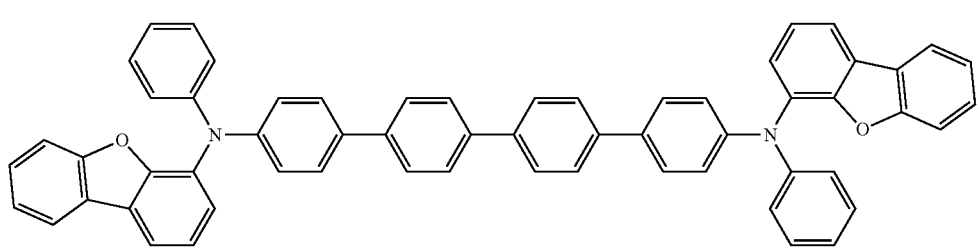
(1-7)
[Chemical Formula 30]
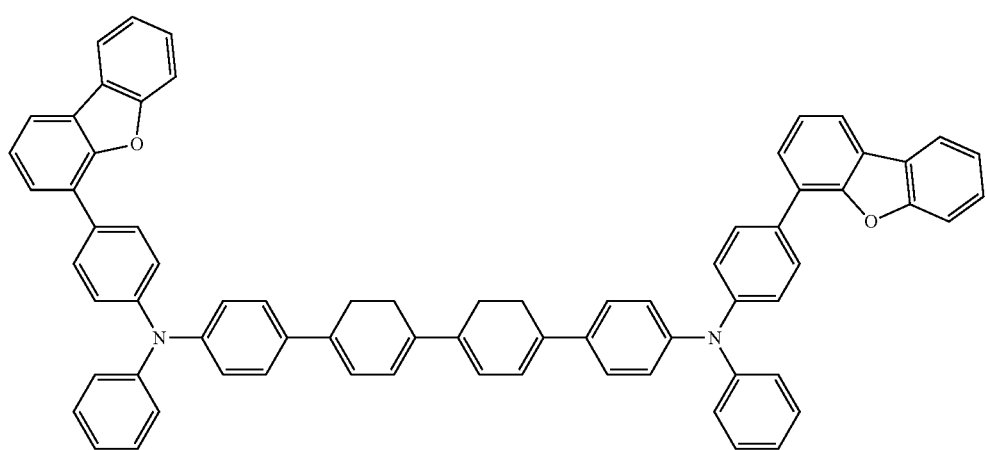
(1-8)

[Chemical Formula 31]
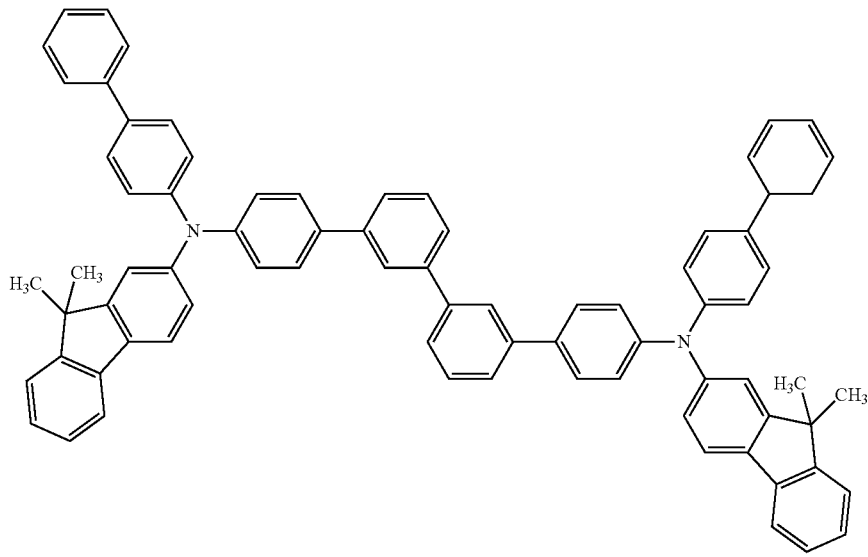
(1-9)
[Chemical Formula 32]
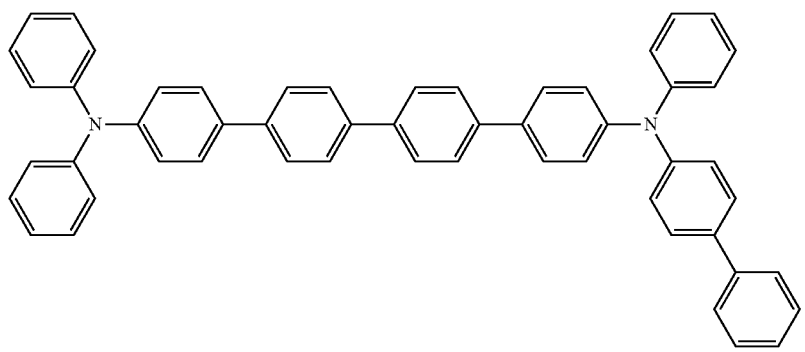
(1-10)
[Chemical Formula 33]
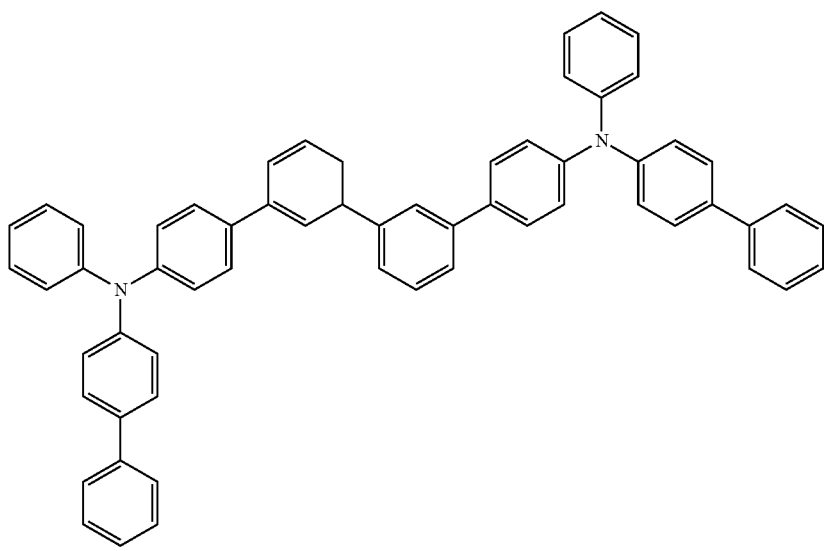
(1-11)

-continued
[Chemical Formula 34]
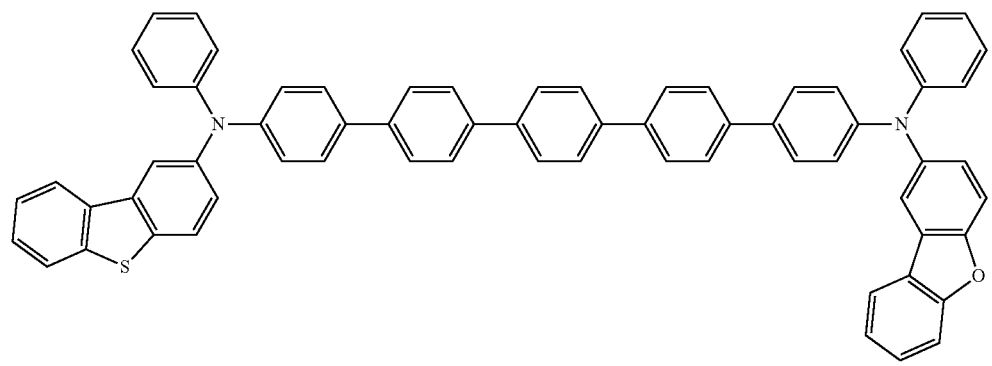
(1-12)
[Chemical Formula 35]
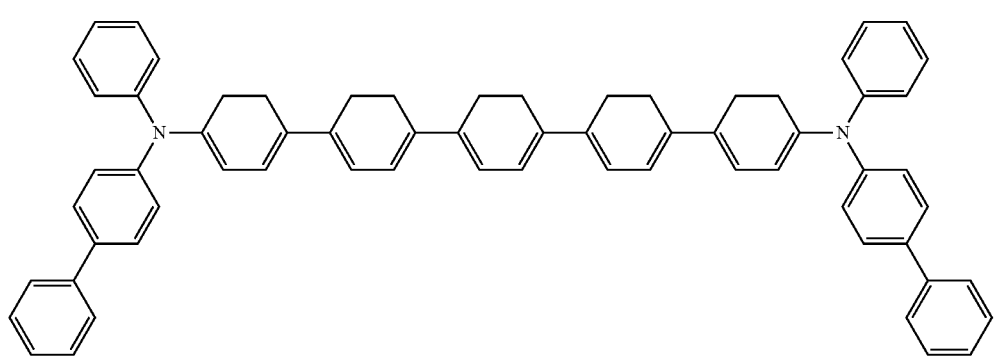
(1-13)
[Chemical Formula 36]
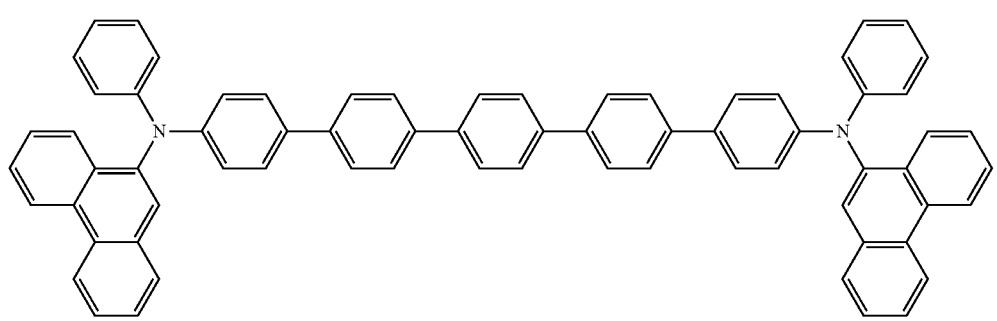
(1-14)
[Chemical Formula 37]
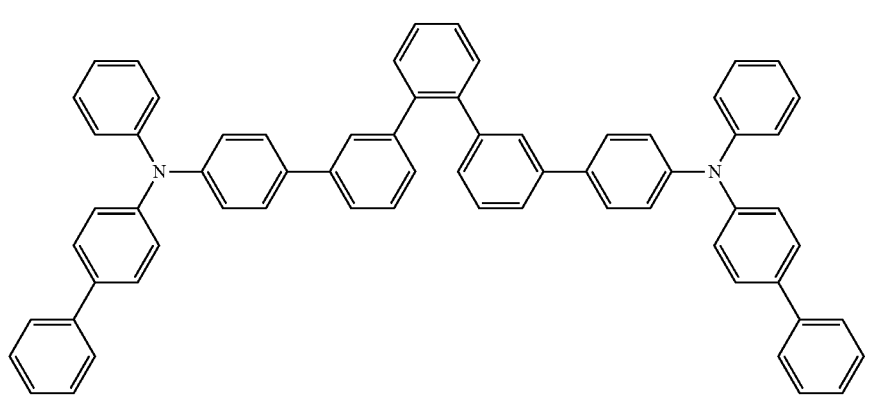
(1-15)

[Chemical Formula 38]
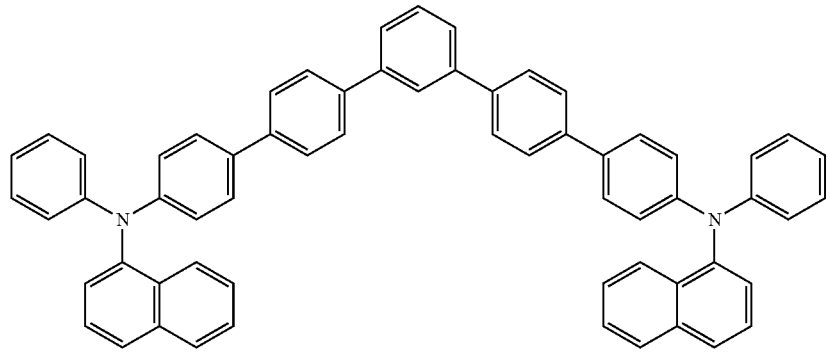
(1-16)
[Chemical Formula 39]
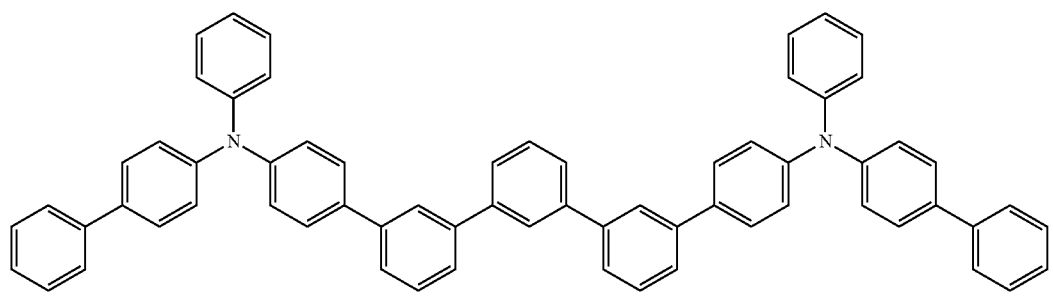
(1-17)
[Chemical Formula 40]
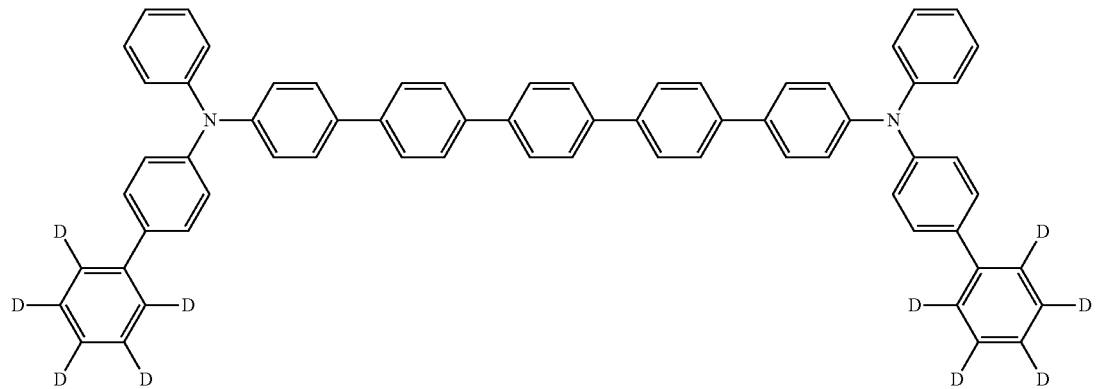
(1-18)
[Chemical Formula 41]
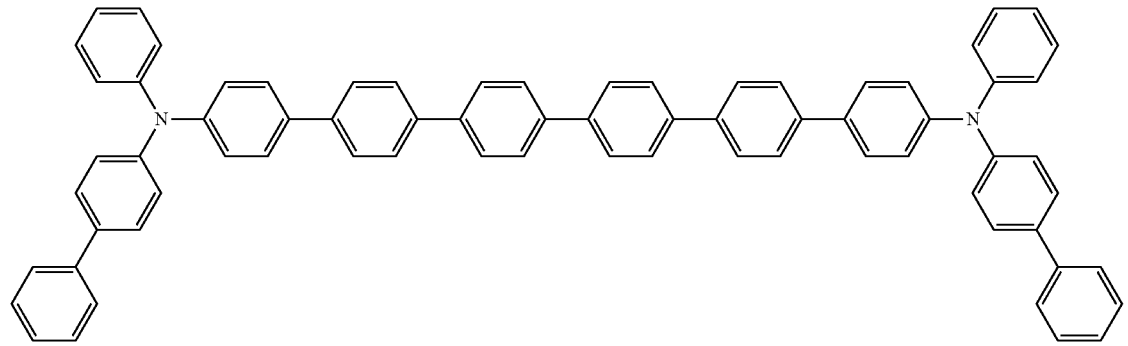
(1-19)

[Chemical Formula 42]
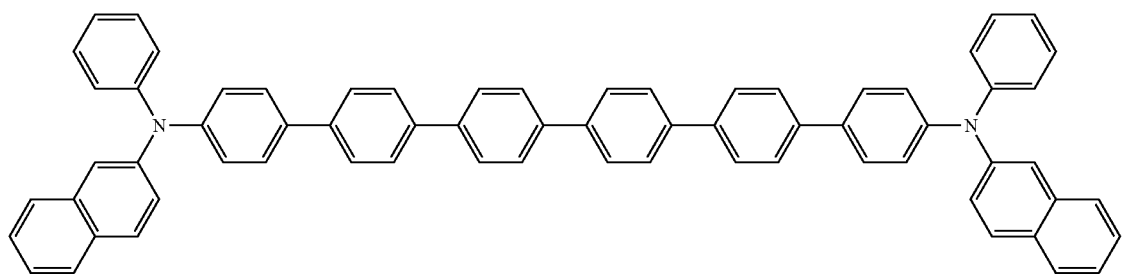
(1-20)
[Chemical Formula 43]
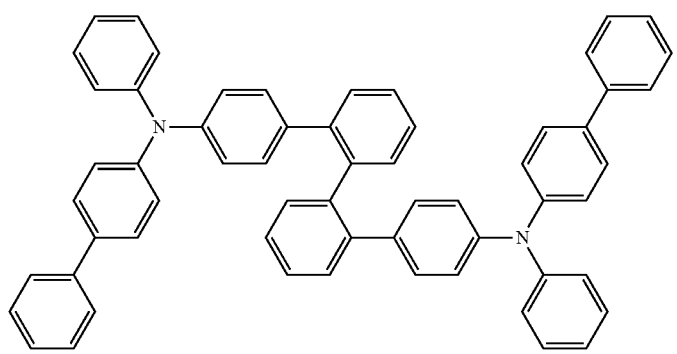
(1-21)
[Chemical Formula 44]
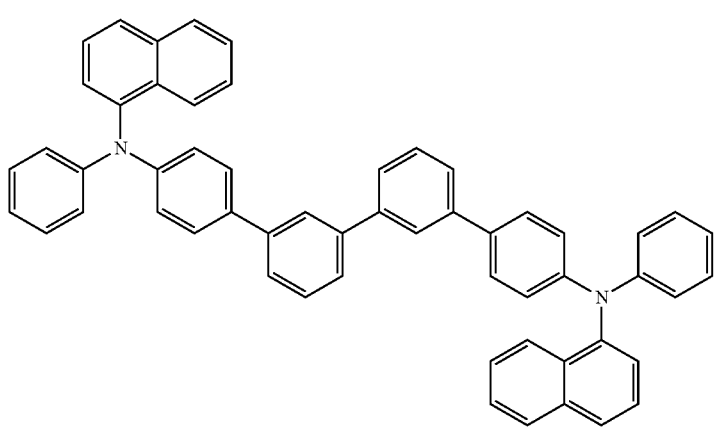
(1-22)
[Chemical Formula 45]
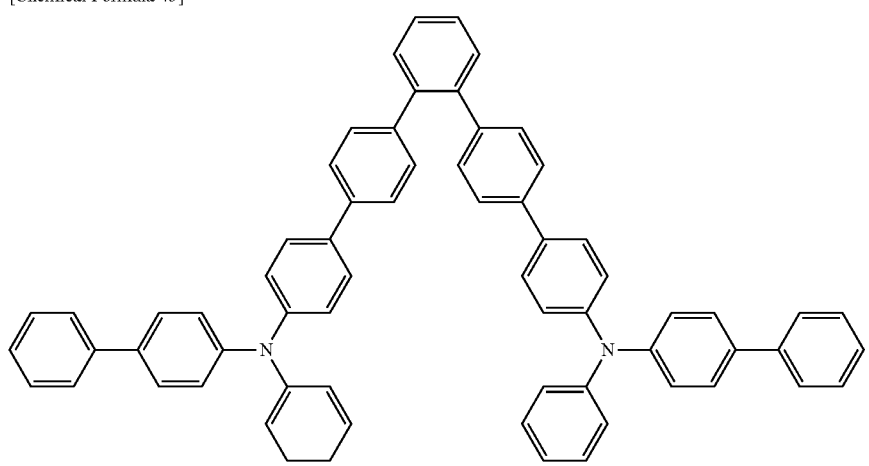
(1-23)

[Chemical Formula 46]
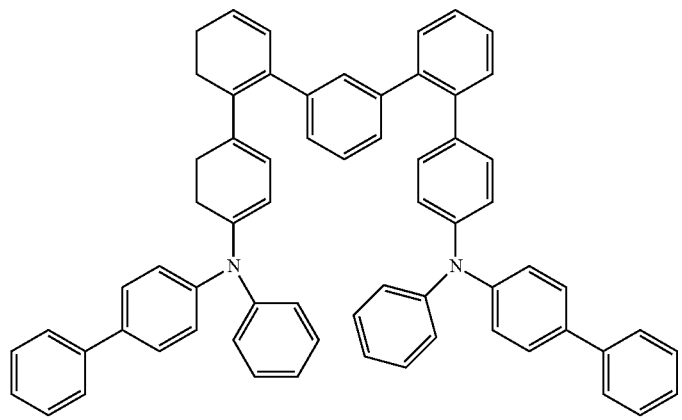
(1-24)
[Chemical Formula 47]
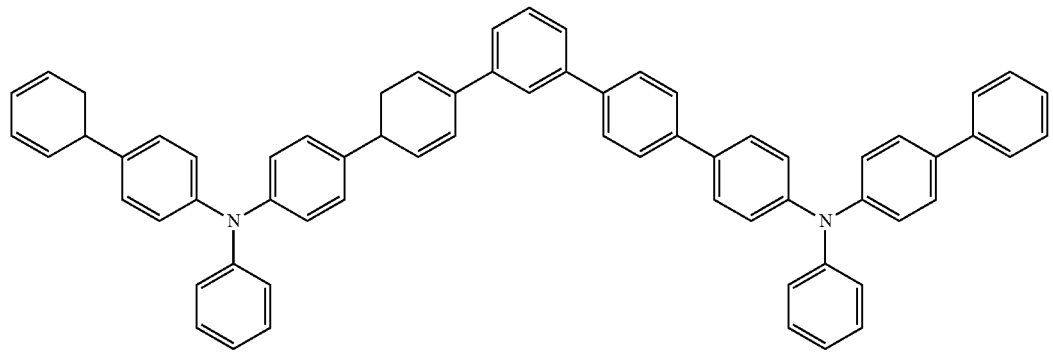
(1-25)
[Chemical Formula 48]
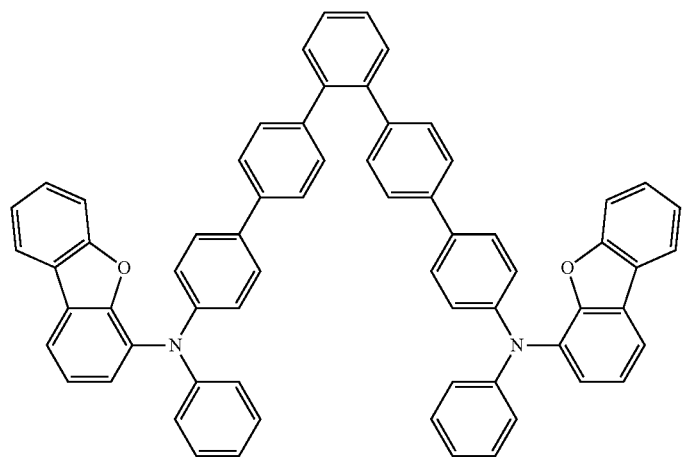
(1-26)

-continued
[Chemical Formula 49]
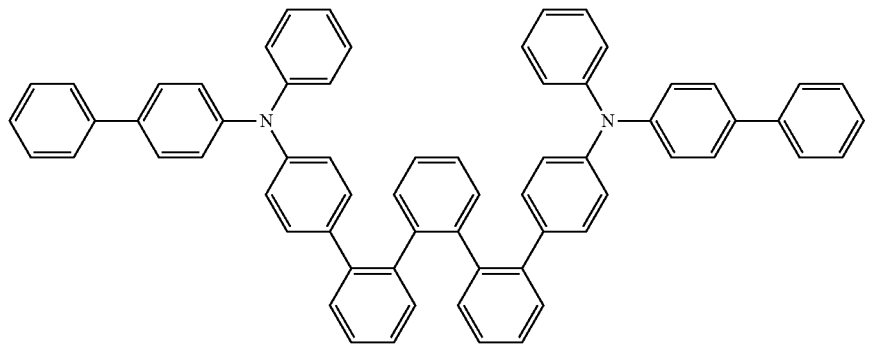
(1-27)
[Chemical Formula 50]
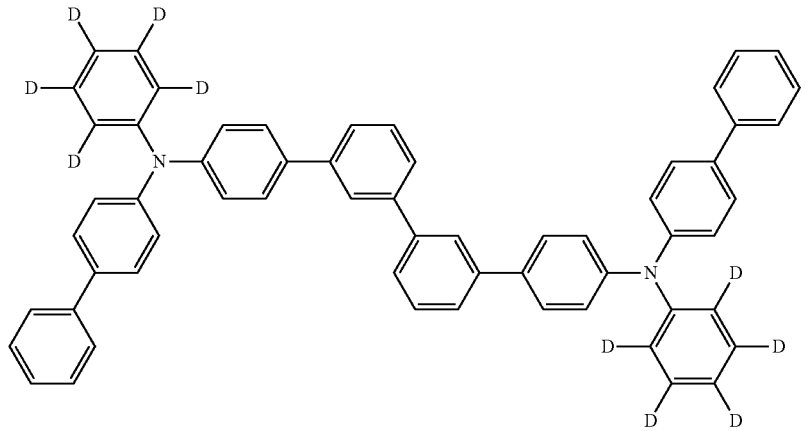
(1-28)
[Chemical Formula 51]
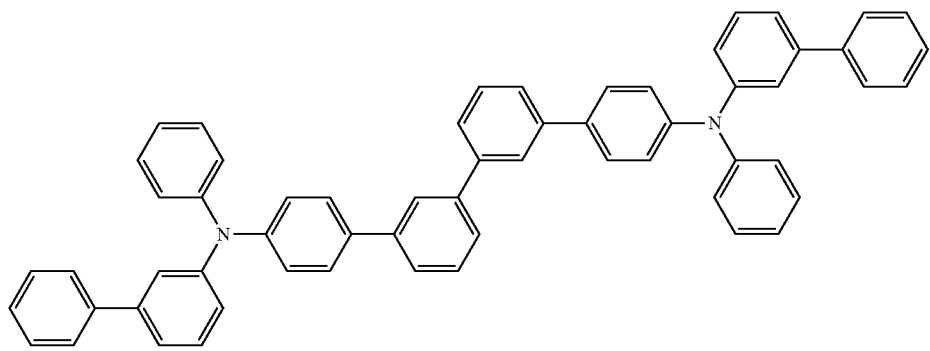
(1-29)
[Chemical Formula 52]
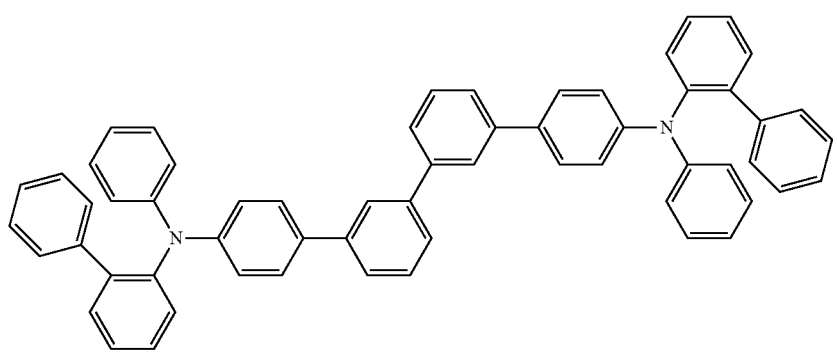
(1-30)

[Chemical Formula 53]
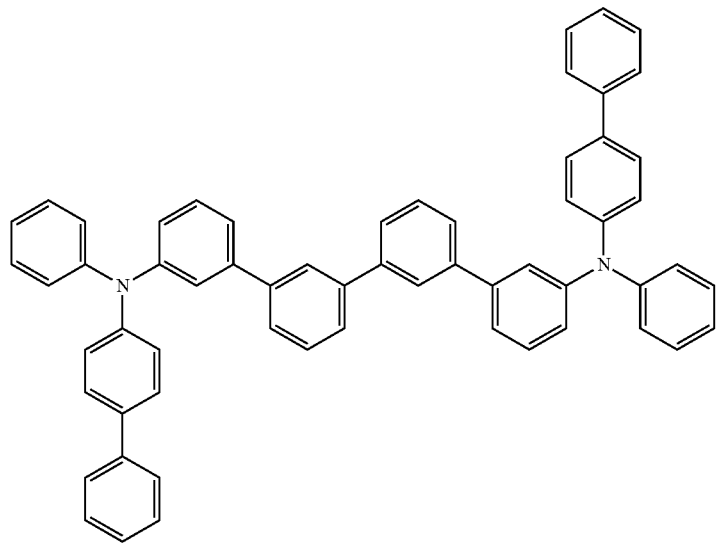
(1-31)
[Chemical Formula 54]
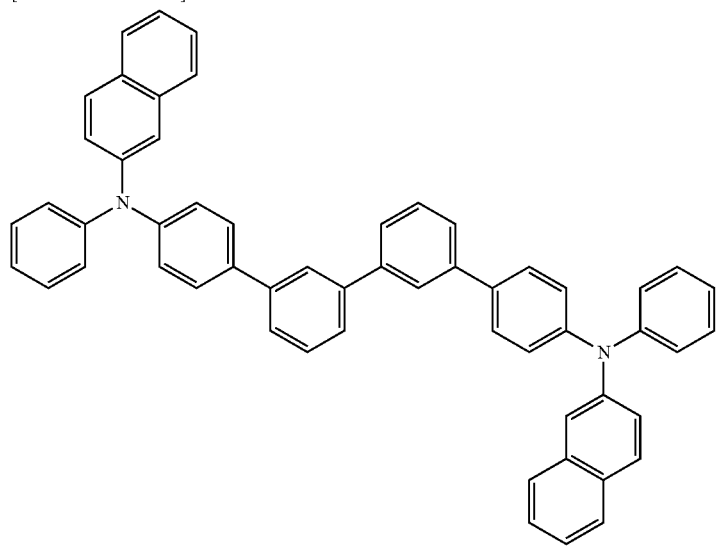
(1-32)
[Chemical Formula 55]
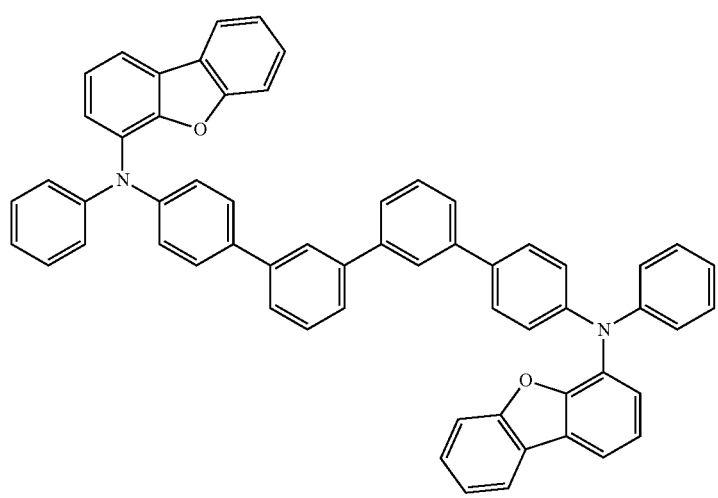
(1-33)

[Chemical Formula 56]
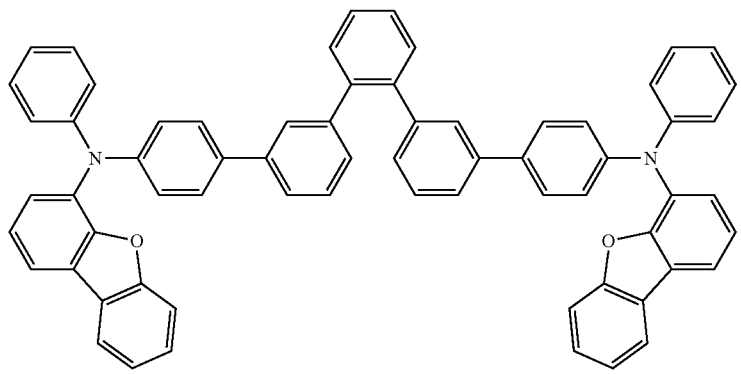
(1-34)
[Chemical Formula 57]
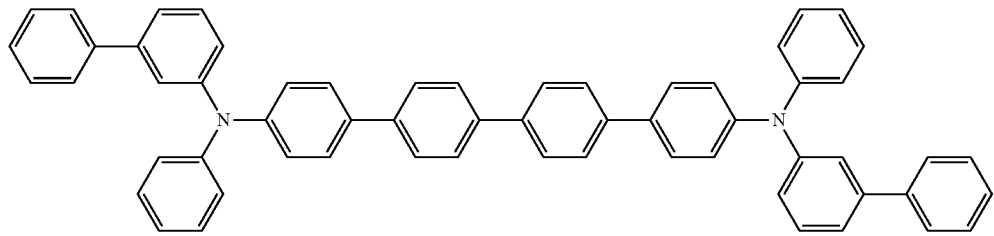
(1-35)
[Chemical Formula 58]
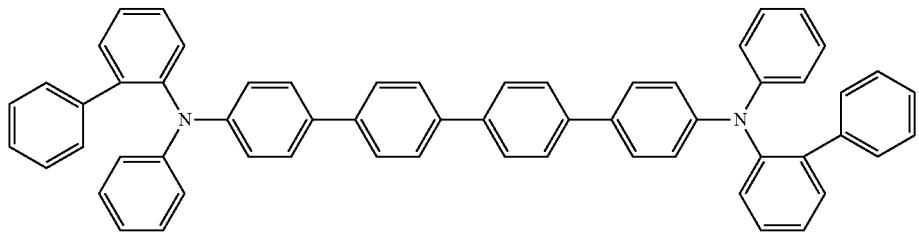
(1-36)
[Chemical Formula 59]
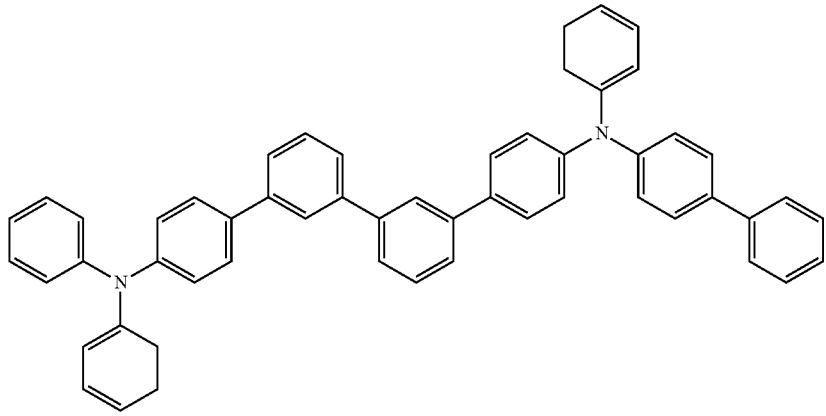
(1-37)

[Chemical Formula 60]
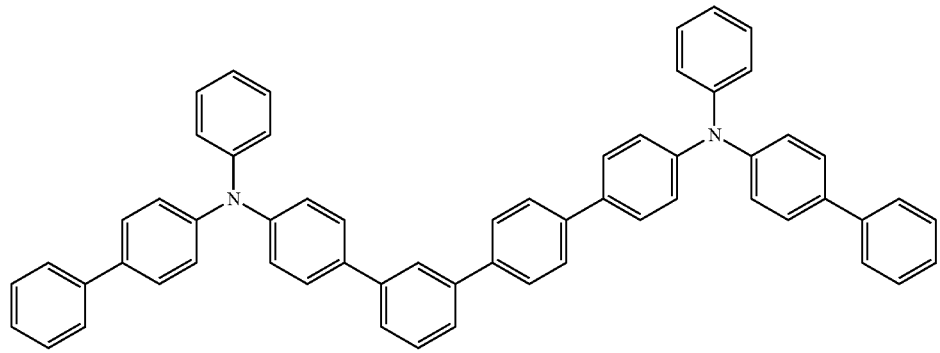
(1-38)
[Chemical Formula 61]
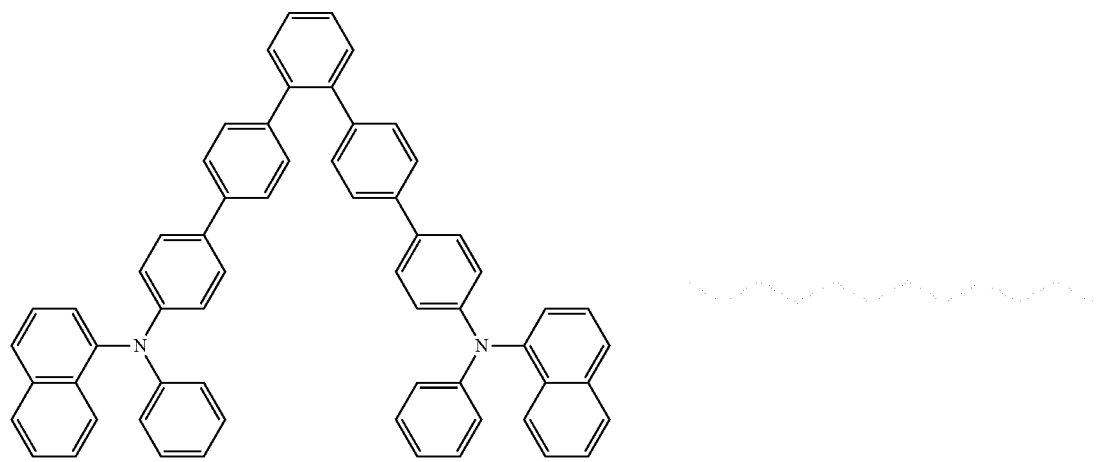
(1-39)
[Chemical Formula 62]
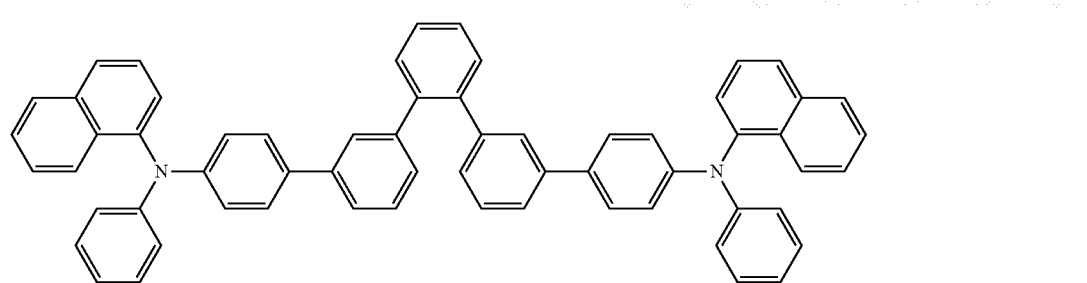
(1-40)

[Chemical Formula 63]

(1-41)

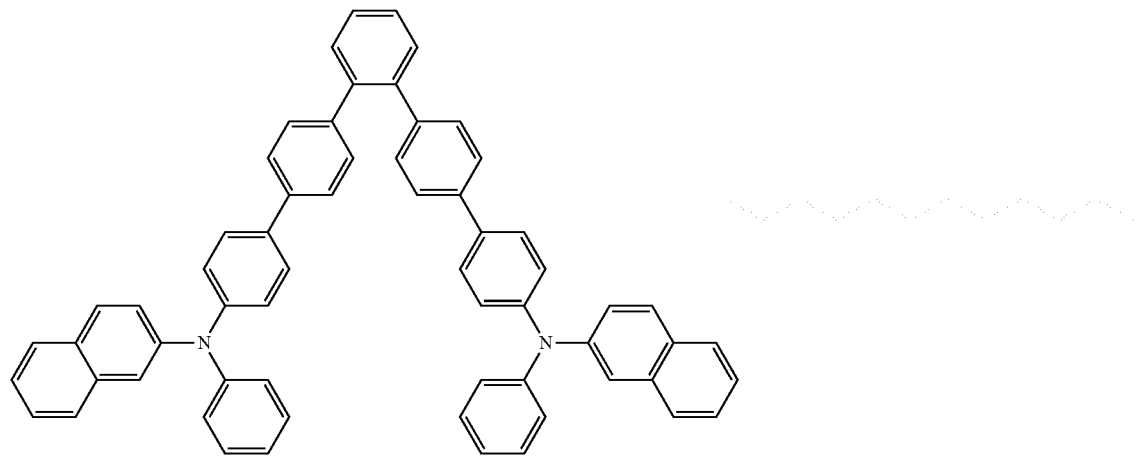

[Chemical Formula 64]

(1-42)

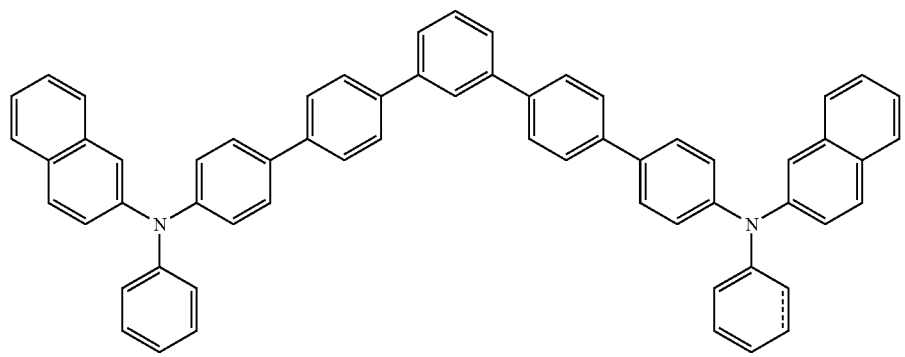

The following presents specific examples of preferred compounds among the amine derivatives of the general formula (2) having a condensed ring structure preferably used in the organic EL device of the present invention. The present invention, however, is not restricted to these compounds.

[Chemical Formula 65]

(2-1)

[Chemical Formula 66]

(2-2)

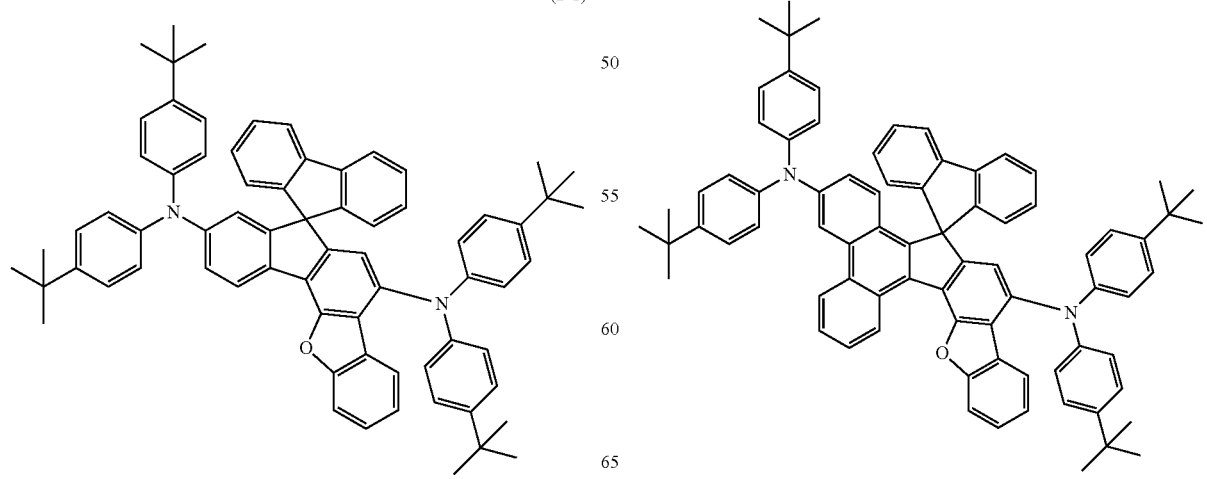

[Chemical Formula 67]
(2-3)
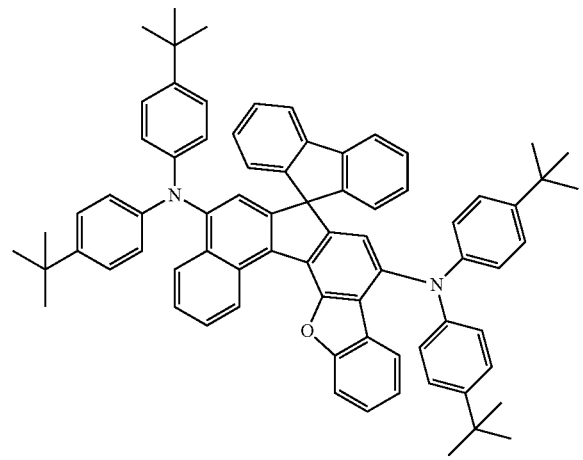
[Chemical Formula 68]
(2-4)
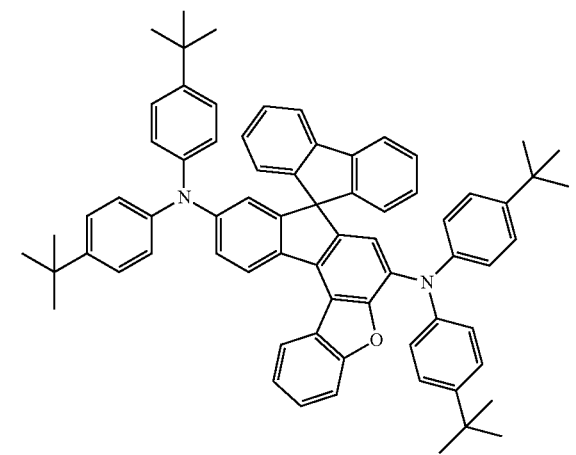
[Chemical Formula 69]
(2-5)
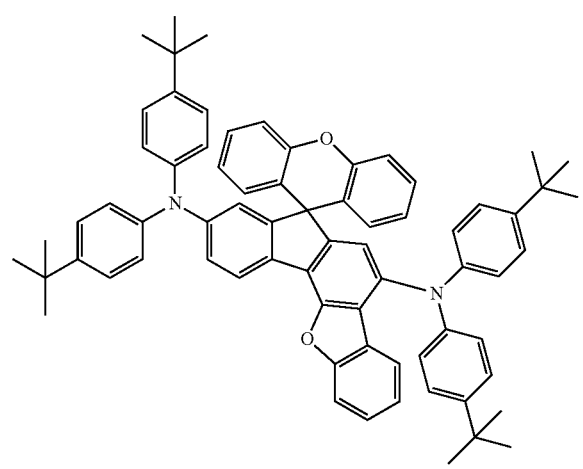
[Chemical Formula 70]
(2-6)
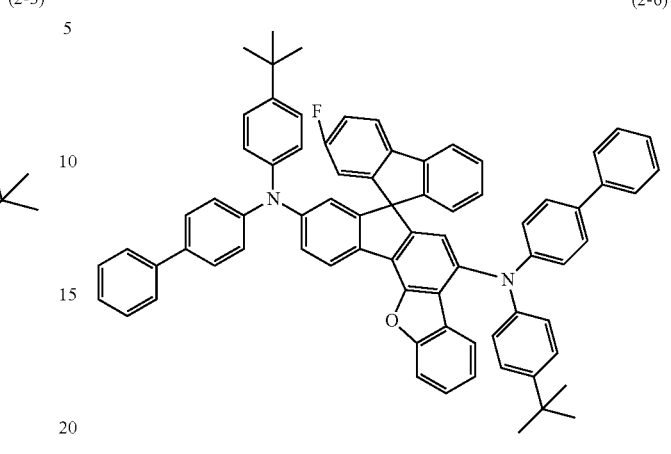
[Chemical Formula 71]
(2-7)
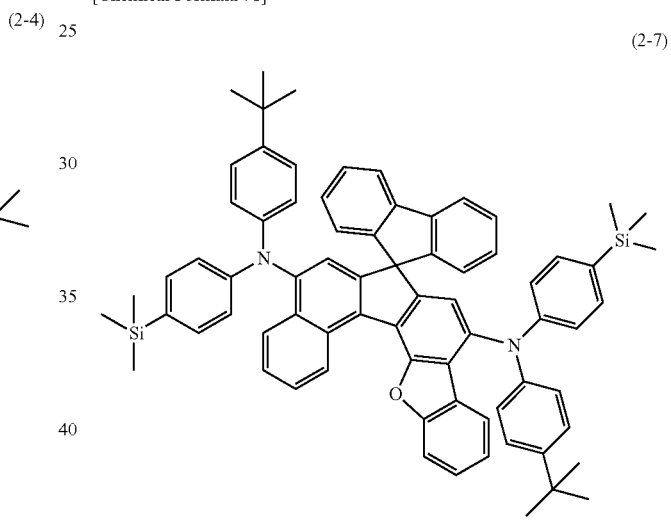
[Chemical Formula 72]
(2-8)
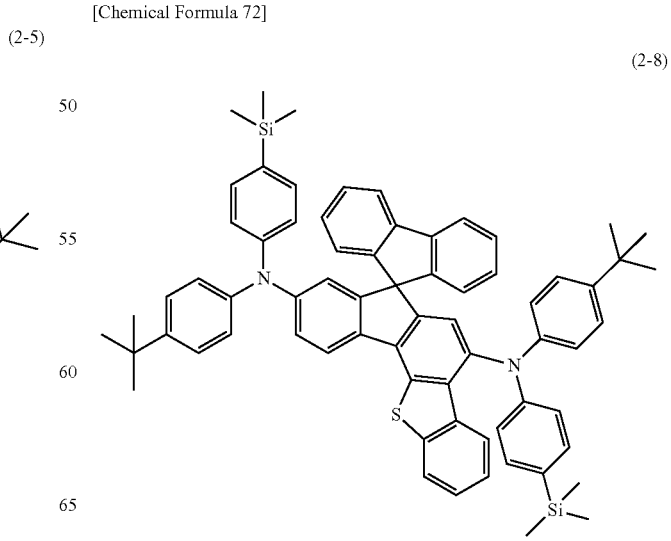

[Chemical Formula 73]
(2-9)
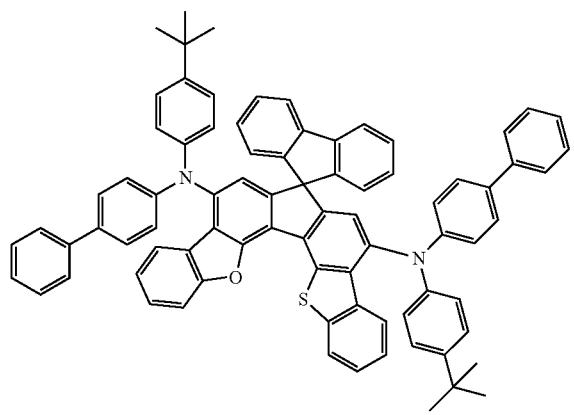
[Chemical Formula 74]
(2-10)
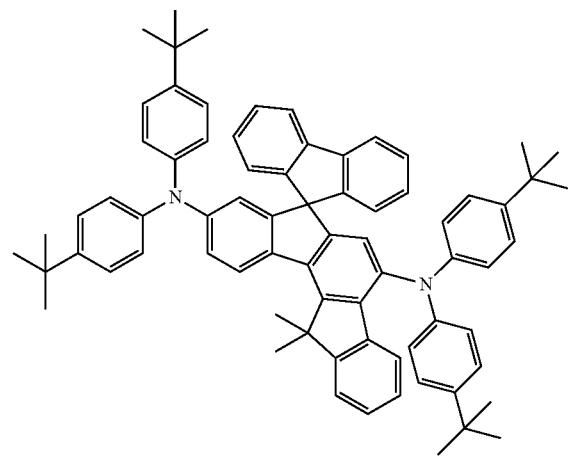
[Chemical Formula 75]
(2-11)
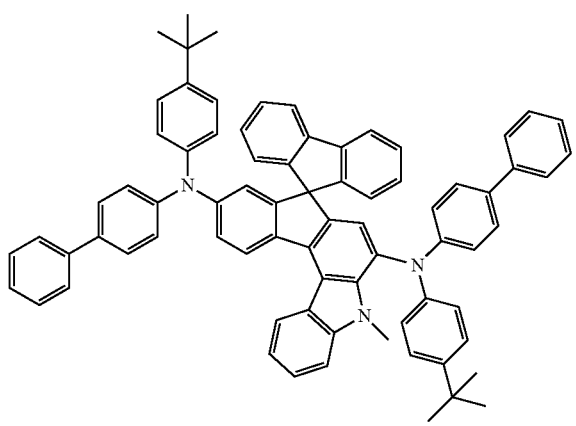
[Chemical Formula 76]
(2-12)
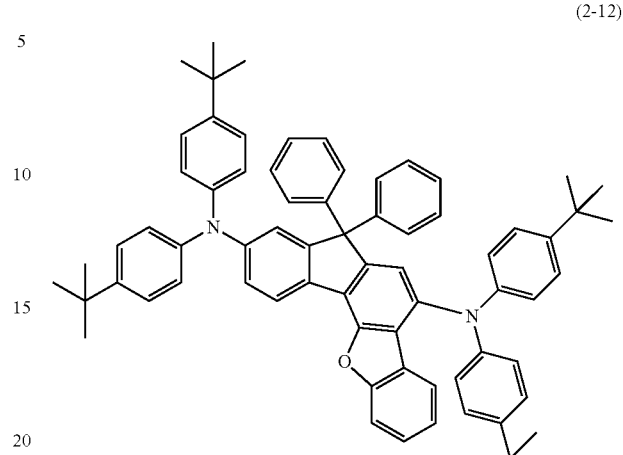
[Chemical Formula 77]
(2-13)
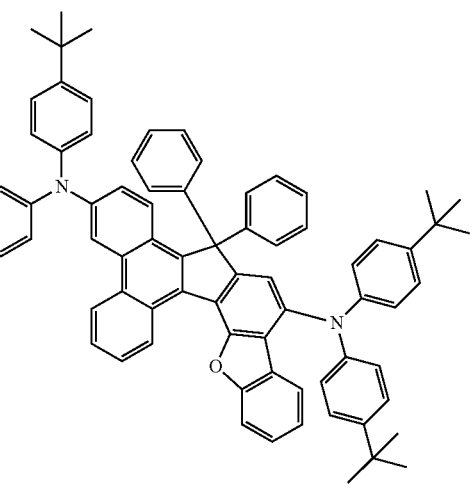
[Chemical Formula 78]
(2-14)
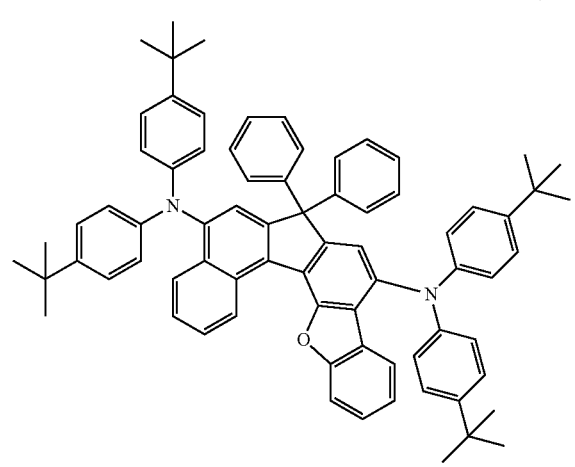

[Chemical Formula 79]
(2-15)
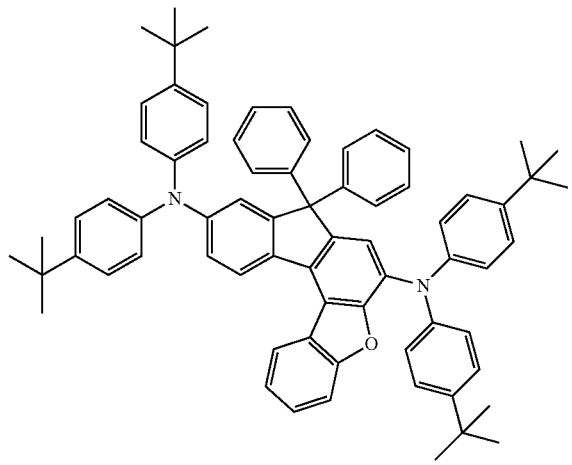
[Chemical Formula 80]
(2-16)
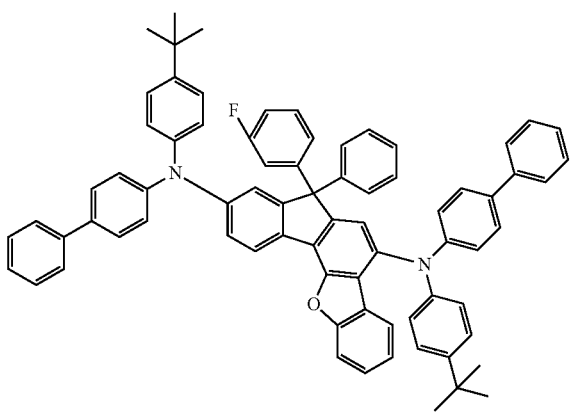
[Chemical Formula 81]
(2-17)
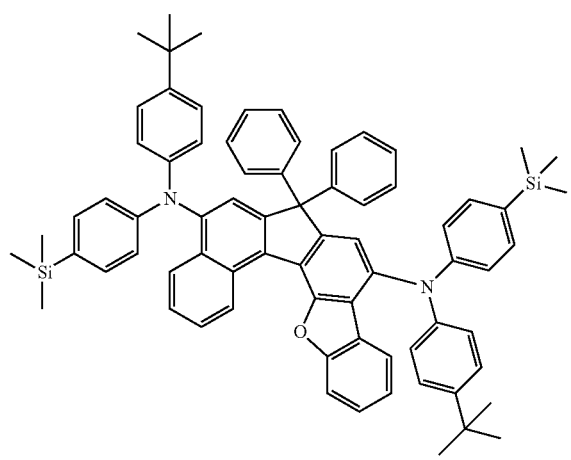
[Chemical Formula 82]
(2-18)
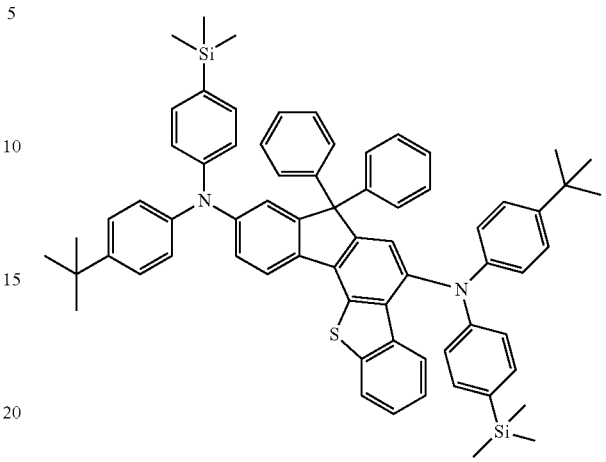
[Chemical Formula 83]
(2-19)
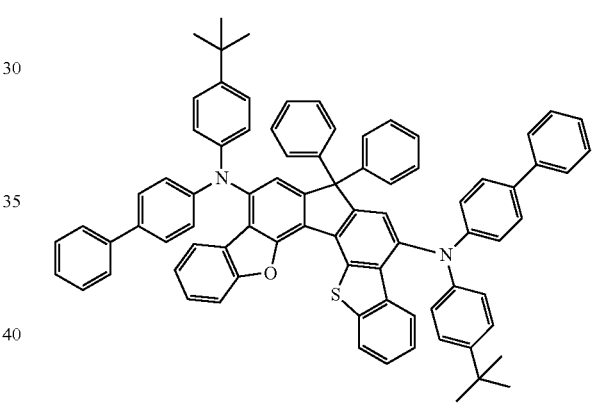
[Chemical Formula 84]
(2-20)
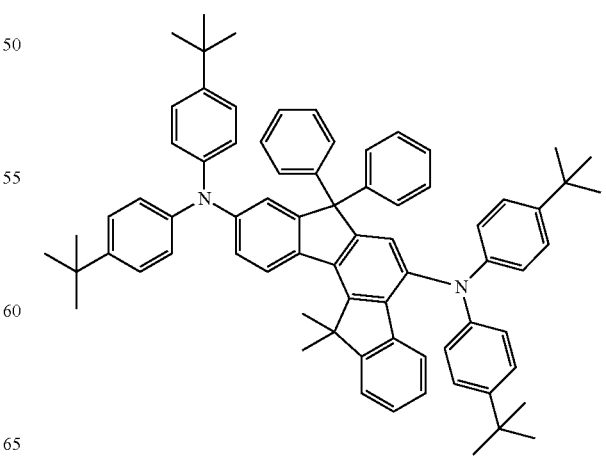

[Chemical Formula 85]

(2-21)

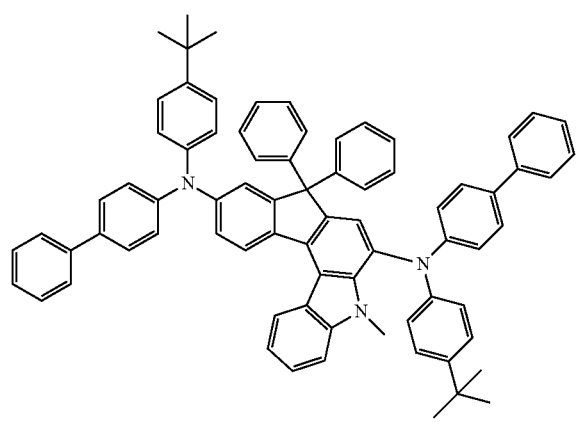

[Chemical Formula 86]

(2-22)

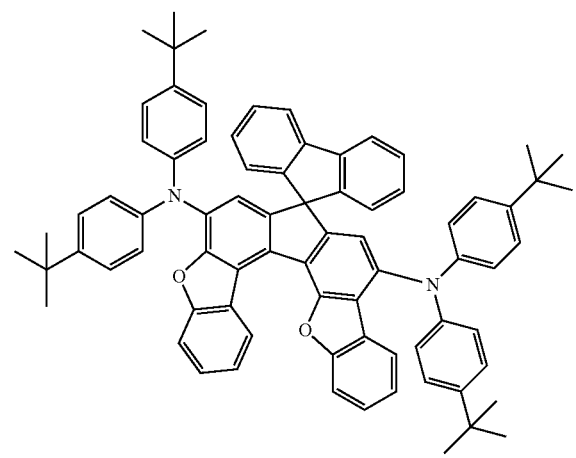

[Chemical Formula 87]

(2-23)

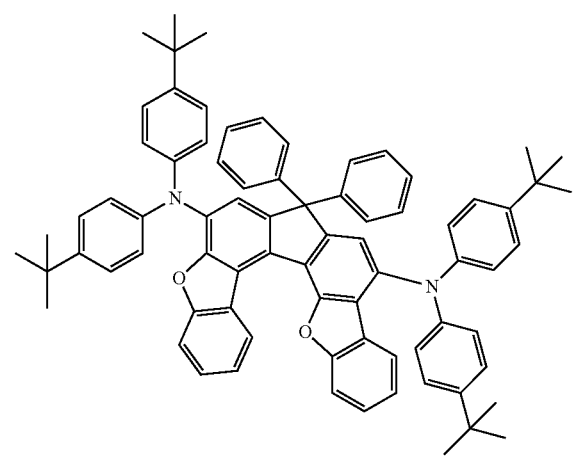

[Chemical Formula 88]

(2-24)

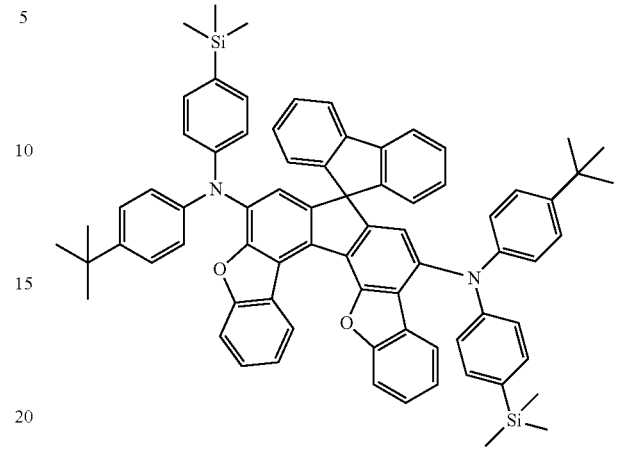

[Chemical Formula 89]

(2-25)

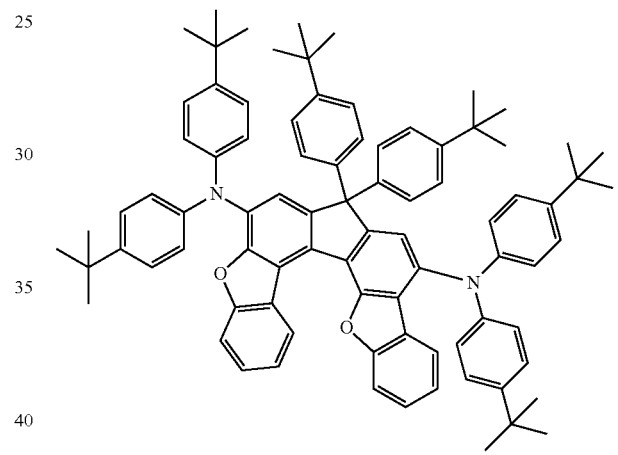

The following presents specific examples of preferred compounds among the compounds of the general formula (3a) having an anthracene ring structure and preferably used in the organic EL device of the present invention. The present invention and, however, is not restricted to these compounds.

[Chemical Formula 90]

(3a-1)

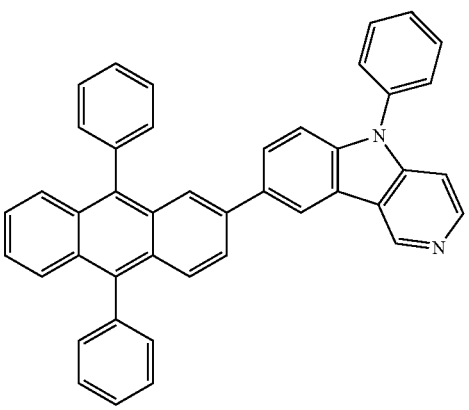

[Chemical Formula 91]
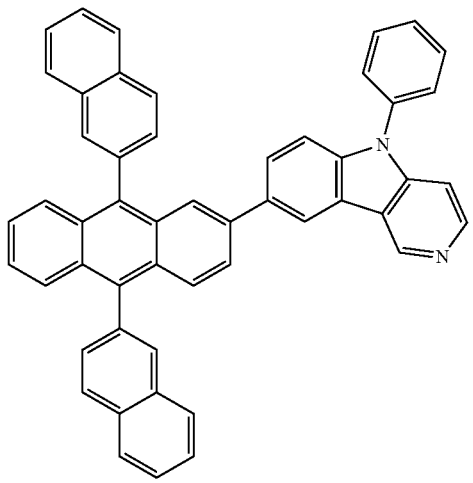
(3a-2)
[Chemical Formula 92]
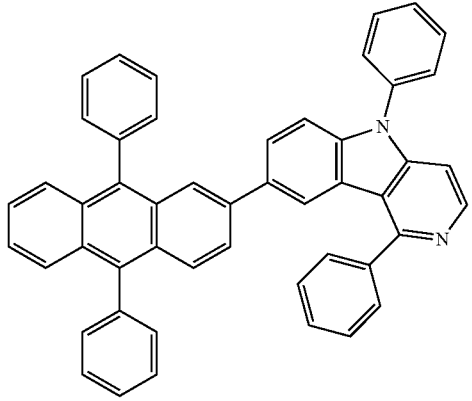
(3a-3)
[Chemical Formula 93]
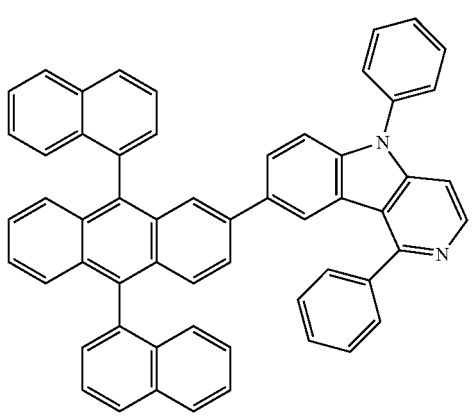
(3a-4)
[Chemical Formula 94]
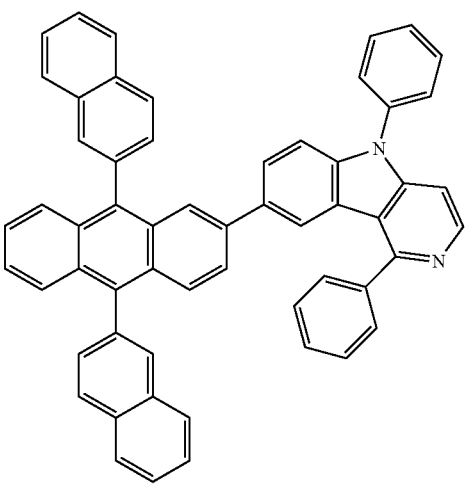
(3a-5)
[Chemical Formula 95]
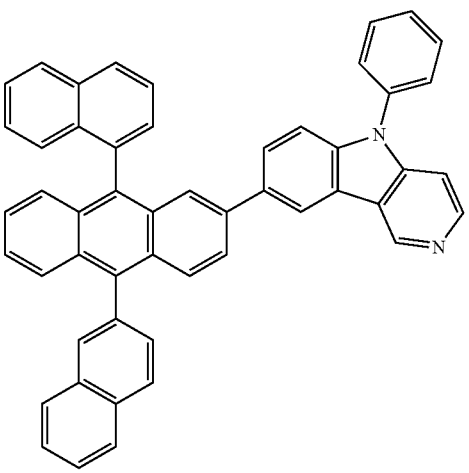
(3a-6)
[Chemical Formula 96]
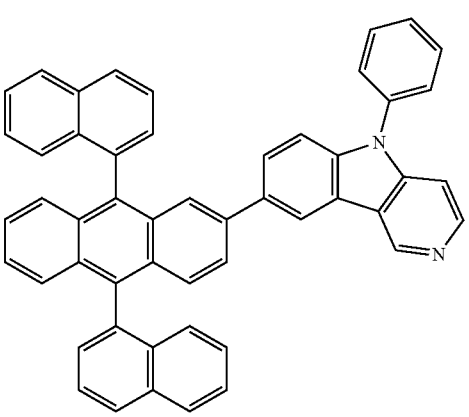
(3a-7)

[Chemical Formula 97]
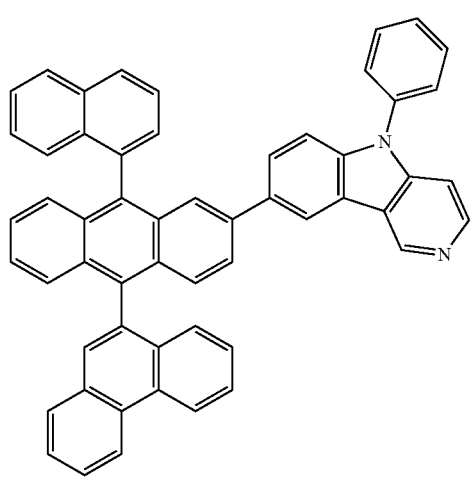
(3a-8)
[Chemical Formula 98]
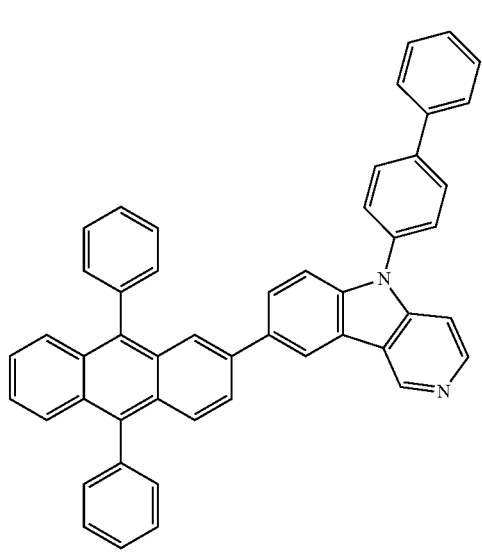
(3a-9)
[Chemical Formula 99]
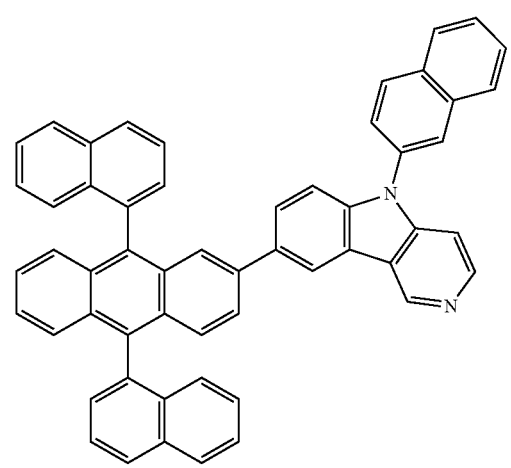
(3a-10)
[Chemical Formula 100]
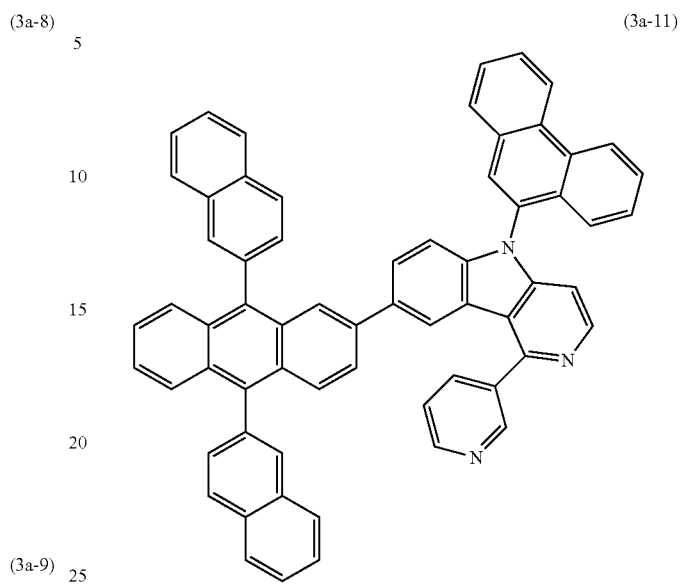
(3a-11)
[Chemical Formula 101]
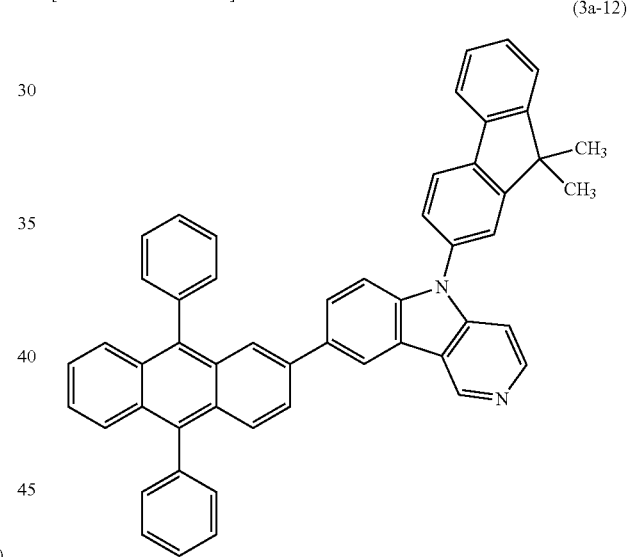
(3a-12)
[Chemical Formula 102]
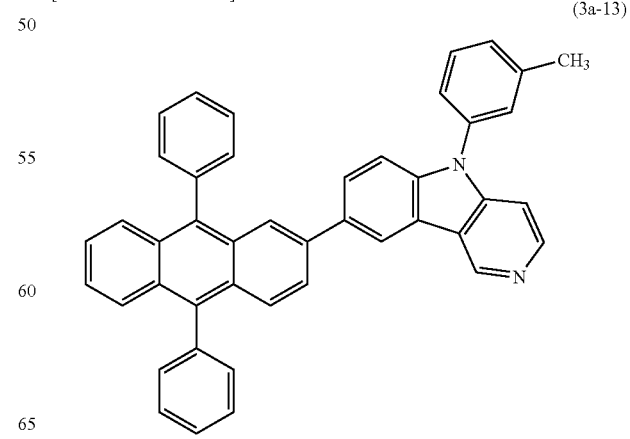
(3a-13)

[Chemical Formula 103]
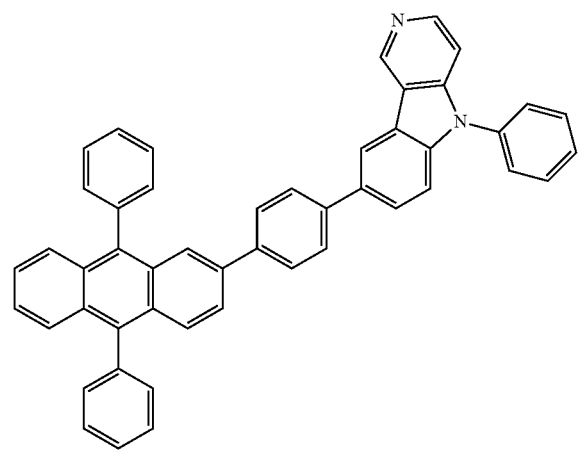
(3a-14)
[Chemical Formula 104]
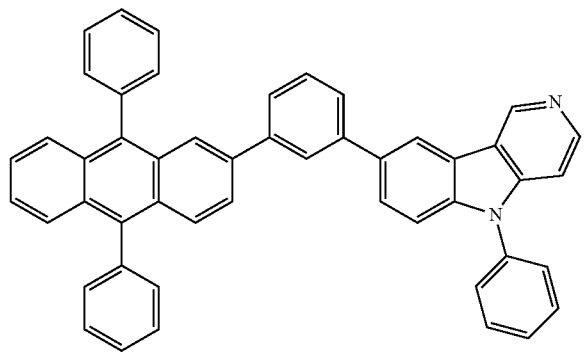
(3a-15)
[Chemical Formula 105]
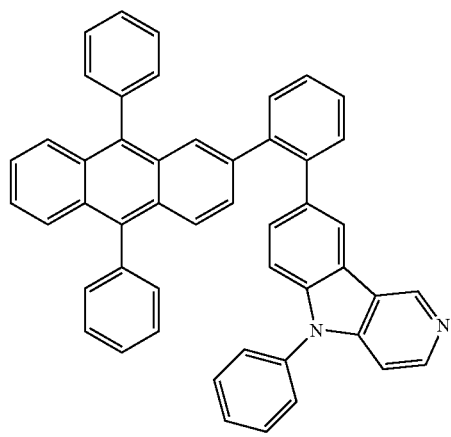
(3a-16)
[Chemical Formula 106]
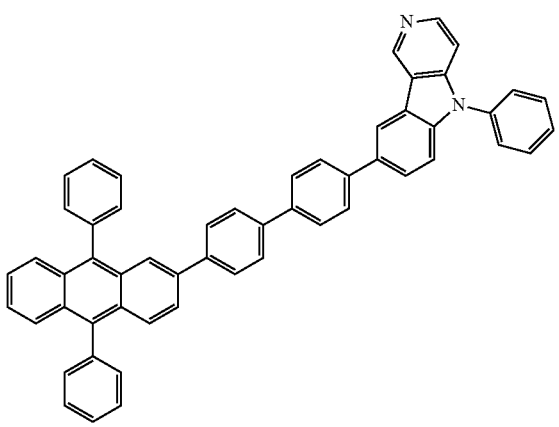
(3a-17)
[Chemical Formula 107]
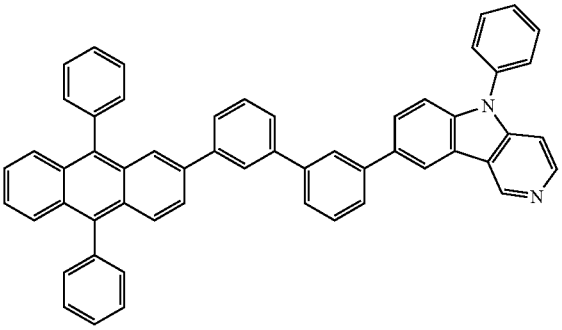
(3a-18)
[Chemical Formula 108]
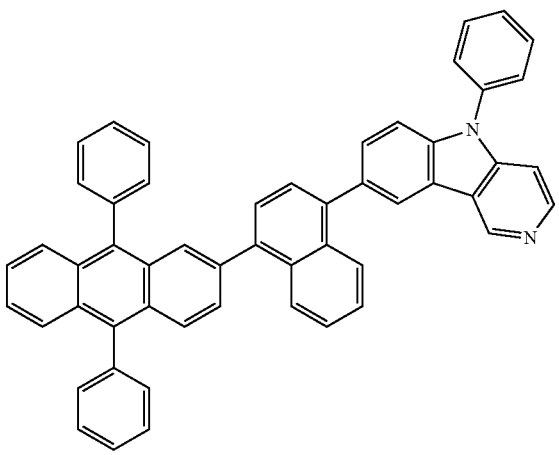
(3a-19)

[Chemical Formula 109]

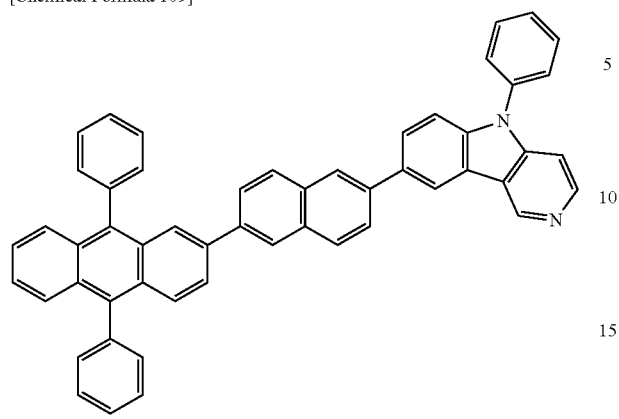

(3a-20)

The following presents specific examples of preferred compounds among the compounds of the general formula (3b) having an anthracene ring structure and preferably used in the organic EL device of the present invention. The present invention, however, is not restricted to these compounds.

[Chemical Formula 110]

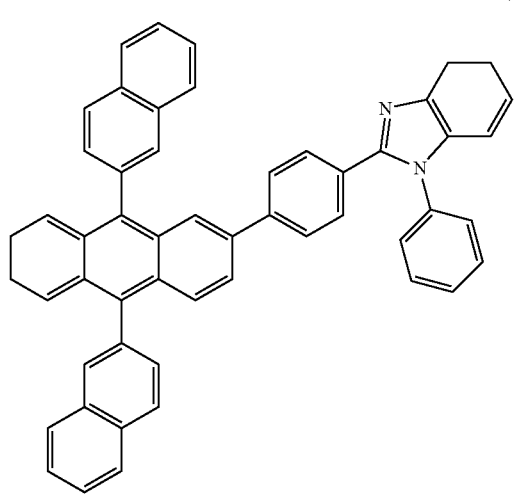

(3b-1)

[Chemical Formula 111]

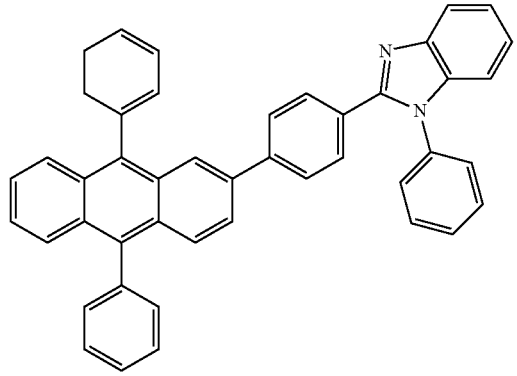

(3b-2)

[Chemical Formula 112]

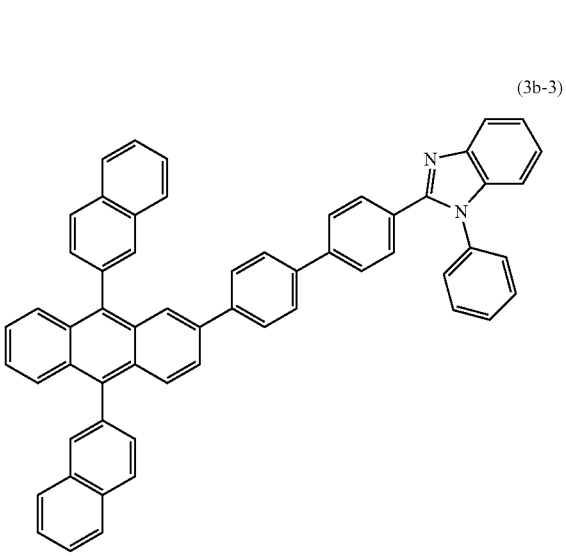

(3b-3)

[Chemical Formula 113]

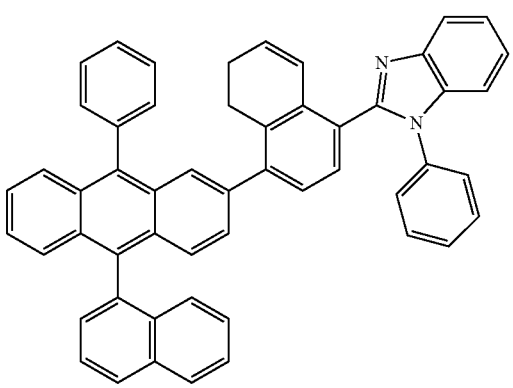

(3b-4)

[Chemical Formula 114]

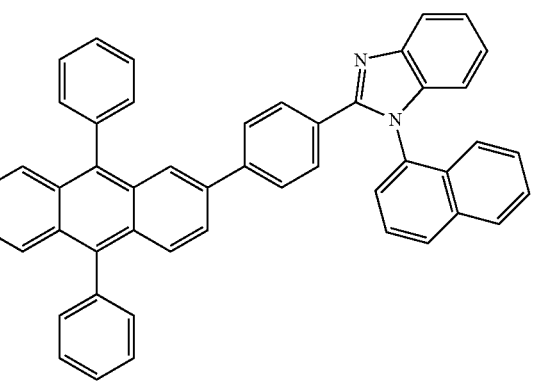

(3b-5)

[Chemical Formula 115]
(3b-6)
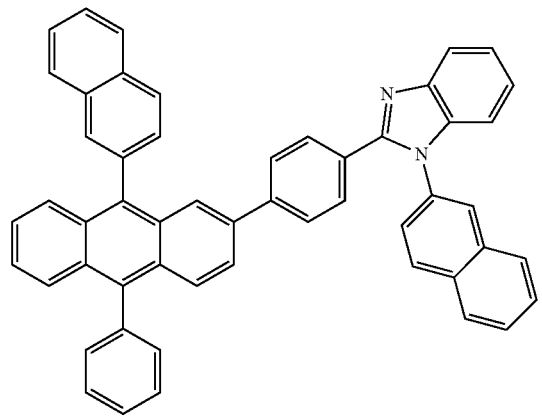
[Chemical Formula 116]
(3b-7)
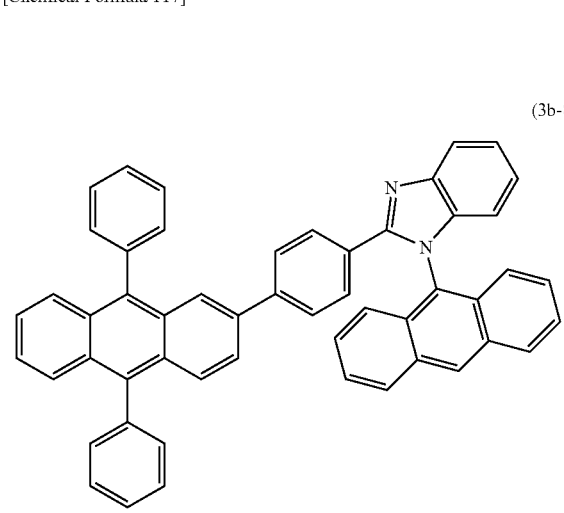
[Chemical Formula 117]
(3b-8)
[Chemical Formula 118]
(3b-9)
[Chemical Formula 119]
(3b-10)
[Chemical Formula 120]
(3b-11)
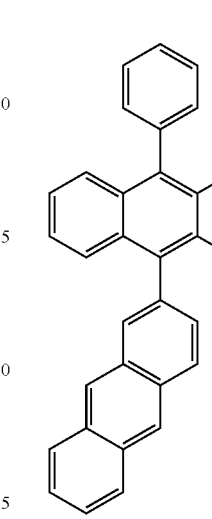

[Chemical Formula 121]

(3b-12)

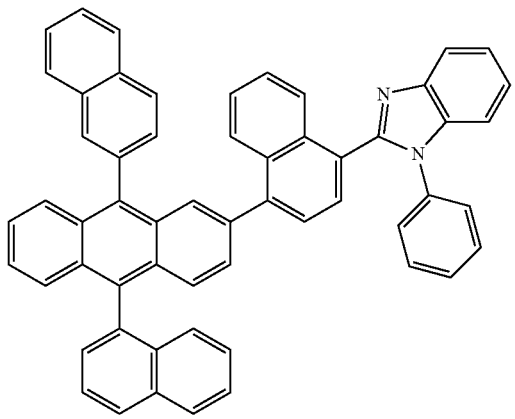

[Chemical Formula 122]

(3b-13)

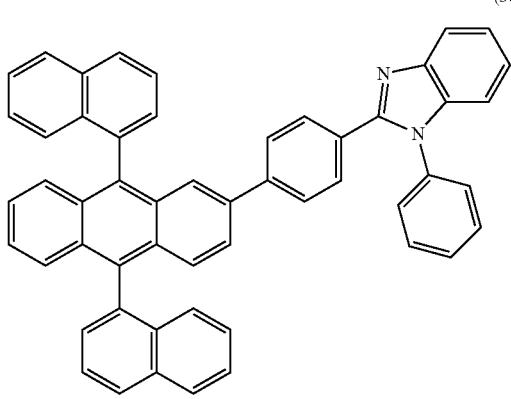

[Chemical Formula 123]

(3b-14)

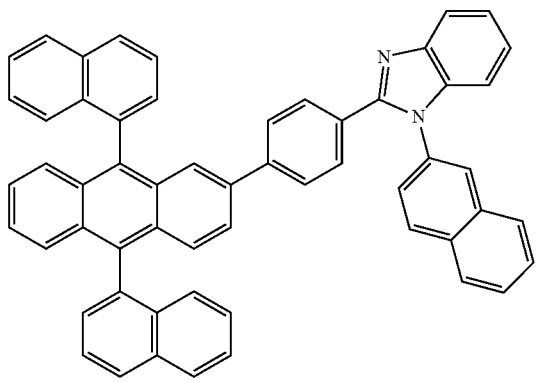

[Chemical Formula 124]

(3b-15)

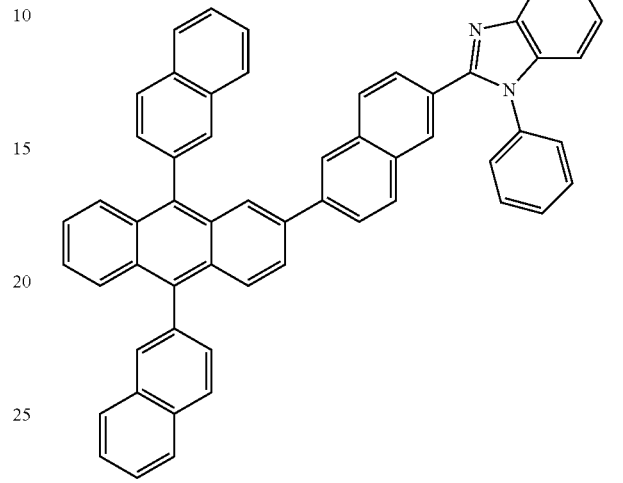

[Chemical Formula 125]

(3b-16)

The following presents specific examples of preferred compounds among the compounds of the general formula (3c) having an anthracene ring structure and preferably used in the organic EL device of the present invention. The present invention, however, is not restricted to these compounds.

[Chemical Formula 126]
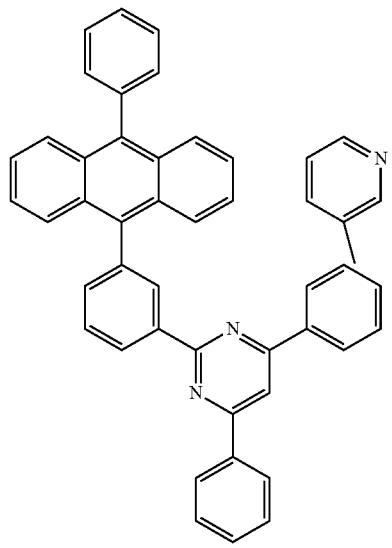
(3c-1)
[Chemical Formula 127]
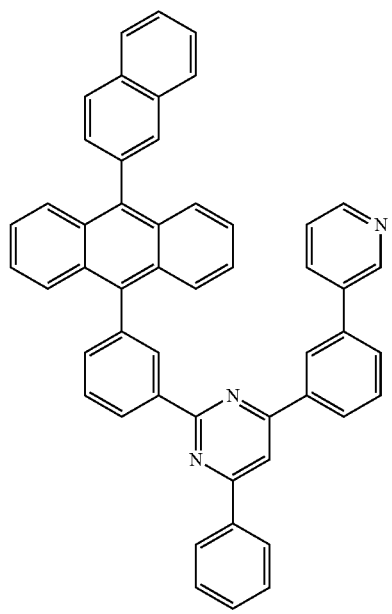
(3c-2)
[Chemical Formula 128]
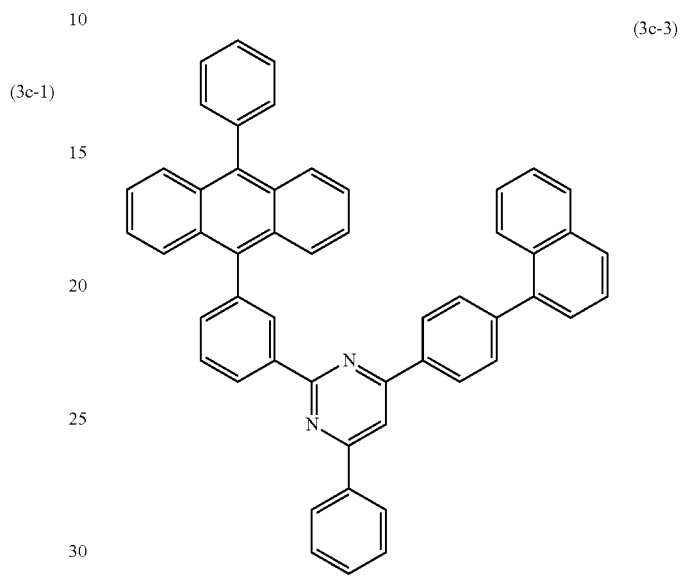
(3c-3)
[Chemical Formula 129]
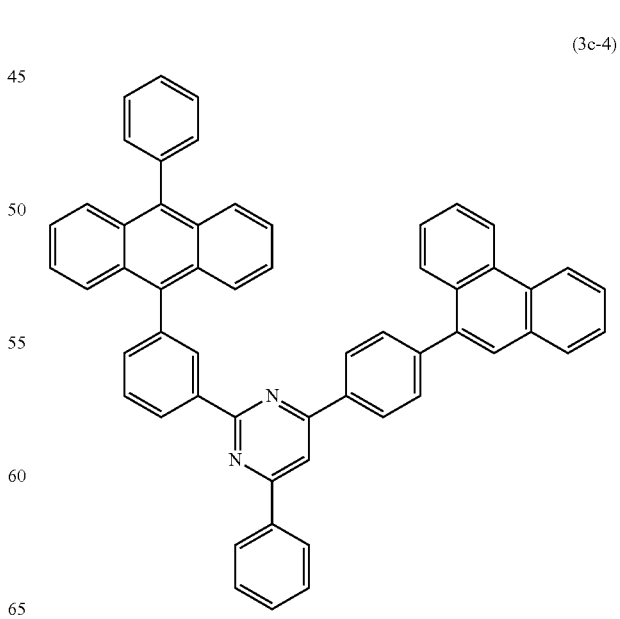
(3c-4)

[Chemical Formula 130]
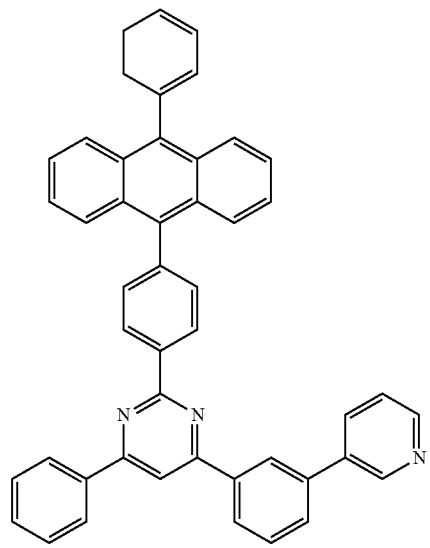
(3c-5)
[Chemical Formula 131]
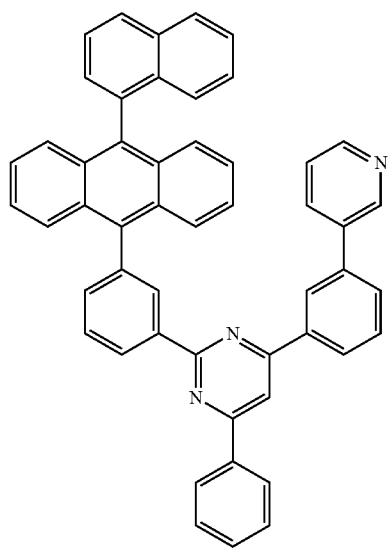
(3c-6)
[Chemical Formula 132]
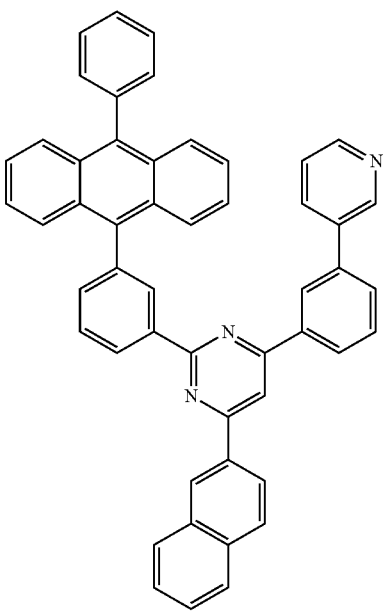
(3c-7)
[Chemical Formula 133]
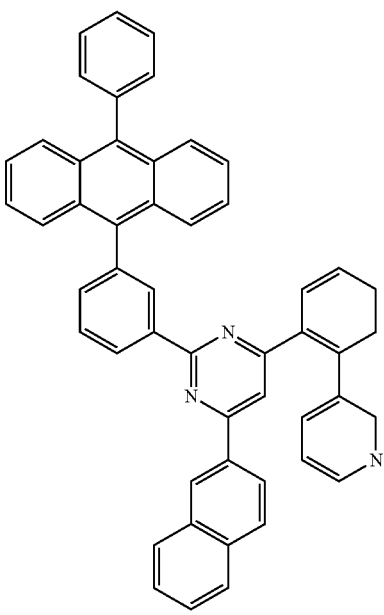
(3c-8)

[Chemical Formula 134]
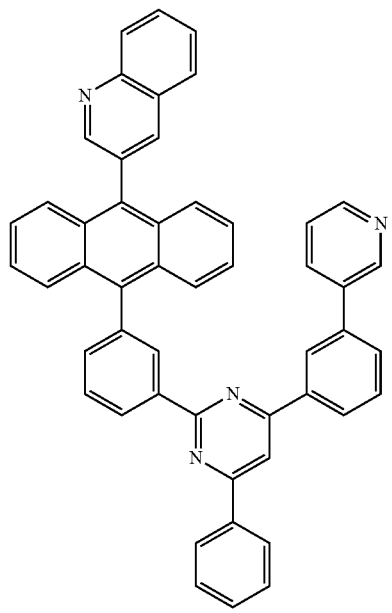
(3c-9)
[Chemical Formula 135]
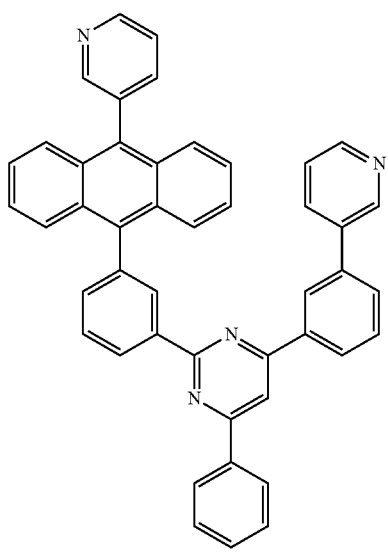
(3c-10)
[Chemical Formula 136]
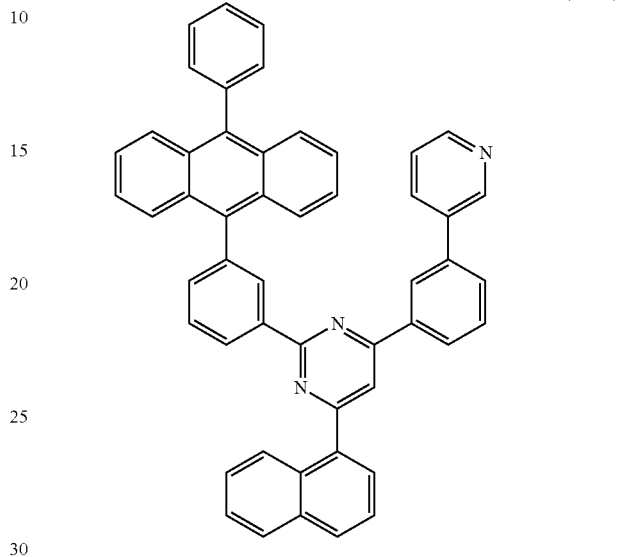
(3c-11)
[Chemical Formula 137]
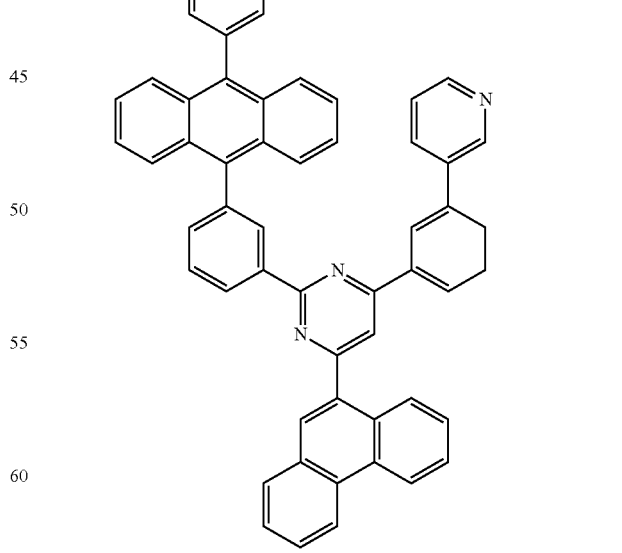
(3c-12)

[Chemical Formula 138]
(3c-13)
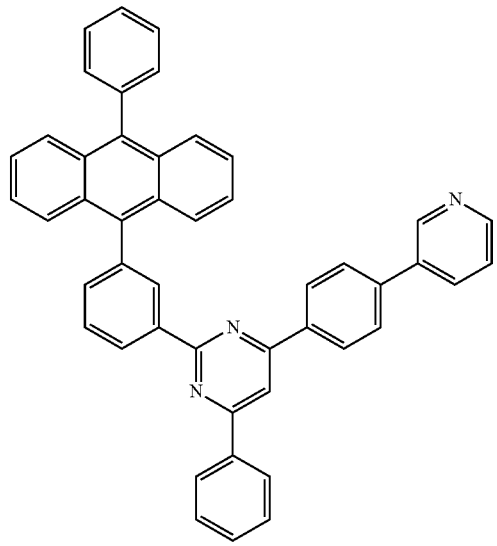
[Chemical Formula 139]
(3c-14)
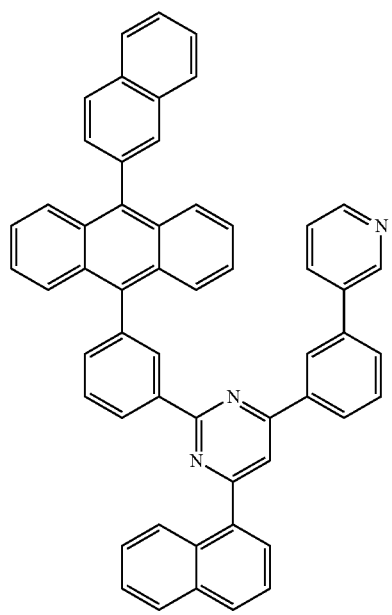
[Chemical Formula 140]
(3c-15)
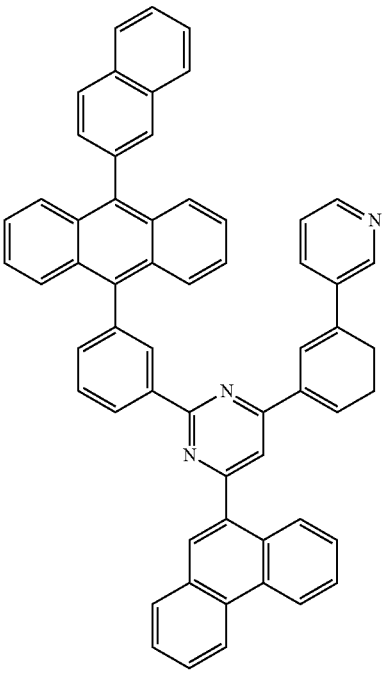
[Chemical Formula 141]
(3c-16)
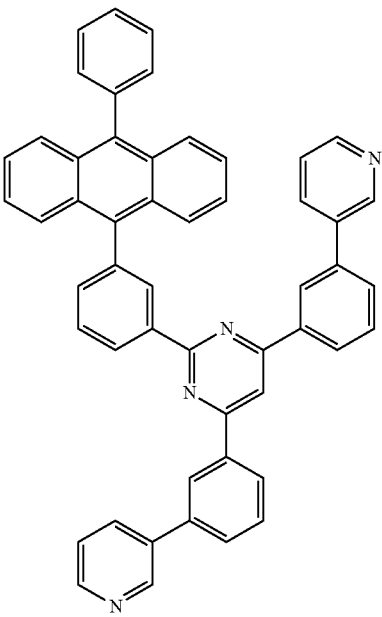

[Chemical Formula 142]
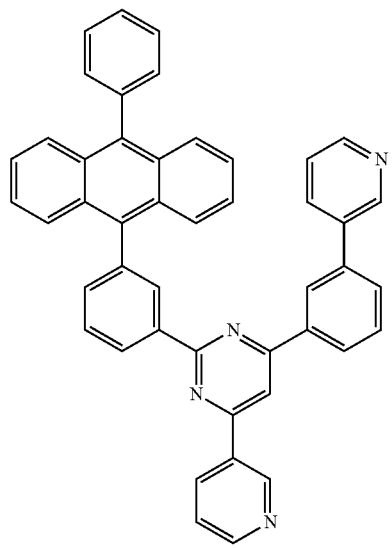
(3c-17)
[Chemical Formula 143]
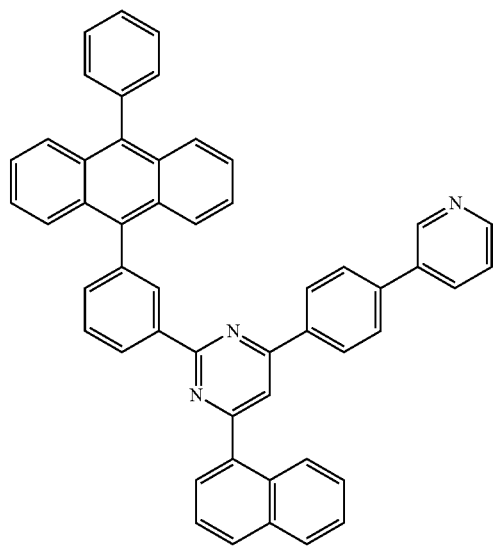
(3c-18)
[Chemical Formula 144]
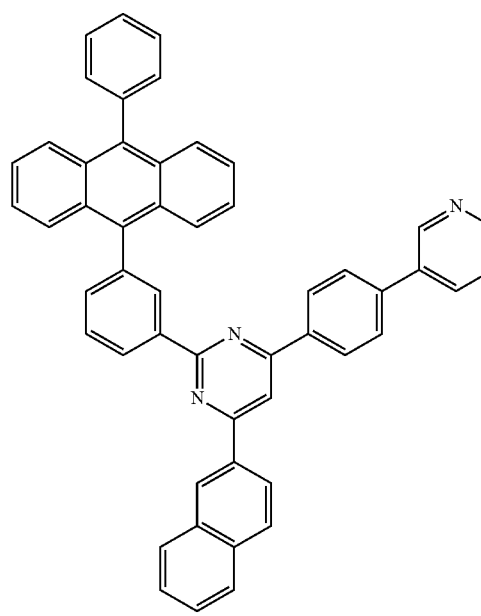
(3c-19)
[Chemical Formula 145]
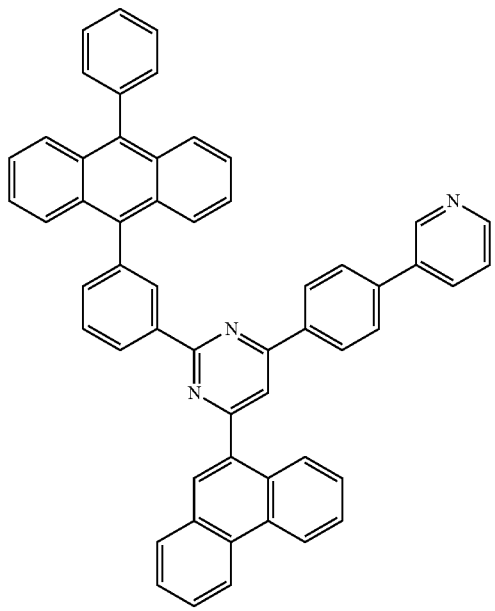
(3c-20)

[Chemical Formula 146]
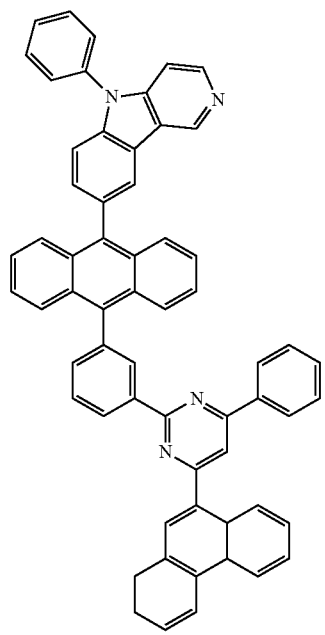
(3c-21)
[Chemical Formula 147]
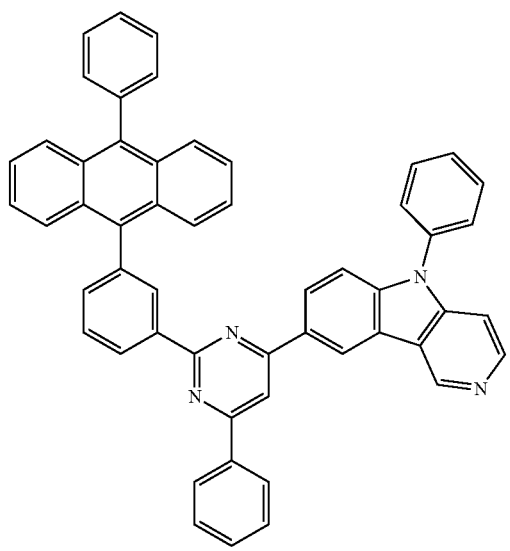
(3c-22)
[Chemical Formula 148]
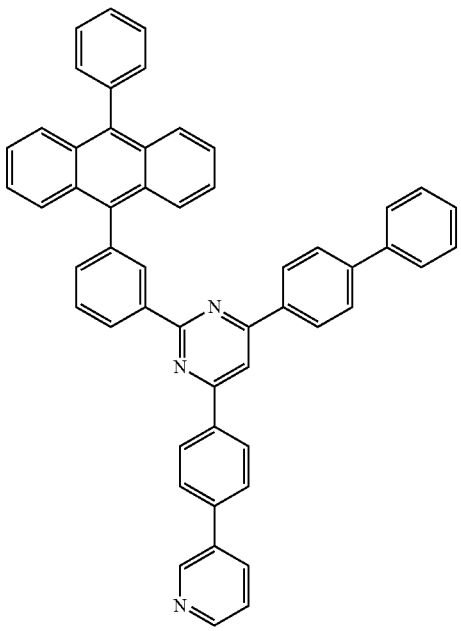
(3c-23)
[Chemical Formula 149]
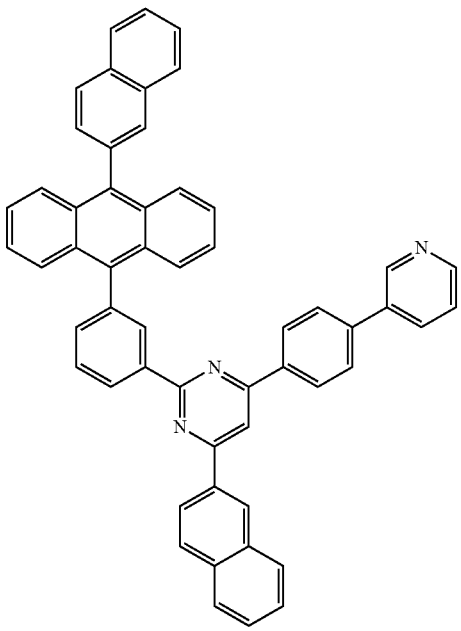
(3c-24)

[Chemical Formula 150]
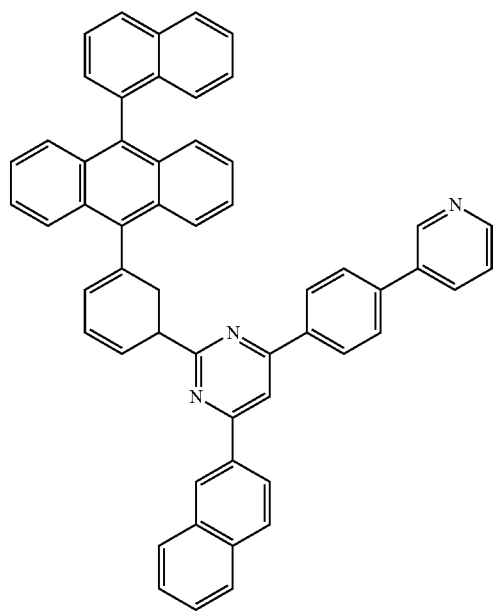
(3c-25)
[Chemical Formula 151]
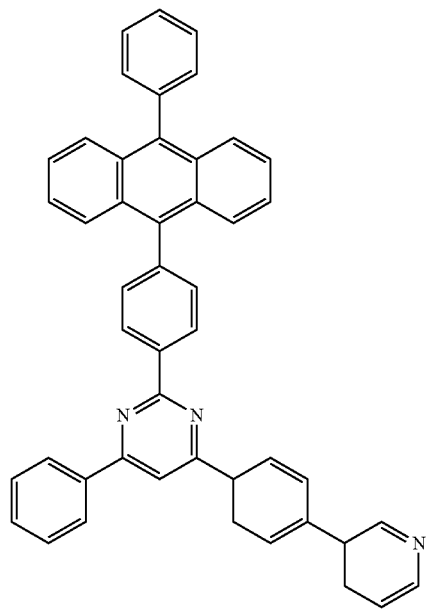
(3c-26)
[Chemical Formula 152]
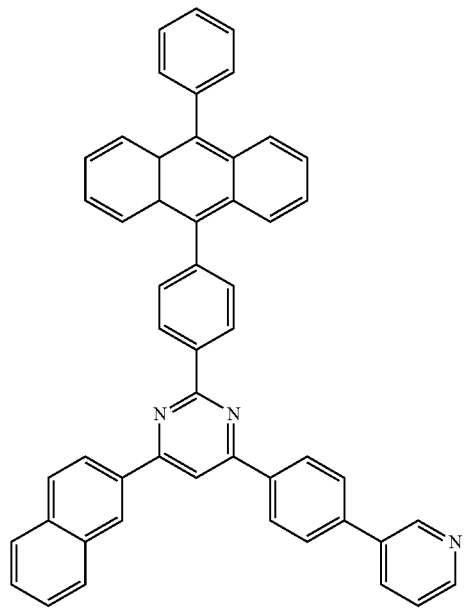
(3c-27)
[Chemical Formula 153]
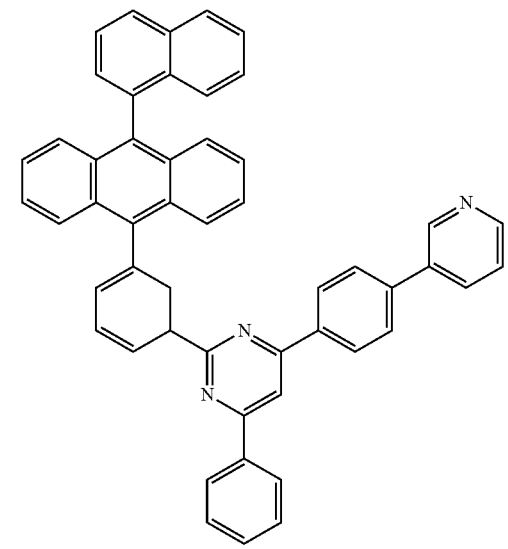
(3c-28)

[Chemical Formula 154]

(3c-29)

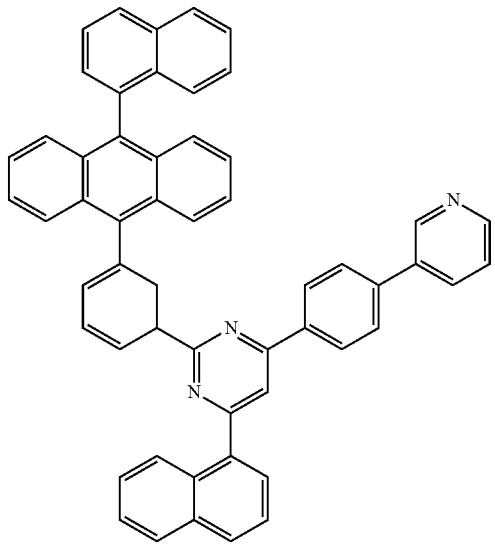

[Chemical Formula 155]

(3c-30)

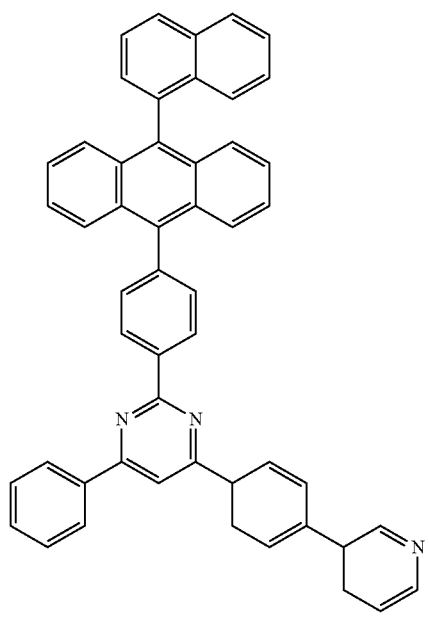

[Chemical Formula 156]

(4-1)

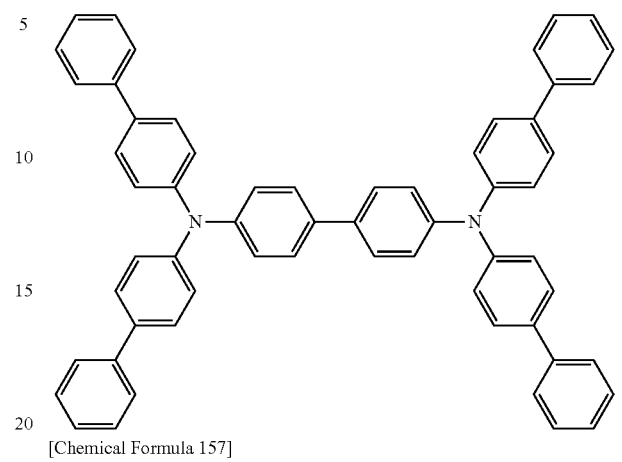

[Chemical Formula 157]

(4-2)

[Chemical Formula 158]

(4-3)

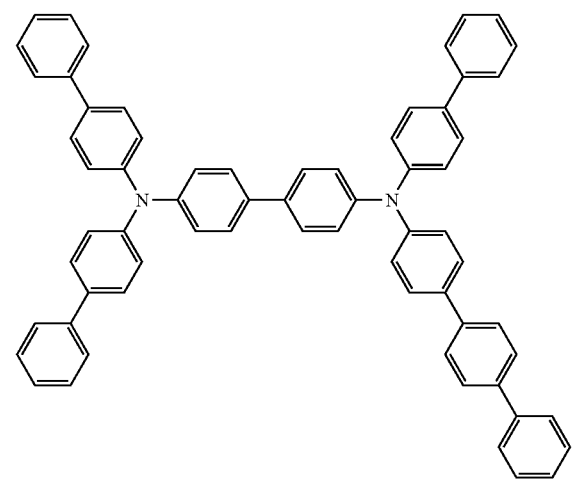

The compounds described above having an anthracene ring structure can be synthesized by a known method (refer to Patent Documents 6 to 8, for example).

In the organic EL device of the present invention, the following presents specific examples of preferred compounds among the arylamine compounds of the general formula (4) having two triphenylamine structures within a molecule and preferably used in the first hole transport layer in the case where the hole transport layer has a two-layer structure of the first hole transport layer and the second hole transport layer. The present invention, however, is not restricted to these compounds.

[Chemical Formula 159]
(4-4)
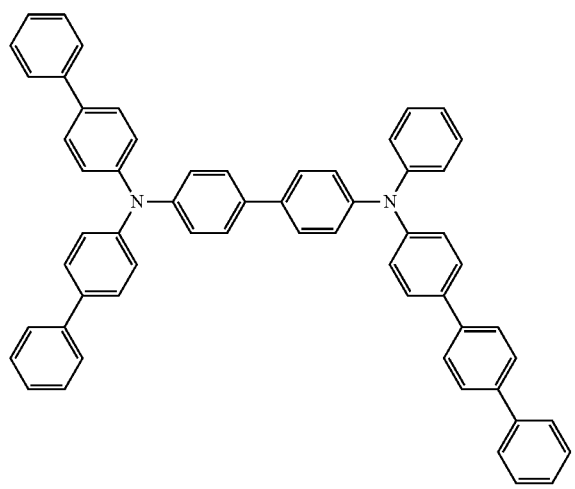
[Chemical Formula 160]
(4-5)
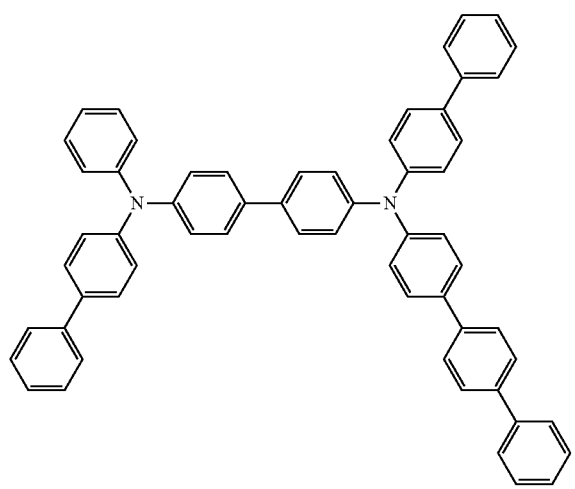
[Chemical Formula 161]
(4-6)
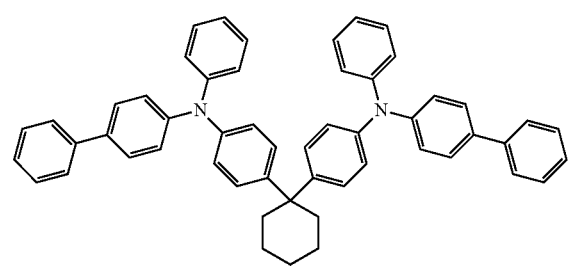
[Chemical Formula 162]
(4-7)
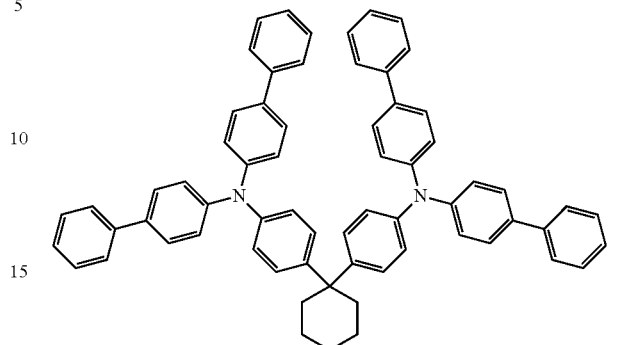
[Chemical Formula 163]
(4-8)
[Chemical Formula 164]
(4-9)
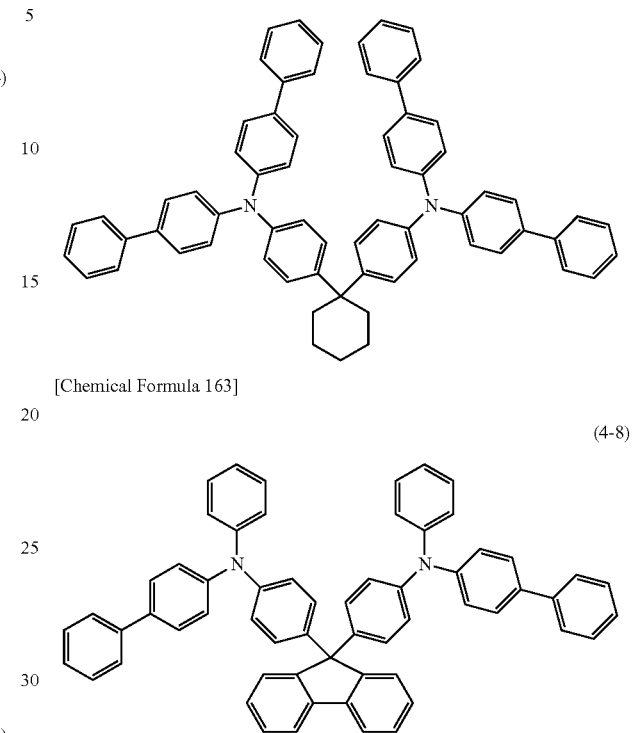
[Chemical Formula 165]
(4-10)
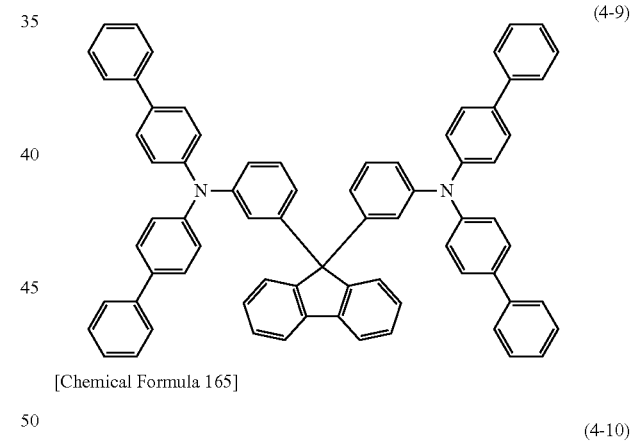

[Chemical Formula 166]
(4-11)
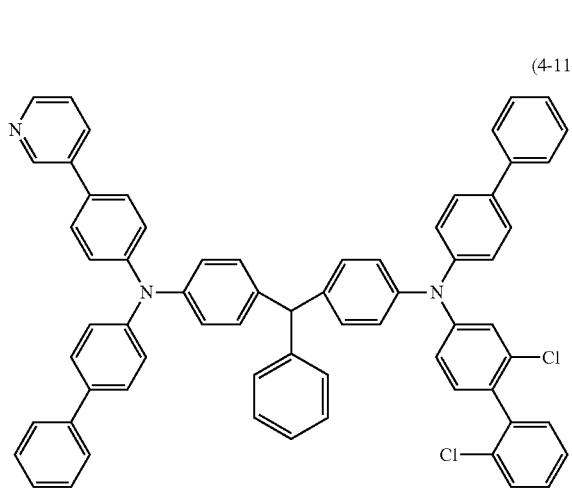
[Chemical Formula 167]
(4-12)
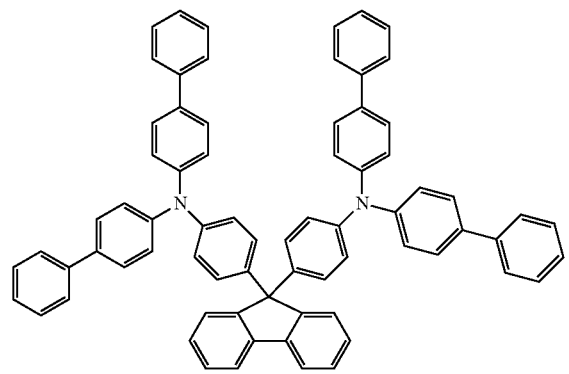
[Chemical Formula 168]
(4-13)
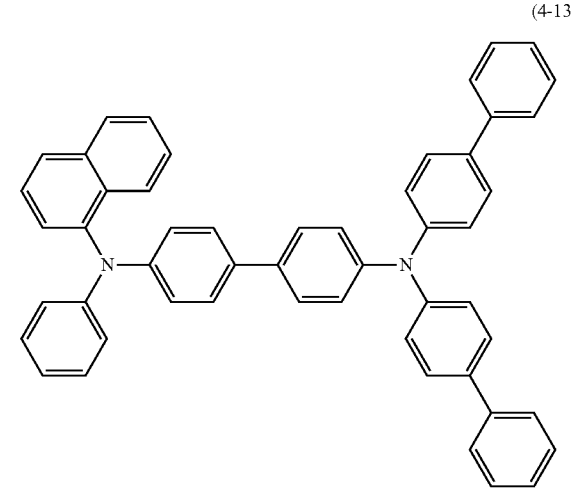
[Chemical Formula 169]
(4-14)
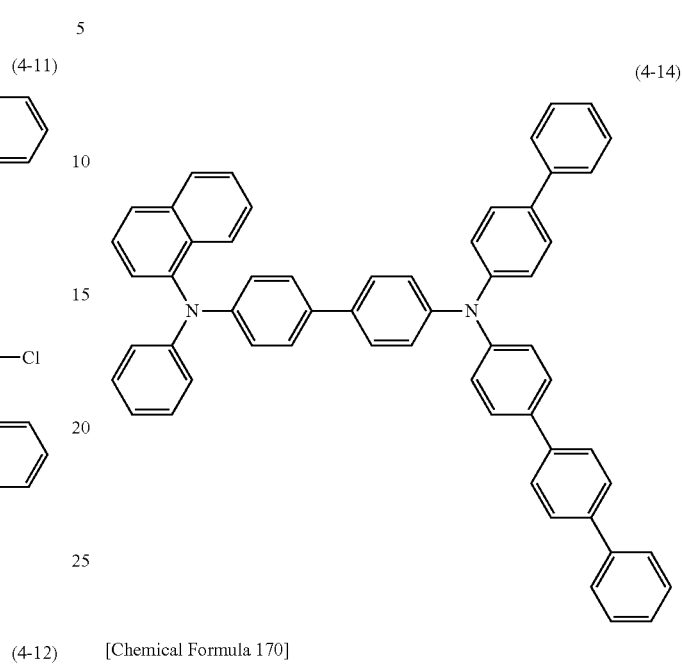
[Chemical Formula 170]
(4-15)
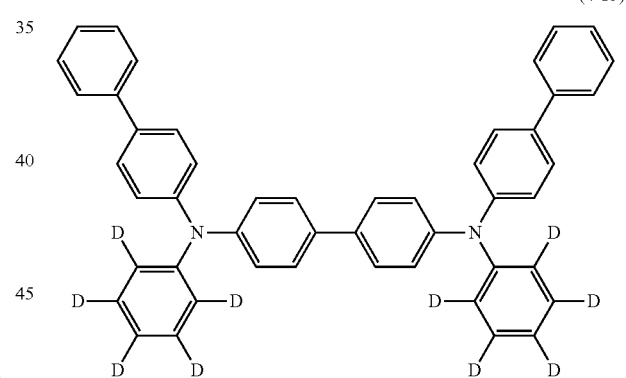
[Chemical Formula 171]
(4-16)
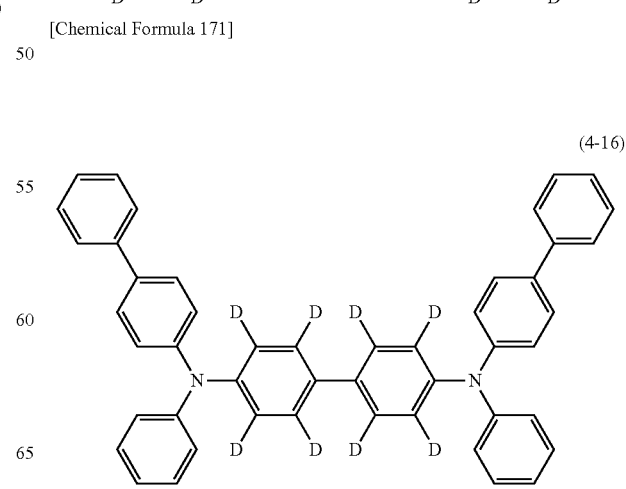

[Chemical Formula 172]
(4-17)
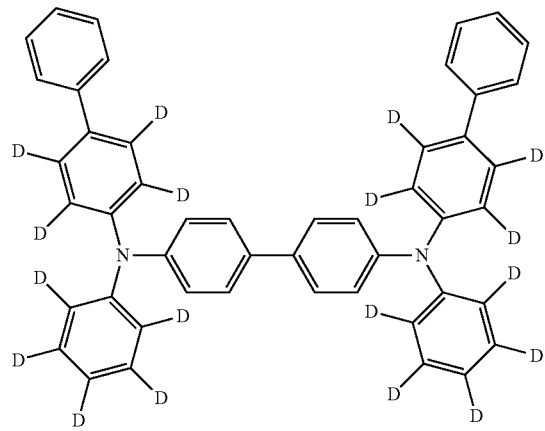
[Chemical Formula 173]
(4-18)
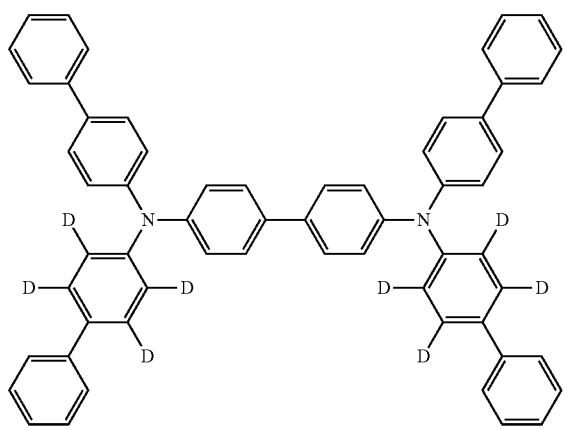
[Chemical Formula 174]
(4-19)
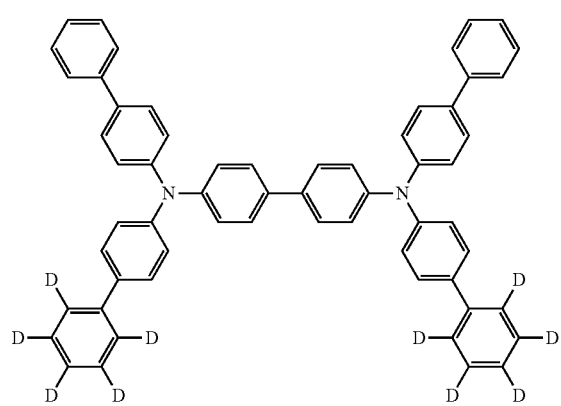
[Chemical Formula 175]
(4-20)
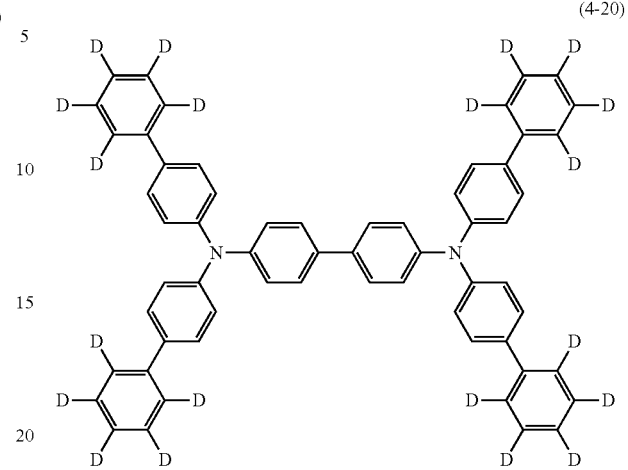
[Chemical Formula 176]
(4-21)
[Chemical Formula 177]
(4-22)
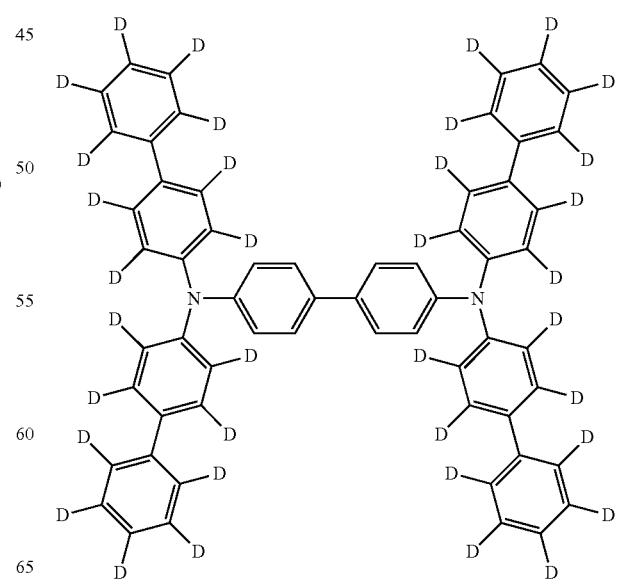

-continued

[Chemical Formula 178]

(4-23)

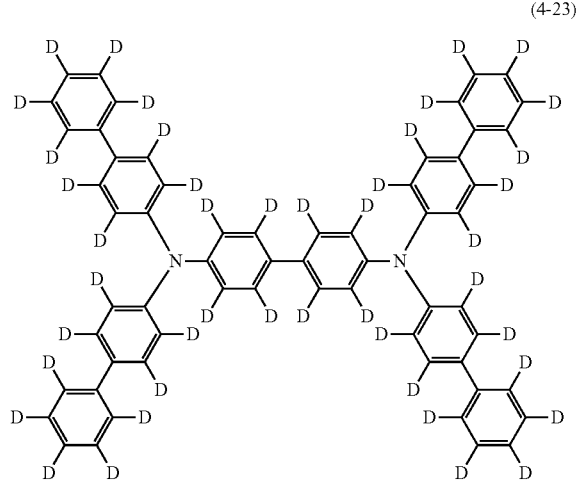

[Chemical Formula 179]

(4'-1)

[Chemical Formula 180]

(4'-2)

In the organic EL device of the present invention, the following presents specific examples of preferred compounds in the arylamine compounds preferably used in the first hole transport layer and having two triphenylamine structures within a molecule in the arylamine compounds having a structure in which two to six triphenylamine structures are joined within a molecule via a single bond or a divalent group that does not contain a heteroatom in the case where the hole transport layer has a two-layer structure of the first hole transport layer and the second hole transport layer, besides the arylamine compounds of the general formula (4) having two triphenylamine structures within a molecule. The present invention, however, is not restricted to these compounds.

In the organic EL device of the present invention, the following presents specific examples of preferred compounds among the arylamine compounds of the general formula (5) having four triphenylamine structures within a molecule and preferably used in the first hole transport layer in the case where the hole transport layer has a two-layer structure of the first hole transport layer and the second hole transport layer. The present invention, however, is not restricted to these compounds.

[Chemical Formula 181]

(5-1)

[Chemical Formula 182]
(5-2)
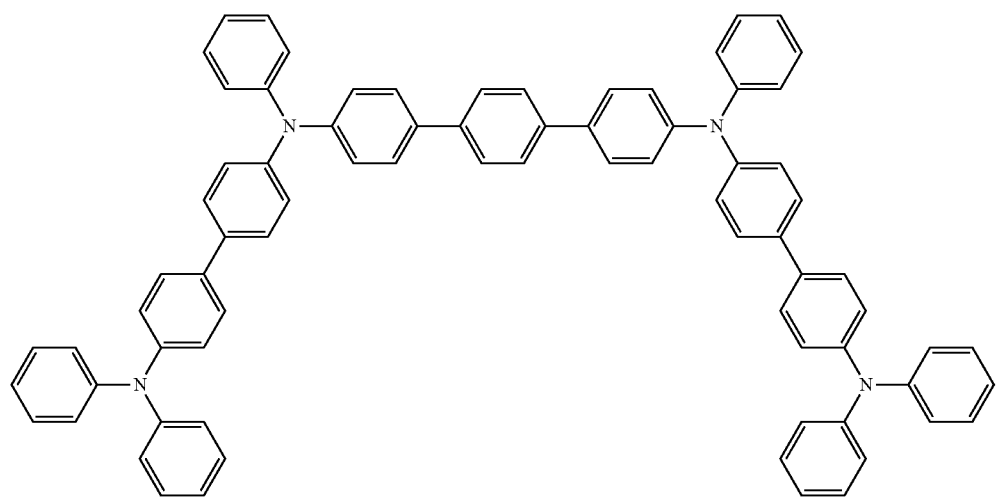
[Chemical Formula 183]
(5-3)
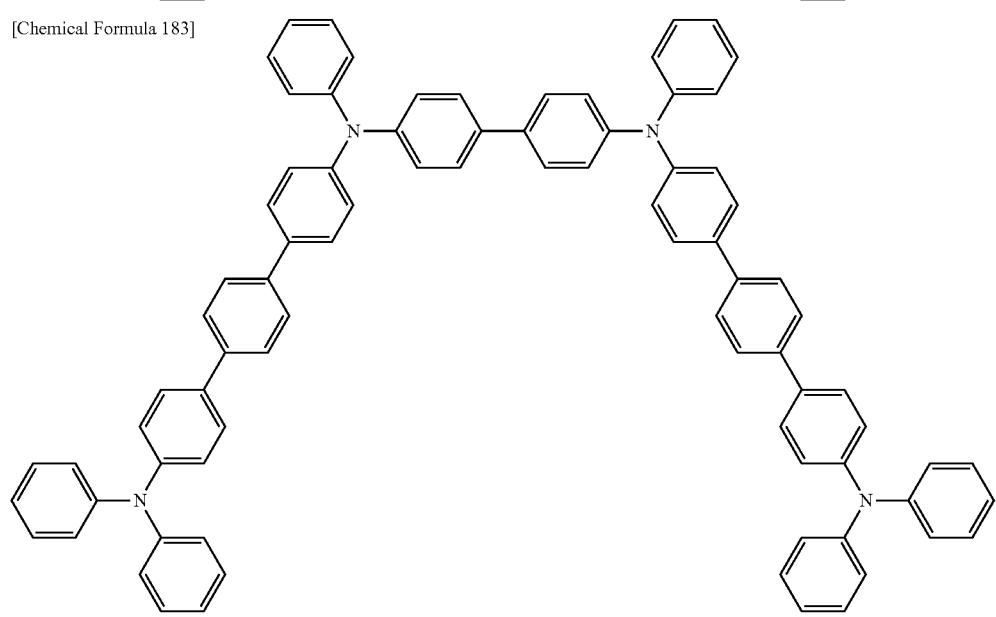
[Chemical Formula 184]
(5-4)
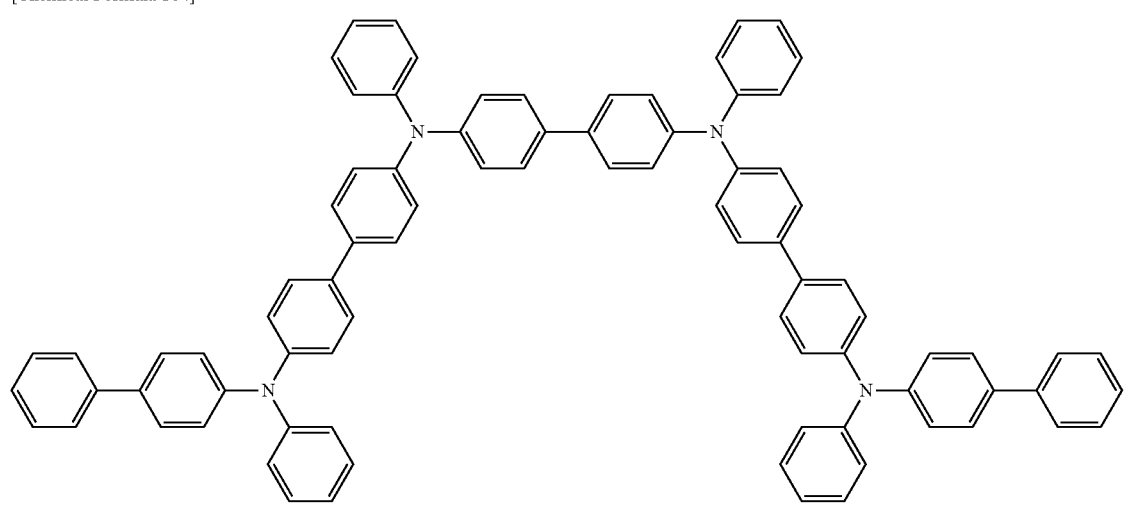

[Chemical Formula 185]
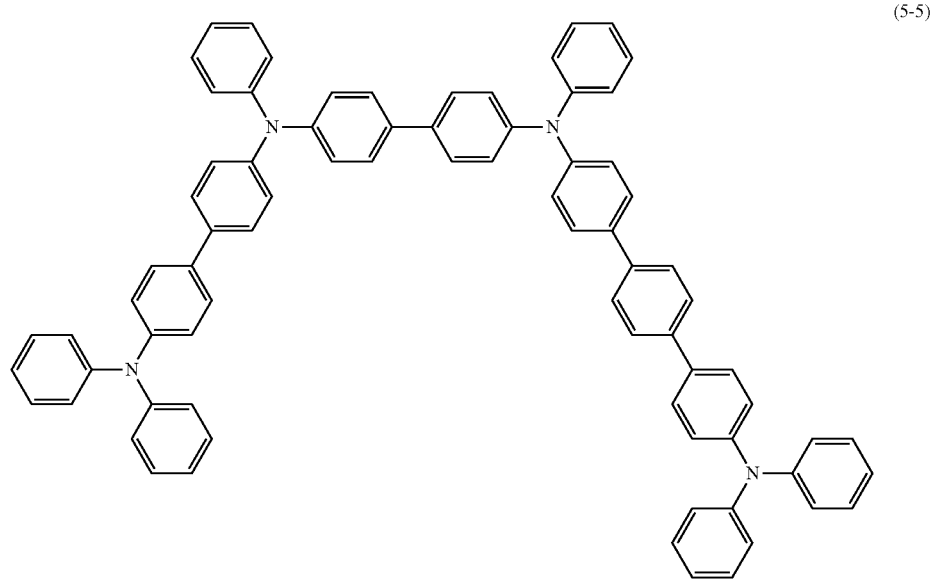
(5-5)
[Chemical Formula 186]
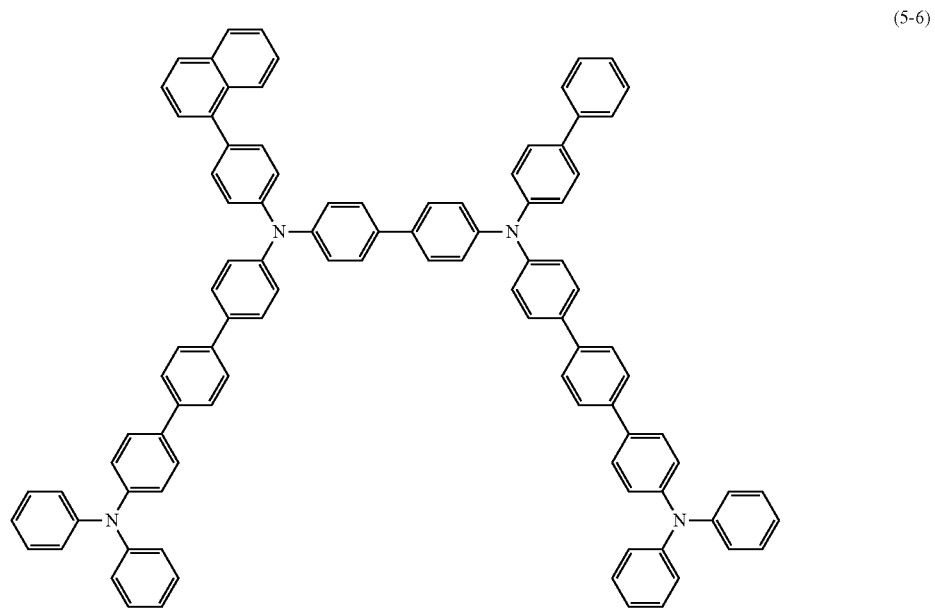
(5-6)

[Chemical Formula 187]
(5-7)
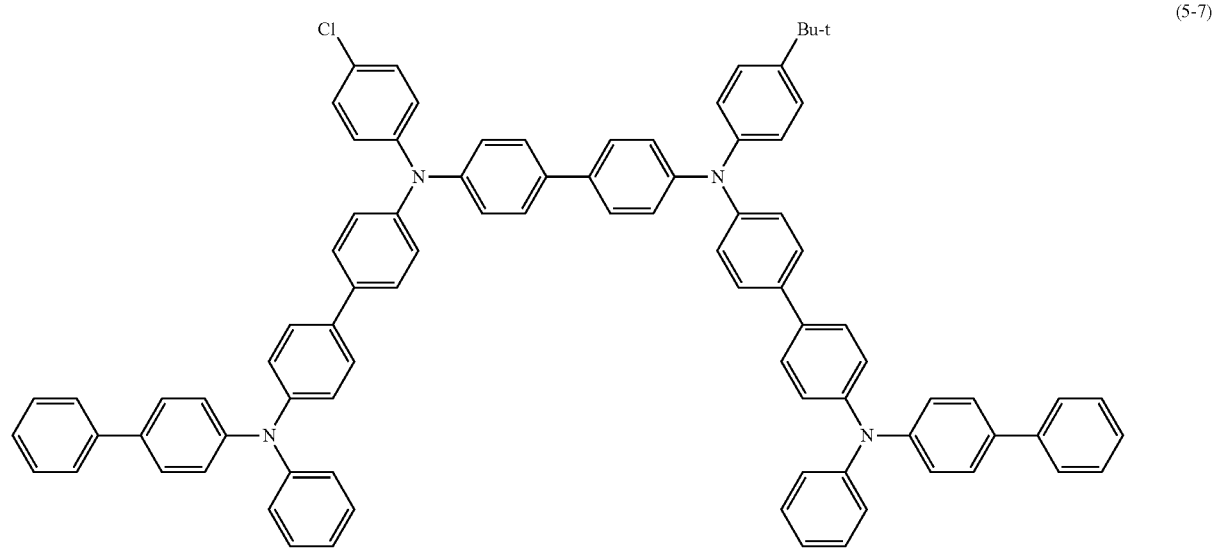
[Chemical Formula 188]
(5-8)
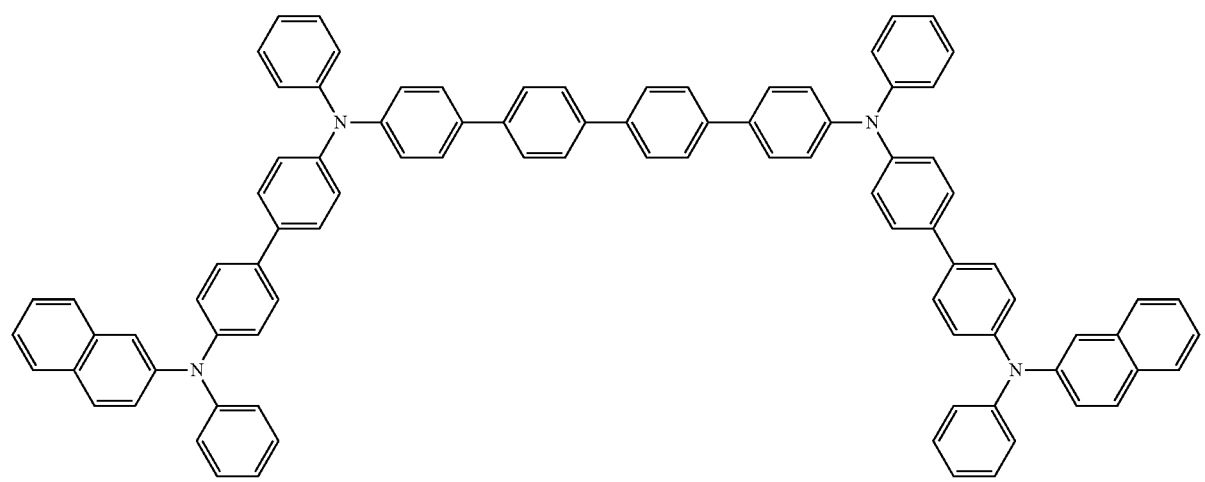
[Chemical Formula 189]
(5-9)
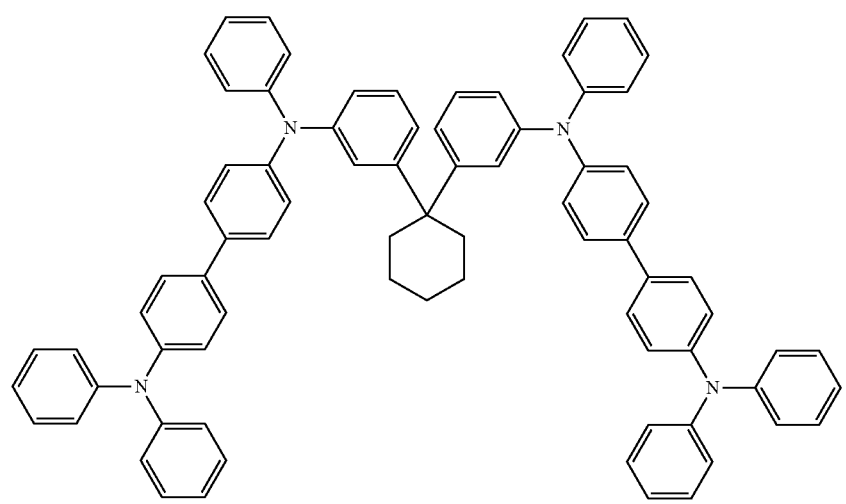

[Chemical Formula 190]
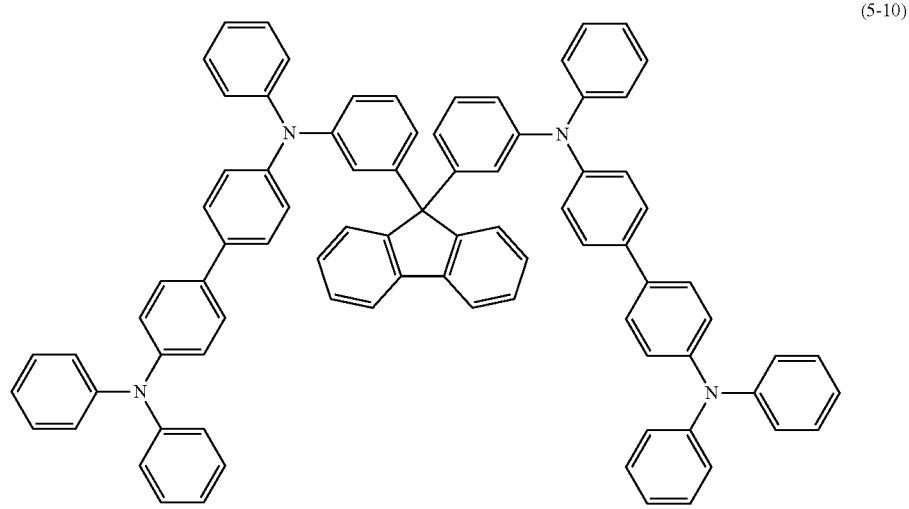
(5-10)
[Chemical Formula 191]
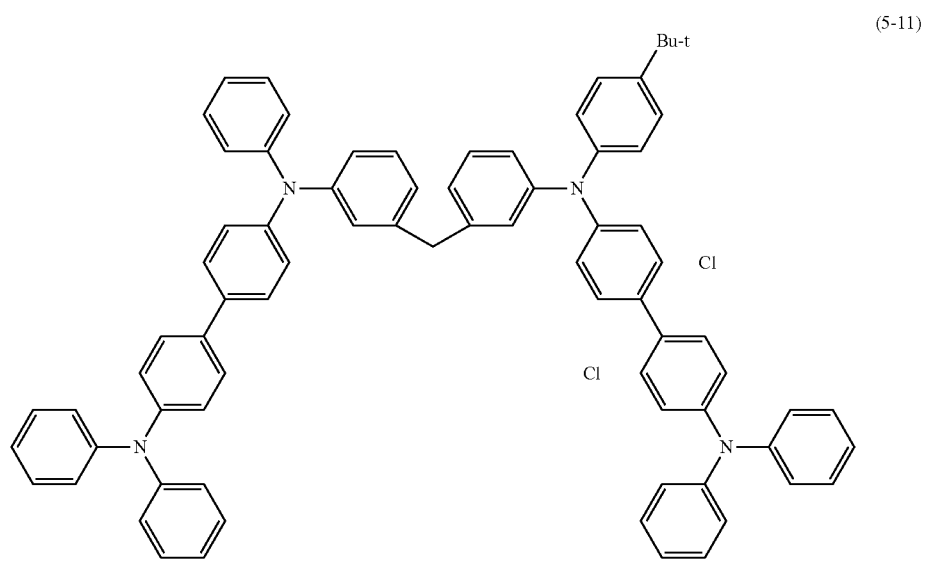
(5-11)

[Chemical Formula 192]
(5-12)
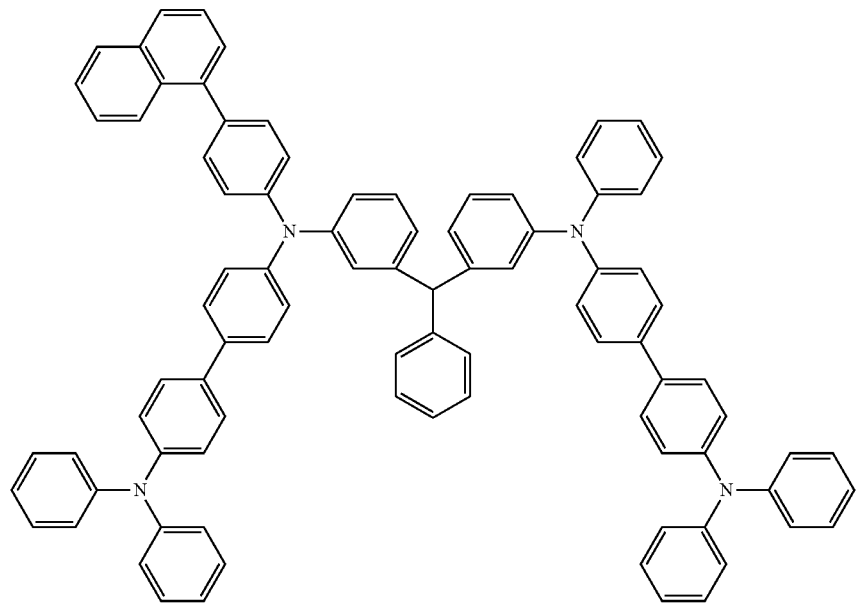
[Chemical Formula 193]
(5-13)
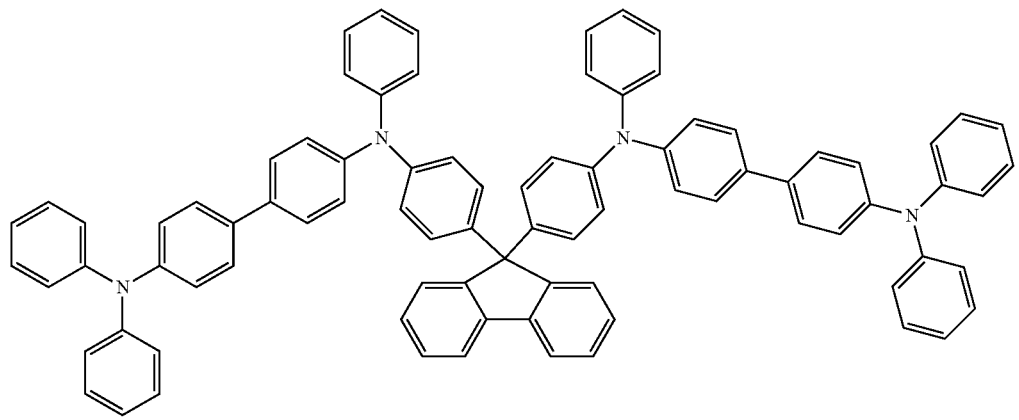
[Chemical Formula 194]
(5-14)
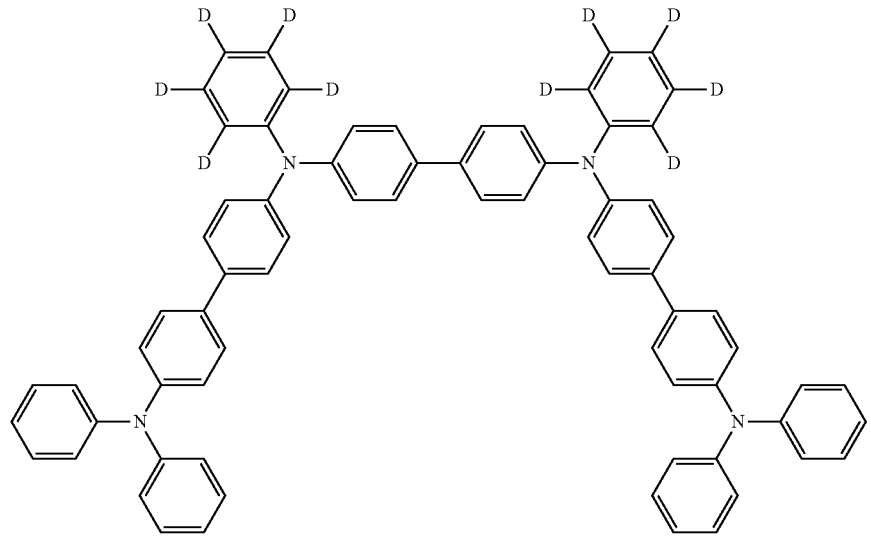

[Chemical Formula 195]
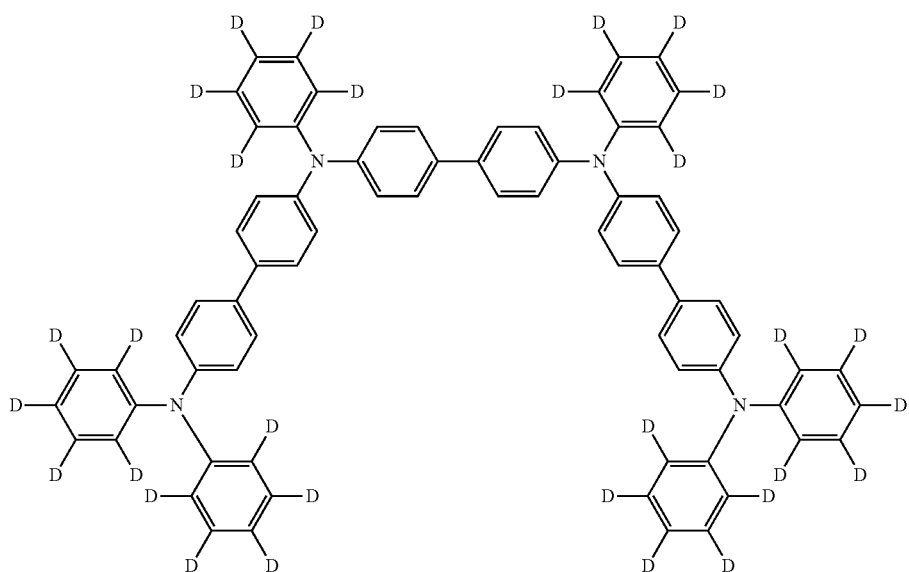
5-15
[Chemical Formula 195]
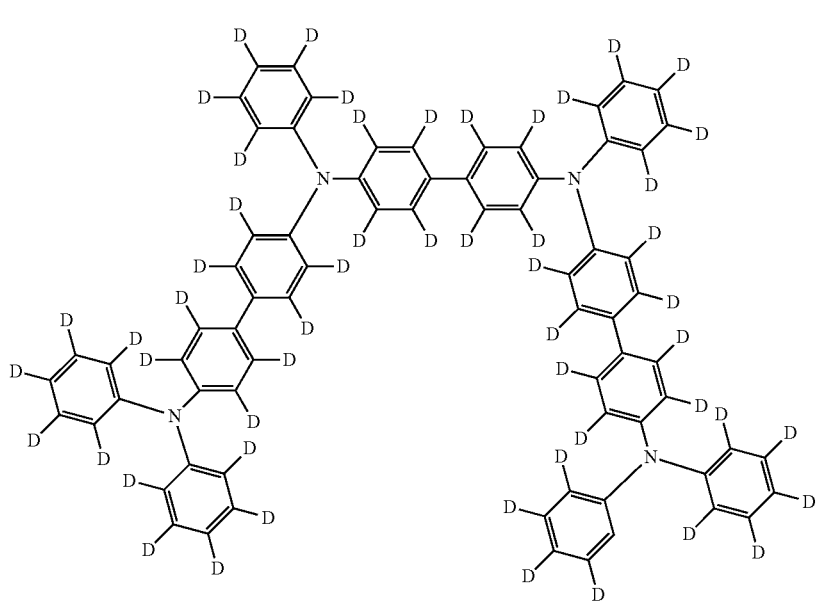
5-16

[Chemical Formula 197] (5-17)

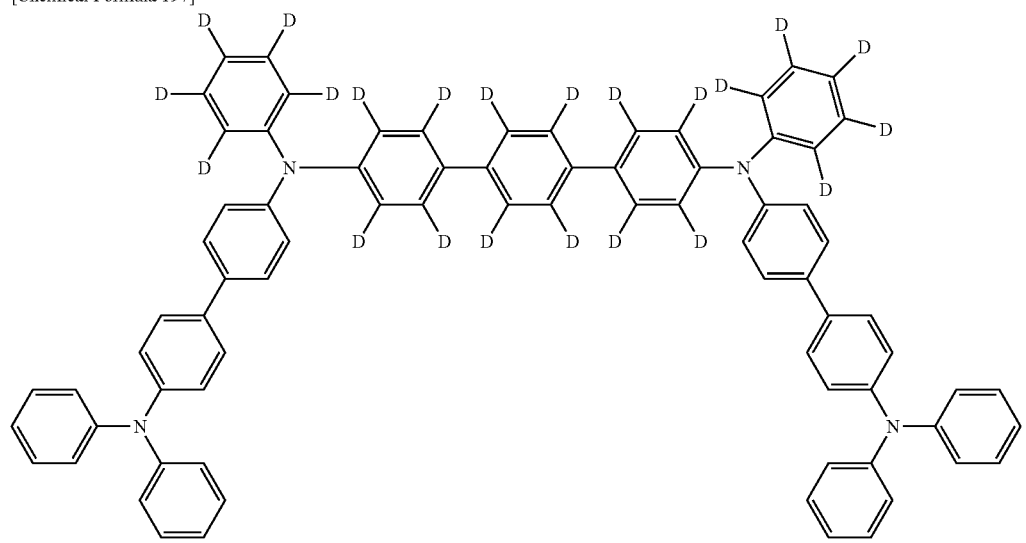

The arylamine compounds of the general formula (4) having two triphenylamine structures within a molecule and the arylamine compounds of the general formula (5) having four triphenylamine structures within a molecule can be synthesized by a known method (refer to Patent Documents 9 to 11, for example).

The arylamine compounds of the general formula (1) were purified by methods such as column chromatography; adsorption using, for example, a silica gel, activated carbon, or activated clay; recrystallization or crystallization using a solvent; and sublimation. The compounds were identified by an NMR analysis. A glass transition point (Tg) and a work function were measured as material property values. The glass transition point (Tg) can be used as an index of stability in a thin-film state, and the work function can be used as an index of hole transportability.

Other compounds used for the organic EL device of the present invention were purified by methods such as column chromatography; adsorption using, for example, a silica gel, activated carbon, or activated clay; and recrystallization or crystallization using a solvent; and finally purified by sublimation.

The glass transition point (Tg) was measured by a high-sensitive differential scanning calorimeter (DSC3100S produced by Bruker AXS) using powder.

For the measurement of the work function, a 100 nm-thick thin film was fabricated on an ITO substrate, and an ionization potential measuring device (PYS-202 produced by Sumitomo Heavy Industries, Ltd.) was used.

The organic EL device of the present invention may have a structure including an anode, a hole injection layer, a hole transport layer, a light emitting layer, an electron transport layer, and a cathode successively formed on a substrate, optionally with an electron blocking layer between the hole transport layer and the light emitting layer, a hole blocking layer between the light emitting layer and the electron transport layer, and an electron injection layer between the electron transport layer and the cathode. Some of the organic layers in the multilayer structure may be omitted, or may serve more than one function. For example, a single organic layer may serve as the hole injection layer and the hole transport layer, or as the electron injection layer and the electron transport layer. Further, the organic layers having a same function may have a laminate structure of two or more layers, for example, the hole transport layer may have a two-layer structure, the light emitting layer may have a two-layer structure, or the electron transport layer may have a two-layer structure. The organic EL device of the present invention preferably also has a two-layer structure of a first hole transport layer and a second hole transport layer.

Electrode materials with high work functions such as ITO and gold are used as the anode of the organic EL device of the present invention. The hole injection layer of the organic EL device of the present invention may be made of, for example, material such as starburst-type triphenylamine derivatives and various triphenylamine tetramers; porphyrin compounds as represented by copper phthalocyanine; accepting heterocyclic compounds such as hexacyano azatriphenylene; and coating-type polymer materials, in addition to the arylamine compounds of the general formula (1). These materials may be formed into a thin film by a vapor deposition method or other known methods such as a spin coating method and an inkjet method.

The arylamine compounds of the general formula (1) are used as the hole transport layer of the organic EL device of the present invention. These may be individually deposited for film forming, may be used as a single layer deposited mixed with other hole transporting materials, or may be formed as a laminate of individually deposited layers, a laminate of mixedly deposited layers, or a laminate of the individually deposited layer and the mixedly deposited layer. These materials may be formed into a thin-film by a vapor deposition method or other known methods such as a spin coating method and an inkjet method.

Examples of a hole transporting material that can be mixed or can be used at the same time with the arylamine compounds of the general formula (1) can be benzidine derivatives such as N,N'-diphenyl-N,N'-di(m-tolyl)benzidine (TPD), N,N'-diphenyl-N,N'-di(α-naphthyl)benzidine (NPD), and N,N,N',N'-tetrabiphenylylbenzidine; 1,1-bis[4-(di-4-tolylamino)phenyl]cyclohexane (TAPC); arylamine compounds having a structure in which two triphenylamine structures are joined within a molecule via a single bond or a divalent group that does not contain a heteroatom such as the arylamine compounds of the general formula (4); arylamine compounds having a structure in which four triphenylamine structures are joined within a molecule via a single bond or a divalent group that does not contain a heteroatom such as the arylamine compounds of the general formula (5); and various triphenylamine trimers.

The material used for the hole injection layer or the hole transport layer may be obtained by p-doping materials such as trisbromophenylamine hexachloroantimony, and radialene derivatives (refer to WO2014/009310, for example) into a material commonly used for these layers, or may be, for example, polymer compounds each having, as a part of the compound structure, a structure of a benzidine derivative such as TPD.

In the case where the hole transport layer of the organic EL device of the present invention has a two-layer structure, the above hole transporting materials are used as the first hole transport layer, in addition to the arylamine compounds of the general formula (4) having two triphenylamine structures within a molecule and the arylamine compounds of the general formula (5) having four triphenylamine structures within a molecule.

The hole transporting materials are used as the second hole transport layer in addition to the arylamine compounds of the general formula (1).

Examples of material used for the electron blocking layer of the organic EL device of the present invention can be compounds having an electron blocking effect, including, for example, carbazole derivatives such as 4,4',4''-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene, in addition to the arylamine compounds of the general formula (1). These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the light emitting layer of the organic EL device of the present invention can be various metal complexes including, for example, quinolinol derivative metal complexes such as $Alq_3$; anthracene derivatives; bis(styryl)benzene derivatives; pyrene derivatives; oxazole derivatives; and polyparaphenylene vinylene derivatives; in addition to the amine derivatives of the general formula (2) having a condensed ring structure. Further, the light emitting layer may be made of a host material and a dopant material. Examples of the host material can be thiazole derivatives, benzimidazole derivatives, and polydialkyl fluorene derivatives, in addition to the above light-emitting materials. Examples of the dopant material can be quinacridone, coumarin, rubrene, perylene, pyrene, derivatives thereof, benzopyran derivatives, indenophenanthrene derivatives, rhodamine derivatives, and aminostyryl derivatives in addition to the amine derivatives of the general formula (2) having a condensed ring structure. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

The dopant material in the light emitting layer of the organic EL device of the present invention is preferably the amine derivatives of the general formula (2) having a condensed ring structure.

Further, the light-emitting material may be a phosphorescent material. Phosphorescent materials as metal complexes of metals such as iridium and platinum may be used. Examples of the phosphorescent materials include green phosphorescent materials such as $Ir(ppy)_3$, blue phosphorescent materials such as FIrpic and FIr6, and red phosphorescent materials such as $Btp_2Ir(acac)$. Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2) and 2,2',2''-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, Examples of the light-emitting material may be delayed fluorescent-emitting material such as a CDCB derivative of PIC-TRZ, CC2TA, PXZ-TRZ, 4CzIPN or the like (refer to Non-Patent Document 3, for example).

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproin (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Material used for the electron transport layer of the organic EL device of the present invention can be the compounds of the general formula (3) having an anthracene ring structure, far preferably, the compounds of the general formulas (3a), (3b) or (3c) having an anthracene ring structure. These may be individually deposited for film forming, may be used as a single layer deposited mixed with other electron transporting materials, or may be formed as a laminate of individually deposited layers, a laminate of mixedly deposited layers, or a laminate of the individually deposited layer and the mixedly deposited layer. These materials may be formed into a thin film by a vapor deposition method or other known methods such as a spin coating method and an inkjet method.

Examples of the hole transporting material that can be mixed or can be used at the same time with the compounds of the general formula (3) having an anthracene ring structure can be various metal complexes, including, for example, metal complexes of quinolinol derivatives such as Alq$_3$ and BAlq, triazole derivatives, triazine derivatives, oxadiazole derivatives, pyridine derivatives, pyrimidine derivatives, benzimidazole derivatives, thiadiazole derivatives, anthracene derivatives, carbodiimide derivatives, quinoxaline derivatives, pyridoindole derivatives, phenanthroline derivatives, and silole derivatives.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

<Synthesis of 4,4'''-bis{(biphenyl-4-yl)-phenylamino}-(1,1':4',1":4",1'''-quaterphenyl) (Compound 1-1)>

N-phenyl-N-{4-(4,4,5,5-tetramethyl-1,3,2-dioxaborolan-2-yl)phenyl}-(1,1'-biphenyl-4-yl)amine (18.2 g), 4,4'-diiodobiphenyl (7.5 g), a 2 M potassium carbonate aqueous solution (46 ml), toluene (60 ml), and ethanol (15 ml) were added into a nitrogen-substituted reaction vessel and aerated with nitrogen gas for 1 hour. The mixture was heated after adding tetrakis(triphenylphosphine)palladium (1.1 g), and stirred at 72° C. for 10 hours. The mixture was cooled to a room temperature, and methanol (60 ml) was added. A precipitated solid was collected by filtration and washed with a methanol/water (5/1, v/v) mixed solution (100 ml). The solid was dissolved by being heated after adding 1,2-dichlorobenzene (100 ml). The product was left to cool after removing insoluble matter by filtration, and a crude product precipitated by adding methanol (200 ml) was collected by filtration. The crude product was washed under reflux with methanol (100 ml) to obtain a pale yellow powder of 4,4'''-bis{(biphenyl-4-yl)-phenylamino}-(1,1':4', 1":4",1'''-quaterphenyl) (Compound 1-1; 11.8 g; yield 81%).

[Chemical Formula 198]

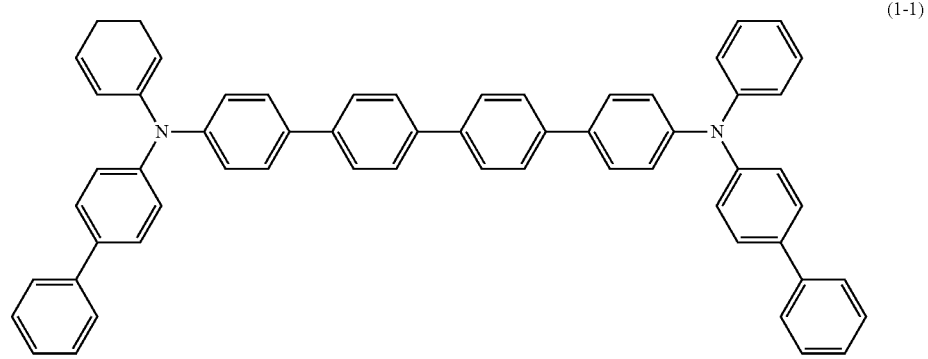

(1-1)

The structure of the obtained pale yellow powder was identified by NMR.

$^1$H-NMR (CDCl$_3$) detected 44 hydrogen signals, as follows.

δ (ppm)=7.66-7.77 (8H), 7.50-7.64 (12H), 7.42-7.50 (4H), 7.28-7.38 (6H), 7.20-7.26 (12H), 7.08 (2H).

Example 2

<Synthesis of 4,4'''-bis{(biphenyl-4-yl)-phenylamino}-(1,1':3',1":3",1'''-quaterphenyl) (Compound 1-11)>

The reaction was carried out under the same conditions as those of Example 1, except that 4,4'-diiodobiphenyl was replaced with 3,3'-dibromobiphenyl. As a result, a pale yellow powder of 4,4'''-bis{(biphenyl-4-yl)-phenylamino}-(1,1':3',1":3",1'''-quaterphenyl) (Compound 1-11; 16.2 g; yield 91%) was obtained.

[Chemical Formula 199]

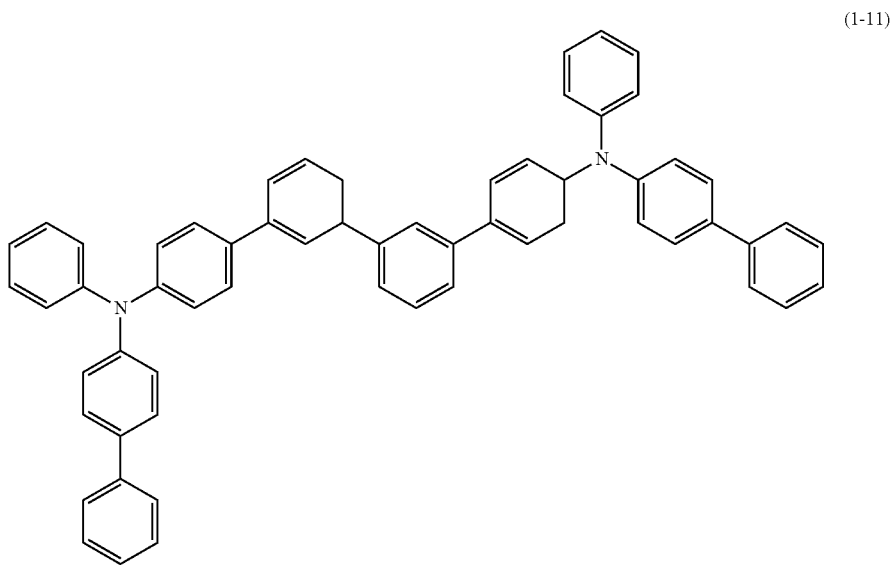

(1-11)

The structure of the obtained pale yellow powder was identified by NMR.

$^1$H-NMR (CDCl$_3$) detected 44 hydrogen signals, as follows.

δ(ppm)=7.87 (2H), 7.48-7.66 (18H), 7.39-7.48 (4H), 7.29-7.39 (6H), 7.18-7.26 (12H), 7.08 (2H).

Example 3

<Synthesis of 4,4''''-bis{(biphenyl-4-yl)-phenylamino}-(1,1':4',1":4'',1''':4''',1''''-quinquephenyl) (Compound 1-13)>

The reaction was carried out under the same conditions as those of Example 1, except that 4,4'-diiodobiphenyl was replaced with 4,4''-diiodo-1,1':4',1''-terphenyl. As a result, a pale yellow powder of 4,4''''-bis{(biphenyl-4-yl)-phenylamino}-(1,1':4',1":4''',1''':4''',1''''-quinquephenyl) (Compound 1-13; 9.8 g; yield 66%).

[Chemical Formula 200]

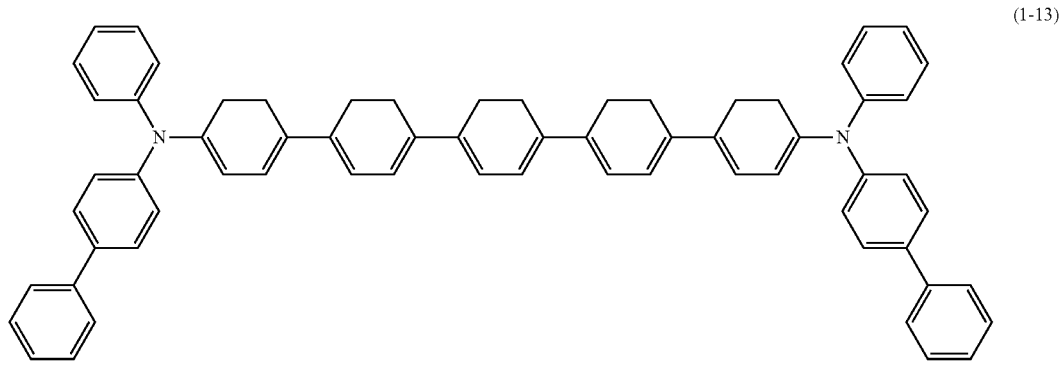

(1-13)

The structure of the obtained pale yellow powder was identified by NMR.

$^1$H-NMR (CDCl$_3$) detected 48 hydrogen signals, as follows.

δ (ppm)=7.66-7.80 (12H), 7.50-7.64 (12H), 7.42-7.50 (4H), 7.28-7.38 (6H), 7.20-7.26 (12H), 7.08 (2H).

Example 4

<Synthesis of 4,4''''-bis{(biphenyl-4-yl)-phenylamino}-(1,1':3',1'':2'',1''':3''',1''''-quinquephenyl) (Compound 1-15)>

The reaction was carried out under the same conditions as those of Example 1, except that 4,4'-diiodobiphenyl was replaced with 3,3''-dibromo-1,1':2',1''-terphenyl). As a result, a pale yellow powder of 4,4''''-bis{(biphenyl-4-yl)-phenylamino}-(1,1':3',1'':2'',1''':3''',1''''-quinquephenyl) (Compound 1-15; 17.0 g; yield 92%) was obtained.

The structure of the obtained pale yellow powder was identified by NMR.

$^1$H-NMR (CDCl$_3$) detected 48 hydrogen signals, as follows.

δ (ppm)=7.00-7.62 (48H).

Example 5

<Synthesis of 4,4''''-bis{(biphenyl-4-yl)-phenylamino}-(1,1':3',1'':3'',1''':3''',1''''-quinquephenyl) (Compound 1-17)>

The reaction was carried out under the same conditions as those of Example 1, except that 4,4'-diiodobiphenyl was replaced with 3,3''-dibromo-1,1':3',1''-terphenyl. As a result, a pale yellow powder of 4,4''''-bis{(biphenyl-4-yl)-phenylamino}-(1,1':3',1'':3'',1''':3''',1''''-quinquephenyl) (Compound 1-17; 10.5 g; yield 57%) was obtained.

[Chemical Formula 201]

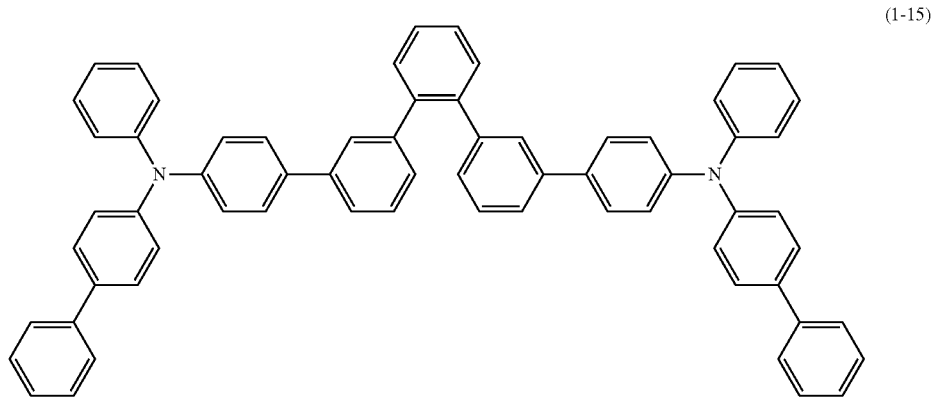

(1-15)

[Chemical Formula 202]

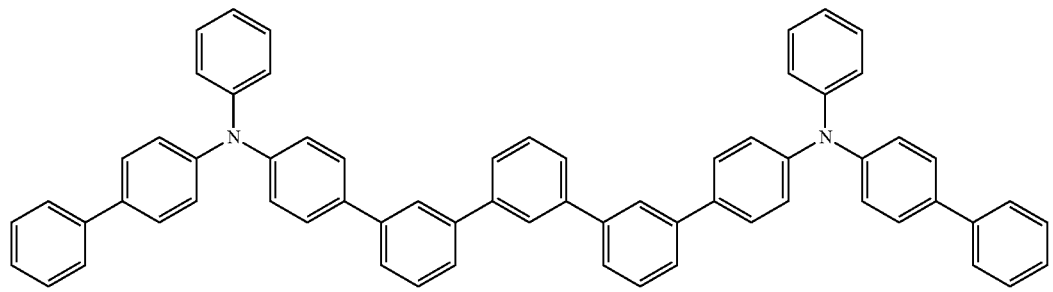

(1-17)

The structure of the obtained pale yellow powder was identified by NMR.

$^1$H-NMR (CDCl$_3$) detected 48 hydrogen signals, as follows.

δ (ppm)=7.93 (1H), 7.87 (2H), 7.40-7.72 (24H), 7.16-7.38 (18H), 7.09 (3H).

Example 6

<Synthesis of 4,4'''-bis{(biphenyl-4-yl)-phenylamino}-(1,1':2',1'':2'',1'''-quaterphenyl) (Compound 1-21)>

The reaction was carried out under the same conditions as those of Example 1, except that 4,4'-diiodobiphenyl was replaced with 2,2'-dibromobiphenyl. As a result, a pale yellow powder of 4,4'''-bis{(biphenyl-4-yl)-phenylamino}-(1,1':2',1'':2'',1'''-quaterphenyl) (Compound 1-21; 9.0 g; yield 83%) was obtained.

[Chemical Formula 203]

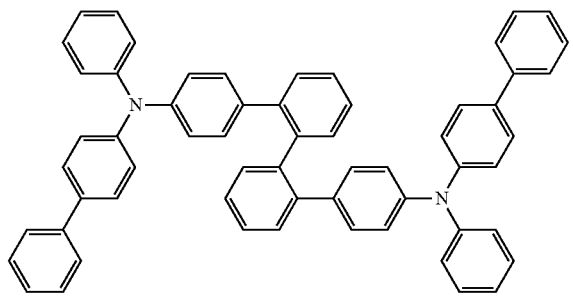

(1-21)

The structure of the obtained pale yellow powder was identified by NMR.

$^1$H-NMR (CDCl$_3$) detected 44 hydrogen signals, as follows.

δ (ppm)=7.45-7.54 (6H), 7.23-7.45 (16H), 7.13-7.22 (4H), 7.05-7.13 (8H), 6.94 (2H), 6.82 (4H), 6.62 (4H).

Example 7

<Synthesis of 4,4'''-bis{(naphthalen-1-yl)-phenylamino}-(1,1':3',1'':3'',1'''-quaterphenyl) (Compound 1-22)>

The reaction was carried out under the same conditions as those of Example 1, except that 4,4'-diiodobiphenyl was replaced with 3,3'-dibromobiphenyl, and N-phenyl-N-{4-(4,4,5,5-tetramethyl-1,3,2-dioxaborolan-2-yl)phenyl}-(1,1'-biphenyl-4-yl)amine was replaced with N-phenyl-N-{4-(4,4,5,5-tetramethyl-1,3,2-dioxaborolan-2-yl)phenyl}-(naphthalen-1-yl)amine. As a result, a pale yellow powder of 4,4'''-bis{(naphthalen-1-yl)-phenylamino}-(1,1':3',1'':3'',1'''-quaterphenyl) (Compound 1-22; 4.00 g; yield 26%) was obtained.

[Chemical Formula 204]

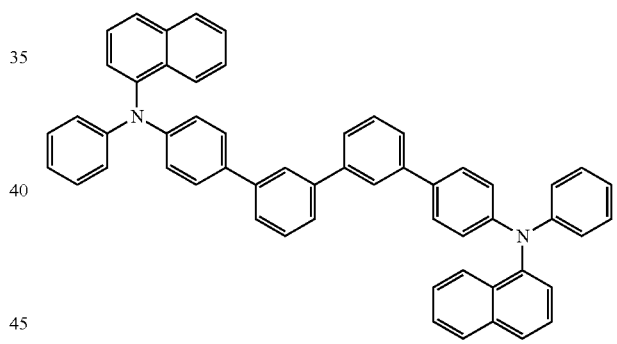

(1-22)

The structure of the obtained pale yellow powder was identified by NMR.

$^1$H-NMR (CDCl$_3$) detected 40 hydrogen signals, as follows.

δ (ppm)=7.99 (2H), 7.92 (2H), 7.78-7.85 (4H), 7.35-7.61 (18H), 7.19-7.28 (4H), 7.06-7.15 (8H), 6.98 (2H).

Example 8

<Synthesis of 4,4''''-bis{(biphenyl-4-yl)-phenylamino}-(1,1':4',1'':2''',1'''':4''',1''''-quinquephenyl) (Compound 1-23)>

The reaction was carried out under the same conditions as those of Example 1, except that 4,4'-diiodobiphenyl was replaced with 4,4''-dibromo-1,1':2',1''-terphenyl. As a result, a pale yellow powder of 4,4''''-bis{(biphenyl-4-yl)-phenylamino}-(1,1':4',1'':2''',1'''':4''',1''''-quinquephenyl) (Compound 1-23; 13.8 g; yield 62%) was obtained.

[Chemical Formula 205]

(1-23)

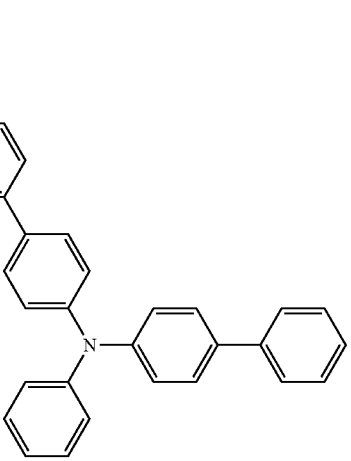

The structure of the obtained pale yellow powder was identified by NMR.
$^1$H-NMR (CDCl$_3$) detected 48 hydrogen signals, as follows.
δ (ppm)=7.60 (4H), 7.03-7.56 (44H).

Example 9

<Synthesis of 4,4''''-bis{(biphenyl-4-yl)-phenylamino}-(1,1':2',1'':3'',1''':2''',1''''-quinquephenyl) (Compound 1-24)>

The reaction was carried out under the same conditions as those of Example 1, except that 4,4'-diiodobiphenyl was replaced with 2,2''-dibromo-1,1':3',1''-terphenyl. As a result, a pale yellow powder of 4,4''''-bis{(biphenyl-4-yl)-phenylamino}-(1,1':2',1'':3'',1''':2''',1''''-quinquephenyl) (Compound 1-24; 9.7 g; yield 69%) was obtained.

[Chemical Formula 206]

(1-24)

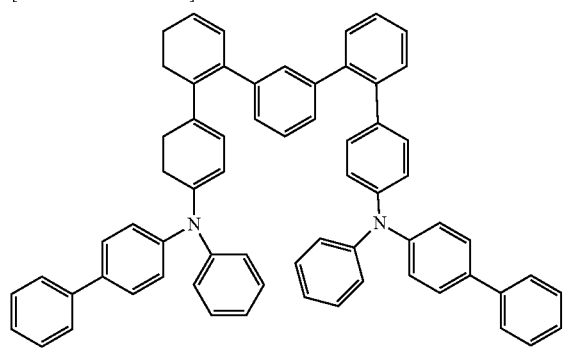

The structure of the obtained pale yellow powder was identified by NMR.
$^1$H-NMR (CDCl$_3$) detected 48 hydrogen signals, as follows.
δ (ppm)=7.30-7.56 (20H), 6.91-7.24 (28H).

Example 10

<Synthesis of 4,4''''-bis{(biphenyl-4-yl)-phenylamino}-(1,1':4',1'':3'',1''':4''',1''''-quinquephenyl) (Compound 1-25)>

The reaction was carried out under the same conditions as those of Example 1, except that 4,4'-diiodobiphenyl was replaced with 4,4''-dibromo-1,1':3',1''-terphenyl. As a result, a pale yellow powder of 4,4''''-bis{(biphenyl-4-yl)-phenylamino}-(1,1':4',1'':3'',1''':4''',1''''-quinquephenyl) (Compound 1-25; 16.5 g; yield 74%) was obtained.

[Chemical Formula 207]

(1-25)

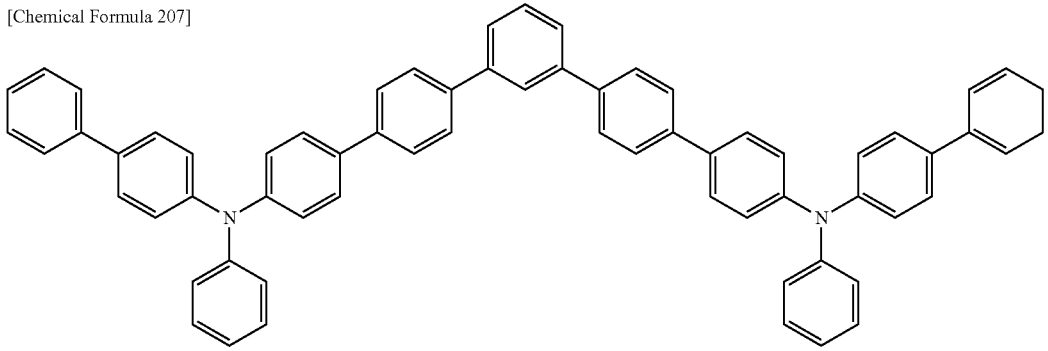

The structure of the obtained pale yellow powder was identified by NMR.

$^1$H-NMR (CDCl$_3$) detected 48 hydrogen signals, as follows.

δ (ppm)=7.93 (1H), 7.06-7.80 (47H).

Example 11

<Synthesis of 4,4''''-bis{(dibenzofuran-1-yl)-phenylamino}-(1,1':4',1'':2'',1''':4''',1''''-quinquephenyl) (Compound 1-26)>

The reaction was carried out under the same conditions as those of Example 1, except that 4,4'-diiodobiphenyl was replaced with 4,4''-dibromo(1,1':2',1''-terphenyl) 4,4''-dibromo-1,1':2',1''-terphenyl, and N-phenyl-N-{4-(4,4,5,5-tetramethyl-1,3,2-dioxaborolan-2-yl)phenyl}-(1,1'-biphenyl-4-yl)amine was replaced with N-phenyl-N-{4-(4,4,5,5-tetramethyl-1,3,2-dioxaborolan-2-yl)phenyl}-(dibenzofuran-1-yl)amine. As a result, a pale yellow powder of 4,4''''-bis{(dibenzofuran-1-yl)-phenylamino}-(1,1':4',1'':2'',1''':4''',1''''-quinquephenyl) (Compound 1-26; 14.0 g; yield 61%) was obtained.

[Chemical Formula 208]

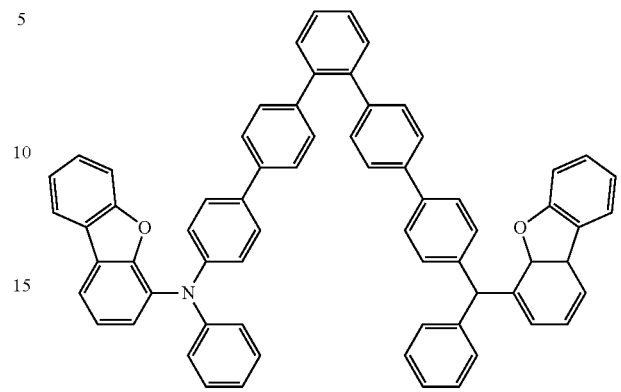

(1-26)

The structure of the obtained pale yellow powder was identified by NMR.

$^1$H-NMR (CDCl$_3$) detected 44 hydrogen signals, as follows.

δ (ppm)=7.97 (2H), 7.79 (2H), 7.02-7.55 (40H).

Example 12

<Synthesis of 4,4''''-bis{(biphenyl-4-yl)-phenylamino}-(1,1':2',1'':2'',1''':2''',1''''-quinquephenyl) (Compound 1-27)>
The reaction was carried out under the same conditions as those of Example 1, except that 4,4'-diiodobiphenyl was replaced with 2,2''-dibromo-1,1':2',1''-terphenyl). As a result, a pale yellow powder of 4,4''''-bis{(biphenyl-4-yl)-phenylamino}-(1,1':2',1'':2'',1''':2''',1''''-quinquephenyl) (Compound 1-27; 8.5 g; yield 61%) was obtained.

[Chemical Formula 209]

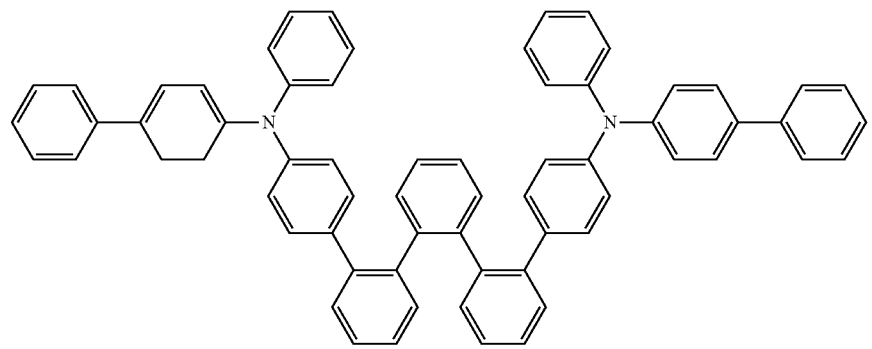

(1-27)

The structure of the obtained pale yellow powder was identified by NMR.

¹H-NMR (CDCl₃) detected 48 hydrogen signals, as follows.

δ (ppm)=7.62 (4H), 6.78-7.57 (36H), 6.53 (4H), 6.46 (2H), 6.38 (2H).

Example 13

<Synthesis of 4,4'''-bis{(biphenyl-4-yl)-(phenyl-d₅)amino}-(1,1':3',1'':3'',1'''-quaterphenyl) (Compound 1-28)>

The reaction was carried out under the same conditions as those of Example 1, except that 4,4'-diiodobiphenyl was replaced with 3,3'-dibromobiphenyl, and N-phenyl-N-{4-(4,4,5,5-tetramethyl-1,3,2-dioxaborolan-2-yl)phenyl}-(1,1'-biphenyl-4-yl)amine was replaced with N-(phenyl-d₅)-N-{4-(4,4,5,5-tetramethyl-1,3,2-dioxaborolan-2-yl)phenyl}-(1,1'-biphenyl-4-yl)amine. As a result, a pale yellow powder of 4,4'''-bis{(biphenyl-4-yl)-(phenyl-d₅)amino}-(1,1':3',1'':3'',1'''-quaterphenyl) (Compound 1-28; 8.7 g; yield 68%) was obtained.

The structure of the obtained pale yellow powder was identified by NMR.

¹H-NMR (CDCl₃) detected 34 hydrogen signals, as follows.

δ (ppm)=7.87 (2H), 7.40-7.66 (20H), 7.30-7.38 (4H), 7.19-7.26 (8H).

Example 14

<Synthesis of 4,4'''-bis{(biphenyl-4-yl)-phenylamino}-(1,1':3',1'':4'',1'''-quaterphenyl) (Compound 1-38)>

The reaction was carried out under the same conditions as those of Example 1, except that 4,4'-diiodobiphenyl was replaced with 3,4'-dibromobiphenyl. As a result, a pale yellow powder of 4,4'''-bis{(biphenyl-4-yl)-phenylamino}-(1,1':3',1'':4'',1'''-quaterphenyl) (Compound 1-38; 14.0 g; yield 84%) was obtained.

[Chemical Formula 210]

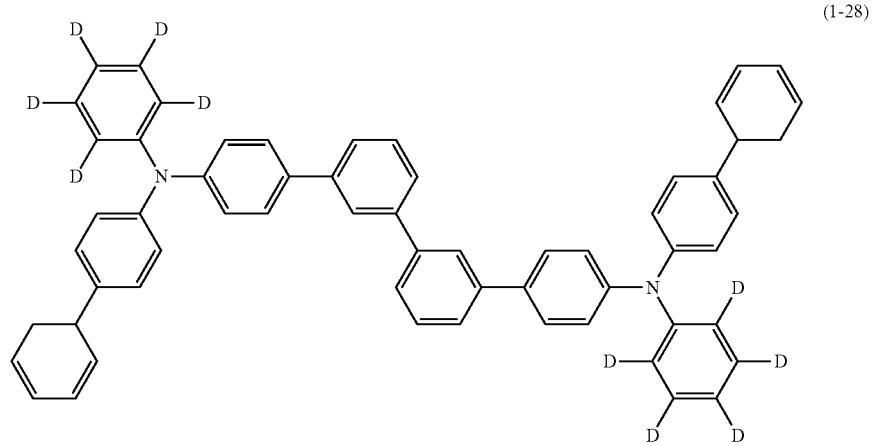

(1-28)

[Chemical Formula 211]

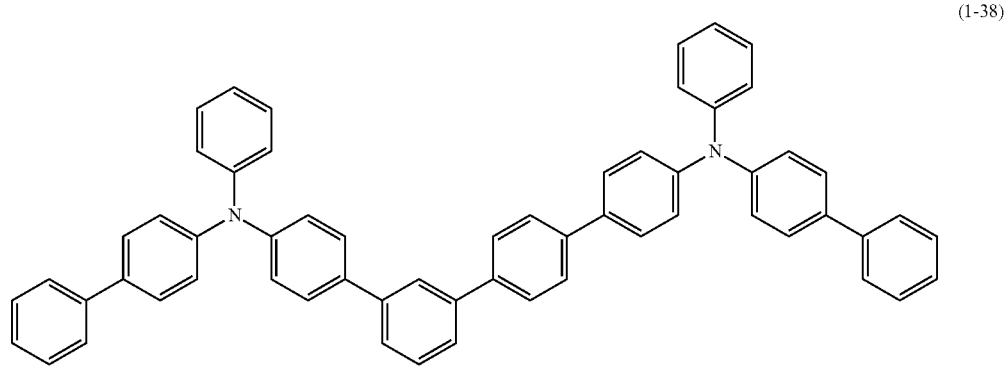

(1-38)

The structure of the obtained pale yellow powder was identified by NMR.

$^1$H-NMR (CDCl$_3$) detected 44 hydrogen signals, as follows.

δ (ppm)=7.00-8.00 (44H).

Example 15

The glass transition points of the arylamine compounds of the general formula (1) were determined using a high-sensitive differential scanning calorimeter (DSC3100S produced by Bruker AXS).

|  | Glass transition point |
| --- | --- |
| Compound of Example 1 | 119° C. |
| Compound of Example 2 | 114° C. |
| Compound of Example 3 | 124° C. |
| Compound of Example 4 | 115° C. |
| Compound of Example 5 | 118° C. |
| Compound of Example 6 | 111° C. |
| Compound of Example 7 | 112° C. |
| Compound of Example 8 | 129° C. |
| Compound of Example 9 | 113° C. |
| Compound of Example 10 | 126° C. |
| Compound of Example 11 | 131° C. |
| Compound of Example 12 | 121° C. |
| Compound of Example 13 | 113° C. |
| Compound of Example 14 | 117° C. |

The arylamine compounds of the general formula (1) have glass transition points of 100° C. or higher, demonstrating that the compounds have a stable thin-film state.

Example 16

A 100 nm-thick vapor-deposited film was fabricated on an ITO substrate using the arylamine compounds of the general formula (1), and a work function was measured using an ionization potential measuring device (PYS-202 produced by Sumitomo Heavy Industries, Ltd.).

|  | Work function |
| --- | --- |
| Compound of Example 1 | 5.68 eV |
| Compound of Example 2 | 5.73 eV |
| Compound of Example 3 | 5.69 eV |
| Compound of Example 4 | 5.74 eV |
| Compound of Example 5 | 5.77 eV |
| Compound of Example 6 | 5.73 eV |
| Compound of Example 7 | 5.81 eV |
| Compound of Example 8 | 5.71 eV |
| Compound of Example 9 | 5.74 eV |
| Compound of Example 10 | 5.72 eV |
| Compound of Example 11 | 5.74 eV |
| Compound of Example 12 | 5.73 eV |
| Compound of Example 13 | 5.76 eV |
| Compound of Example 14 | 5.74 eV |

As the results show, the arylamine compounds of the general formula (1) have desirable energy levels compared to the work function 5.4 eV of common hole transport materials such as NPD and TPD, and thus possess desirable hole transportability.

Example 17

<Synthesis of N5',N5',N9',N9'-tetrakis{4-(tert-butyl)phenyl}spiro(fluorene-9,7'-fluoreno[4,3-b]benzofuran)-5',9'-diamine (Compound 2-1)>

5',9'-dibromospiro(fluorene-9,7'-fluoreno[4,3-b]benzofuran) (5.0 g), bis{4-(tert-butyl)phenyl}amine (6.0 g), palladium acetate (0.08 g), sodium tert-butoxide (3.4 g), tri-tert-butylphosphine (0.07 g), and toluene (60 mL) were added into a nitrogen-substituted reaction vessel and the mixture was heated and stirred for 2 hours under reflux. The mixture was cooled to a room temperature, dichloromethane and water were added, and an organic layer was collected by liquid separation. After the organic layer was concentrated, purification by column chromatography was performed to obtain a powder of N5',N5',N9',N9'-tetrakis{4-(tert-butyl)phenyl}spiro(fluorene-9,7'-fluoreno[4,3-b]benzofuran)-5',9'-diamine (Compound 2-1; 3.1 g; yield 36%)

[Chemical Formula 212]

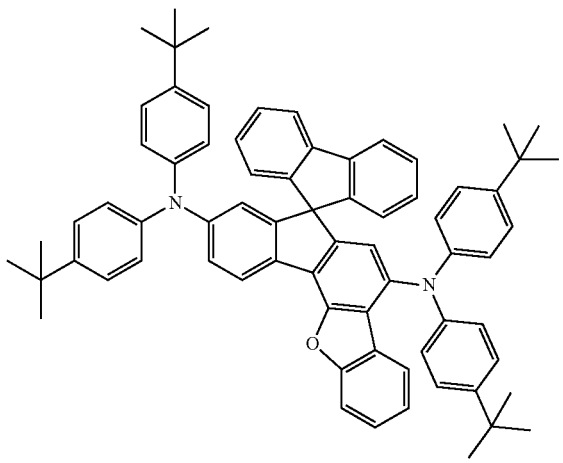

(2-1)

Example 18

<Synthesis of N2,N2,N7,N7-tetrakis{4-(tert-butyl)phenyl}spiro(dibenzo[5,6:7,8]fluoreno[4,3-b]benzofuran-5,9'-fluorene)-2,7-diamine (Compound 2-2)>

The reaction was carried out under the same conditions as those of Example 17, except that 5',9'-dibromospiro(fluorene-9,7'-fluoreno[4,3-b]benzofuran) was replaced with 2,7-dibromospiro(dibenzo[5,6:7,8]fluoreno[4,3-b]benzofuran-5,9'-fluorene). As a result, a powder of N2,N2,N7,N7-tetrakis{4-(tert-butyl)phenyl}spiro(dibenzo[5,6:7,8]fluoreno[4,3-b]benzofuran-5,9'-fluorene)-2,7-diamine (Compound 2-2; 2.5 g; yield 31%) was obtained.

[Chemical Formula 213]

(2-2)

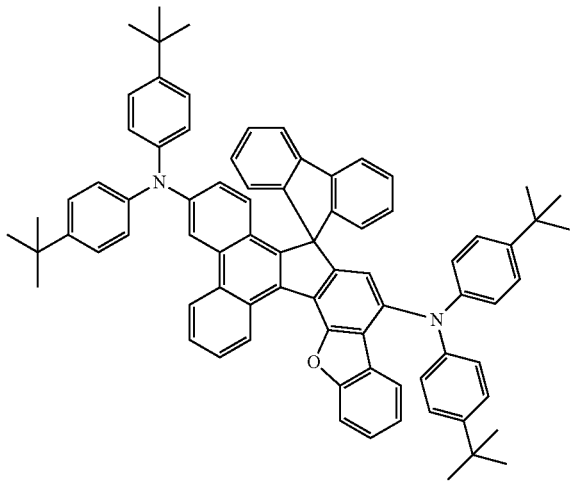

Example 19

<Synthesis of N5,N5,N9,N9-tetrakis{4-(tert-butyl)phenyl}spiro(benzo[5,6]fluoreno[4,3-b]benzofuran-7,9'-fluorene)-5,9-diamine (Compound 2-3)>

The reaction was carried out under the same conditions as those of Example 17, except that 5',9'-dibromospiro(fluorene-9,7'-fluoreno[4,3-b]benzofuran) was replaced with 5,9-dibromospiro(benzo[5,6]fluoreno[4,3-b]benzofuran-7,9'-fluorene). As a result, a powder of N5,N5,N9,N9-tetrakis{4-(tert-butyl)phenyl}spiro(benzo[5,6]fluoreno[4,3-b]benzofuran-7,9'-fluorene)-5,9-diamine (Compound 2-3; 3.0 g; yield 36%) was obtained.

[Chemical Formula 214]

(2-3)

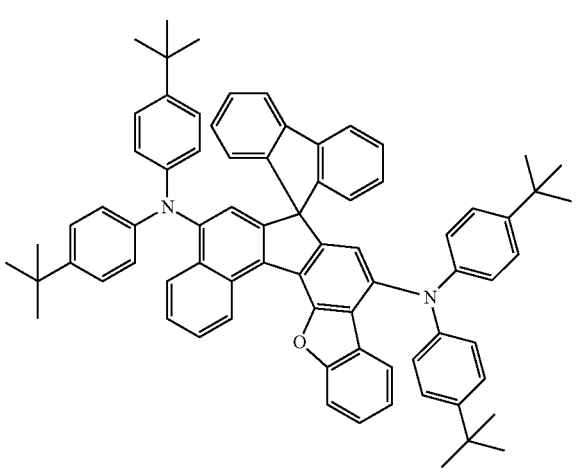

Example 20

<Synthesis of N6',N6',N10',N10'-tetrakis{4-(tert-butyl)phenyl}spiro(fluorene-9,8'-fluoreno[3,4-b]benzofuran)-6',10'-diamine (Compound 2-4)>

The reaction was carried out under the same conditions as those of Example 17, except that 5',9'-dibromospiro(fluorene-9,7'-fluoreno[4,3-b]benzofuran) was replaced with 6',10'-dibromospiro(fluorene-9,8'-fluoreno[3,4-b]benzofuran). As a result, a powder of N6',N6',N10',N10'-tetrakis{4-(tert-butyl)phenyl}spiro(fluorene-9,8'-fluoreno[3,4-b]benzofuran)-6',10'-diamine (Compound 2-4; 2.5 g; yield 34%) was obtained.

[Chemical Formula 215]

(2-4)

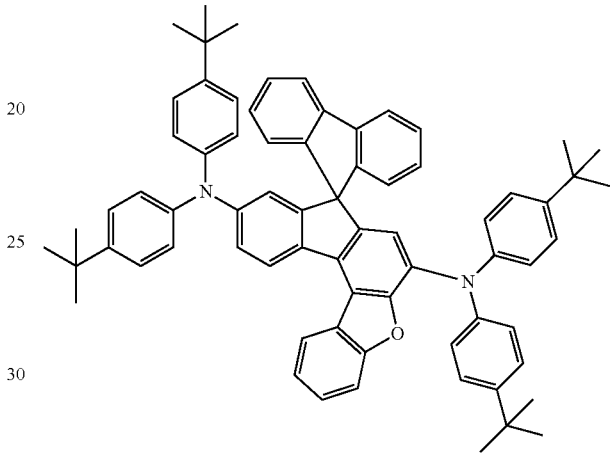

Example 21

<Synthesis of N5,N5,N9,N9-tetrakis{4-(tert-butyl)phenyl}spiro(fluoreno[4,3-b]benzofuran-7,9'-xanthene)-5,9-diamine (Compound 2-5)>

The reaction was carried out under the same conditions as those of Example 17, except that 5',9'-dibromospiro(fluorene-9,7'-fluoreno[4,3-b]benzofuran) was replaced with 5,9-dibromospiro(fluoreno[4,3-b]benzofuran-7,9'-xanthene). As a result, a powder of N5,N5,N9,N9-tetrakis{4-(tert-butyl)phenyl}spiro(fluoreno[4,3-b]benzofuran-7,9'-xanthene)-5,9-diamine (Compound 2-5; 2.4 g; yield 28%) was obtained.

[Chemical Formula 216]

(2-5)

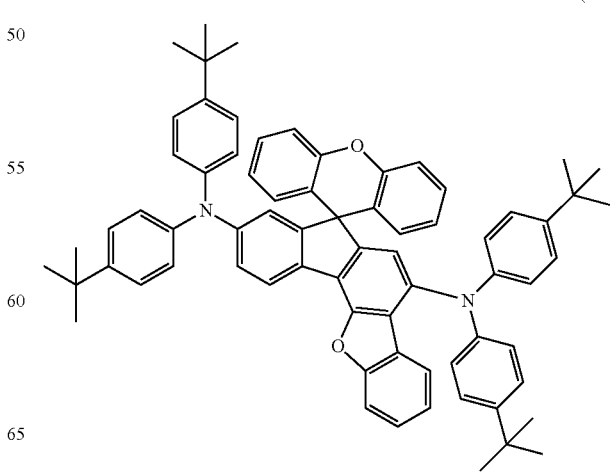

Example 22

<Synthesis of N5',N9'-bis(biphenyl-4-yl)-N5',N9'-bis{4-(tert-butyl)phenyl}-2-fluorospiro(fluorene-9,7'-fluoreno[4,3-b]benzofuran)-5',9'-diamine (Compound 2-6)>

The reaction was carried out under the same conditions as those of Example 17, except that 5',9'-dibromospiro(fluorene-9,7'-fluoreno[4,3-b]benzofuran) was replaced with 5',9'-dibromo-2-fluorospiro(fluorene-9,7'-fluoreno[4,3-b]benzofuran), and bis{4-(tert-butyl)phenyl}amine was replaced with (biphenyl-4-yl)-{4-(tert-butyl)phenyl}amine. As a result, a powder of N5',N9'-bis(biphenyl-4-yl)-N5',N9'-bis{4-(tert-butyl)phenyl}-2-fluorospiro(fluorene-9,7'-fluoreno[4,3-b]benzofuran)-5',9'-diamine (Compound 2-6; 2.4 g; yield 28%) was obtained.

[Chemical Formula 217]

(2-6)

Example 23

<Synthesis of N5,N9-bis{4-(tert-butyl)phenyl}-N5,N9-bis{4-(trimethylsilyl)phenyl}spiro(benzo[5,6]fluoreno[4,3-b]benzofuran-7,9'-fluorene)-5,9-diamine (Compound 2-7)>

The reaction was carried out under the same conditions as those of Example 17, except that 5',9'-dibromospiro(fluorene-9,7'-fluoreno[4,3-b]benzofuran) was replaced with 5,9-dibromospiro(benzo[5,6]fluoreno[4,3-b]benzofuran-7,9'-fluorene), and bis{4-(tert-butyl)phenyl}amine was replaced with {4-(tert-butyl)phenyl}-{4-(trimethylsilyl)phenyl}amine. As a result, a powder of N5,N9-bis{4-(tert-butyl)phenyl}-N5,N9-bis{4-(trimethylsilyl)phenyl}spiro(benzo[5,6]fluoreno[4,3-b]benzofuran-7,9'-fluorene)-5,9-diamine (Compound 2-7; 3.0 g; yield 35%) was obtained.

[Chemical Formula 218]

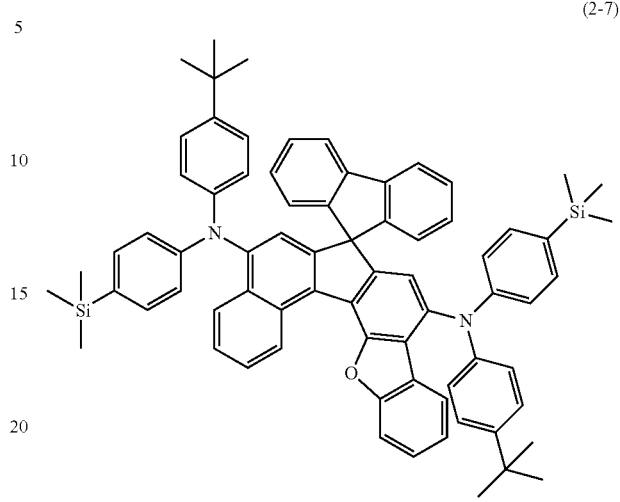

(2-7)

Example 24

<Synthesis of N5',N9'-bis{4-(tert-butyl)phenyl}-N5',N9'-bis{4-(trimethylsilyl)phenyl}spiro(fluorene-9,7'-fluoreno[4,3-b]benzothiophene)-5',9'-diamine (Compound 2-8)>

The reaction was carried out under the same conditions as those of Example 17, except that 5',9'-dibromospiro(fluorene-9,7'-fluoreno[4,3-b]benzofuran) was replaced with 5',9'-dibromospiro(fluorene-9,7'-fluoreno[4,3-b]benzothiophene), and bis{4-(tert-butyl)phenyl}amine was replaced with {4-(tert-butyl)phenyl}-{4-(trimethylsilyl)phenyl}amine. As a result, a powder of N5',N9'-bis{4-(tert-butyl)phenyl}-N5',N9'-bis{4-(trimethylsilyl)phenyl}spiro(fluorene-9,7'-fluoreno[4,3-b]benzothiophene)-5',9'-diamine (Compound 2-8; 3.2 g; yield 37%) was obtained.

[Chemical Formula 219]

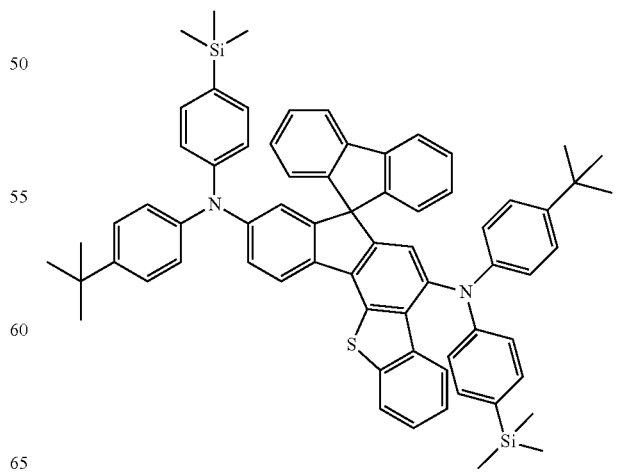

(2-8)

Example 25

<Synthesis of N5,N9-bis(biphenyl-4-yl)-N5,N9-bis{4-(tert-butyl)phenyl}spiro(benzo[4',5']thieno[2',3':5,6]fluoreno[4,3-b]benzofuran-7,9'-fluorene)-5,9-diamine (Compound 2-9)>

The reaction was carried out under the same conditions as those of Example 17, except that 5',9'-dibromospiro(fluorene-9,7'-fluoreno[4,3-b]benzofuran) was replaced with 5,9-dibromospiro(benzo[4',5']thieno[2',3':5,6]fluoreno[4,3-b]benzofuran-7,9'-fluorene), and bis{4-(tert-butyl)phenyl}amine was replaced with (biphenyl-4-yl)-{4-(tert-butyl)phenyl}amine. As a result, a powder of N5,N9-bis(biphenyl-4-yl)-N5,N9-bis{4-(tert-butyl)phenyl}spiro(benzo[4',5']thieno[2',3':5,6]fluoreno[4,3-b]benzofuran-7,9'-fluorene)-5,9-diamine (Compound 2-9; 2.8 g; yield 34%) was obtained.

[Chemical Formula 220]

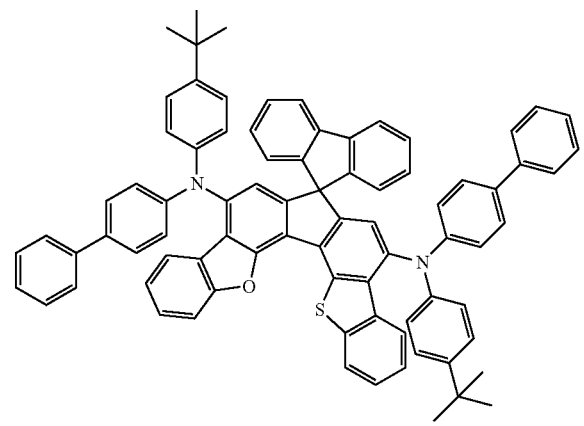

(2-9)

Example 26

<Synthesis of N5',N5',N9',N9'-tetrakis{4-(tert-butyl)phenyl}-12',12'-dimethyl-12'H-spiro(fluorene-9,7'-indeno[1,2-a]fluorene)-5',9'-diamine (Compound 2-10)>

The reaction was carried out under the same conditions as those of Example 17, except that 5',9'-dibromospiro(fluorene-9,7'-fluoreno[4,3-b]benzofuran) was replaced with 5',9'-dibromo-12',12'-dimethyl-12'H-spiro(fluorene-9,7'-indeno[1,2-a]fluorene). As a result, a powder of N5',N5',N9',N9'-tetrakis{4-(tert-butyl)phenyl}-12',12'-dimethyl-12'H-spiro(fluorene-9,7'-indeno[1,2-a]fluorene)-5',9'-diamine (Compound 2-10; 1.8 g; yield 49%) was obtained.

[Chemical Formula 221]

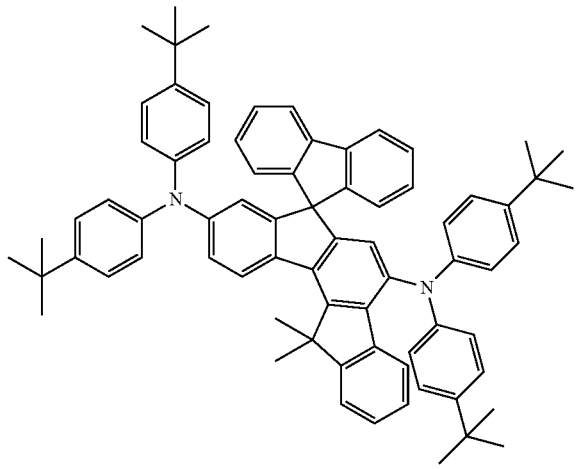

(2-10)

Example 27

<Synthesis of N6',N10'-bis(biphenyl-4-yl)-N6',N10'-bis{4-(tert-butyl)phenyl}-5'-methyl-5'H-spiro(fluorene-9,8'-indeno[2,1-c]carbazole)-6',10'-diamine (Compound 2-11)>

The reaction was carried out under the same conditions as those of Example 17, except that 5',9'-dibromospiro(fluorene-9,7'-fluoreno[4,3-b]benzofuran) was replaced with 6',10'-dibromo-5'-methyl-5'H-spiro(fluorene-9,8'-indeno[2,1-c]carbazole), and bis{4-(tert-butyl)phenyl}amine was replaced with (biphenyl-4-yl)-{4-(tert-butyl)phenyl}amine. As a result, a powder of N6',N10'-bis(biphenyl-4-yl)-N6',N10'-bis{4-(tert-butyl)phenyl}-5'-methyl-5'H-spiro(fluorene-9,8'-indeno[2,1-c]carbazole)-6',10'-diamine (Compound 2-11; 2.3 g; yield 41%) was obtained.

[Chemical Formula 222]

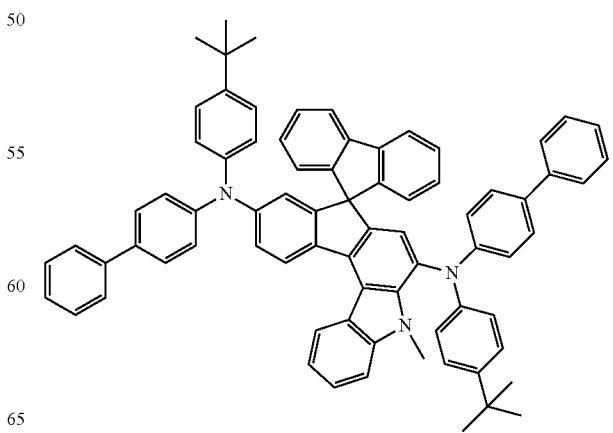

(2-11)

141

Example 28

<Synthesis of N6,N6,N10,N10-tetrakis{4-(tert-butyl)phenyl}spiro(benzo[4',5']furo[2',3':5,6]fluoreno[3,4-b]benzofuran-8,9'-fluorene)-6,10-diamine (Compound 2-22)>

The reaction was carried out under the same conditions as those of Example 17, except that 5',9'-dibromospiro(fluorene-9,7'-fluoreno[4,3-b]benzofuran) was replaced with 6,10-dibromospiro(benzo[4',5']furo[2',3':5,6]fluoreno[3,4-b]benzofuran-8,9'-fluorene). As a result, a powder of N6,N6,N10,N10-tetrakis{4-(tert-butyl)phenyl}spiro(benzo[4',5']furo[2',3':5,6]fluoreno[3,4-b]benzofuran-8,9'-fluorene)-6,10-diamine (Compound 2-22; 1.5 g; yield 41%) was obtained.

[Chemical Formula 223]

(2-22)

Example 29

<Synthesis of N6,N6,N10,N10-tetrakis{4-(tert-butyl)phenyl}-8,8-diphenyl-benzo[4',5']furo[2',3':5,6]fluoreno[3,4-b]benzofuran-6,10-diamine (Compound 2-23)>

The reaction was carried out under the same conditions as those of Example 17, except that 5',9'-dibromospiro(fluorene-9,7'-fluoreno[4,3-b]benzofuran) was replaced with 6,10-dibromo-8,8-diphenyl-benzo[4',5']furo[2',3':5,6]fluoreno[3,4-b]benzofuran. As a result, a powder of N6,N6,N10,N10-tetrakis{4-(tert-butyl)phenyl}-8,8-diphenyl-benzo[4',5']furo[2',3':5,6]fluoreno[3,4-b]benzofuran-6,10-diamine (Compound 2-23; 3.2 g; yield 49%) was obtained.

142

[Chemical Formula 224]

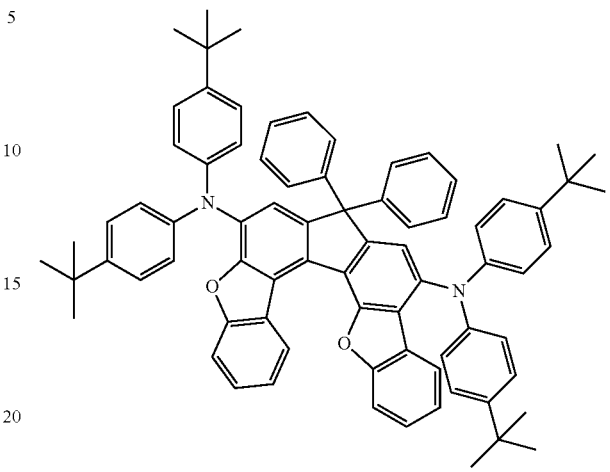

(2-23)

Example 30

<Synthesis of N6,N10-bis{4-(tert-butyl)phenyl}-N6,N10-bis{4-(trimethylsilyl)phenyl}spiro(benzo[4',5']furo[2',3':5,6]fluoreno[3,4-b]benzofuran-8,9'-fluorene)-6,10-diamine (Compound 2-24)>

The reaction was carried out under the same conditions as those of Example 17, except that 5',9'-dibromospiro(fluorene-9,7'-fluoreno[4,3-b]benzofuran) was replaced with 6,10-dibromospiro(benzo[4',5']furo [2',3':5,6]fluoreno[3,4-b]benzofuran-8,9'-fluorene), and bis{4-(tert-butyl)phenyl}amine was replaced with {4-(tert-butyl)phenyl}-{4-(trimethylsilyl)phenyl}amine. As a result, a powder of N6,N10-bis{4-(tert-butyl)phenyl}-N6,N10-bis{4-(trimethylsilyl)phenyl}spiro(benzo[4',5']furo [2',3':5,6]fluoreno[3,4-b]benzofuran-8,9'-fluorene)-6,10-diamine (Compound 2-24; 2.3 g; yield 43%) was obtained.

[Chemical Formula 225]

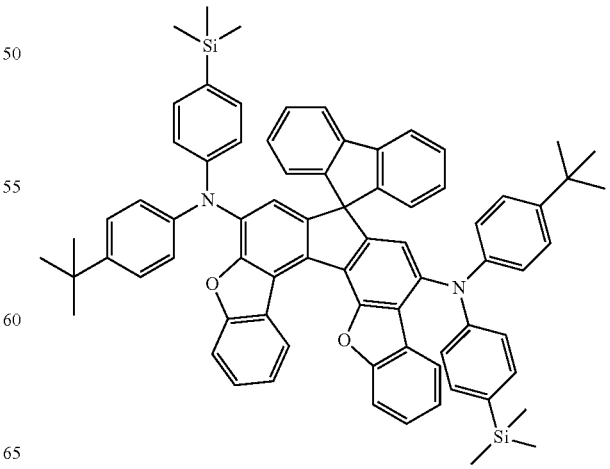

(2-24)

143

Example 31

<Synthesis of N6,N6,N10,N10-tetrakis{4-(tert-butyl)phenyl}-8,8-bis{4-(tert-butyl)phenyl}-benzo[4',5']furo[2',3':5,6]fluoreno[3,4-b]benzofuran-6,10-diamine (Compound 2-25)>

The reaction was carried out under the same conditions as those of Example 17, except that 5',9'-dibromospiro(fluorene-9,7'-fluoreno[4,3-b]benzofuran) was replaced with 6,10-dibromo-8,8-bis{4-(tert-butyl)phenyl}-benzo[4',5']furo[2',3':5,6]fluoreno[3,4-b]benzofuran. As a result, a powder of N6,N6,N10,N10-tetrakis{4-(tert-butyl)phenyl}-8,8-bis{4-(tert-butyl)phenyl}-benzo[4',5']furo[2',3':5,6]fluoreno[3,4-b]benzofuran-6,10-diamine (Compound 2-25; 8.2 g; yield 54%) was obtained.

[Chemical Formula 226]

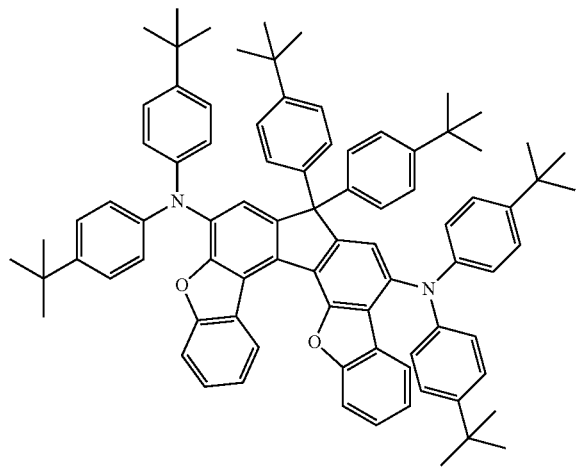

(2-25)

Example 32

The organic EL device, as shown in FIG. 1, was fabricated by vapor-depositing a hole injection layer 3, a first hole transport layer 4, a second hole transport layer 5, a light emitting layer 6, an electron transport layer 7, an electron injection layer 8, and a cathode (aluminum electrode) 9 in this order on a glass substrate 1 on which an ITO electrode was formed as a transparent anode 2 beforehand.

Specifically, the glass substrate 1 having ITO (film thickness of 150 nm) formed thereon was subjected to ultrasonic washing in isopropyl alcohol for 20 minutes and then dried for 10 minutes on a hot plate heated to 200° C. After UV ozone treatment for 15 minutes, the glass substrate with ITO was installed in a vacuum vapor deposition apparatus, and the pressure was reduced to 0.001 Pa or lower. Compound HIM-1 of the structural formula below was then formed in a film thickness of 5 nm as the hole injection layer 3 so as to cover the transparent anode 2. The first hole transport layer 4 was formed on the hole injection layer 3 by forming the arylamine compounds (4-1) having two triphenylamine structures within a molecule in a film thickness of 60 nm.

144

The second hole transport layer 5 was formed on the first hole transport layer 4 by forming the compound (1-1) of Example 1 in a film thickness of 5 nm. Then, the light emitting layer 6 was formed on the second hole transport layer 5 in a film thickness of 20 nm by dual vapor deposition of the compound (2-1) of Example 17 and Compound EMH-1 of the structural formula below at a vapor deposition rate ratio of the compound (2-1): EMH-1=5:95. The electron transport layer 7 was formed on the light emitting layer 6 in a film thickness of 30 nm by dual vapor deposition of the compound (3a-1) of the structural formula below having an anthracene ring structure and Compound ETM-1 of the structural formula below at a vapor deposition rate ratio of the compound (3a-1): ETM-1=50:50. The electron injection layer 8 was formed on the electron transport layer 7 by forming lithium fluoride in a film thickness of 1 nm. Finally, the cathode 9 was formed by vapor-depositing aluminum in a thickness of 100 nm. The characteristics of the thus fabricated organic EL device were measured in the atmosphere at an ordinary temperature. Table 1 summarizes the results of emission characteristics measurements performed by applying a DC voltage to the fabricated organic EL device.

[Chemical Formula 227]

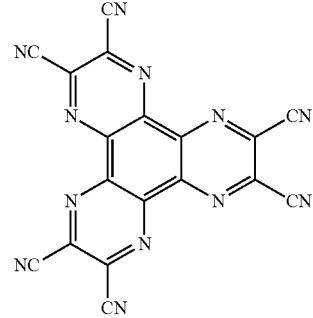

(HIM-1)

[Chemical Formula 228]

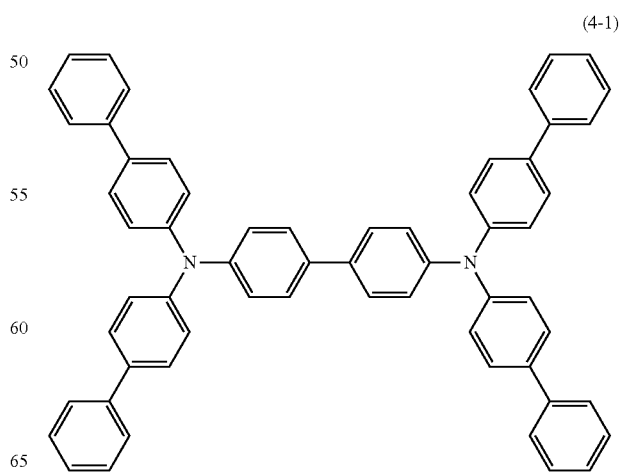

(4-1)

[Chemical Formula 229]

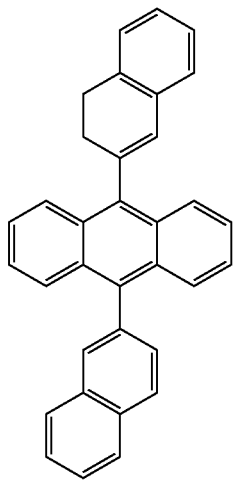

(EMH-1)

[Chemical Formula 230]

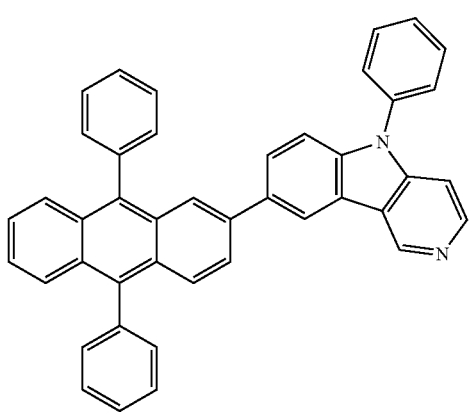

(3a-1)

[Chemical Formula 231]

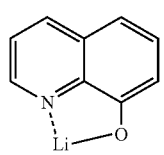

(ETM-1)

Example 33

An organic EL device was fabricated under the same conditions used in Example 32, except that the second hole transport layer 5 was formed by forming the compound (1-11) of Example 2 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 34

An organic EL device was fabricated under the same conditions used in Example 32, except that the second hole transport layer 5 was formed by forming the compound (1-13) of Example 3 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 35

An organic EL device was fabricated under the same conditions used in Example 32, except that the second hole transport layer 5 was formed by forming the compound (1-15) of Example 4 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 36

An organic EL device was fabricated under the same conditions used in Example 32, except that the second hole transport layer 5 was formed by forming the compound (1-17) of Example 5 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 37

An organic EL device was fabricated under the same conditions used in Example 32, except that the second hole transport layer 5 was formed by forming the compound (1-25) of Example 10 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 38

An organic EL device was fabricated under the same conditions used in Example 32, except that the second hole transport layer 5 was formed by forming the compound (1-38) of Example 14 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 39

An organic EL device was fabricated under the same conditions used in Example 32, except that the light emitting layer 6 was formed by forming the compound (2-9) of Example 25 in a film thickness of 20 nm, instead of using the compound (2-1) of Example 17, and dual vapor deposition of the compound (2-9) and Compound EMH-1 of the structural formula was performed at a vapor deposition rate ratio of the compound (2-9): EMH-1=5:95. The characteristics of the organic EL device thus fabricated were measured in the atmosphere at an ordinary temperature. Table 1 summarizes the results of emission characteristics measurements performed by applying a DC voltage to the fabricated organic EL device.

Example 40

An organic EL device was fabricated under the same conditions used in Example 39, except that the second hole transport layer 5 was formed by forming the compound (1-11) of Example 2 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 41

An organic EL device was fabricated under the same conditions used in Example 39, except that the second hole transport layer 5 was formed by forming the compound (1-13) of Example 3 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 42

An organic EL device was fabricated under the same conditions used in Example 39, except that the second hole transport layer 5 was formed by forming the compound (1-15) of Example 4 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 43

An organic EL device was fabricated under the same conditions used in Example 32, except that the light emitting layer 6 was formed by forming the compound (2-24) of Example 30 in a film thickness of 20 nm, instead of using the compound (2-1) of Example 17, and dual vapor deposition of the compound (2-24) and Compound EMH-1 of the structural formula was performed at a vapor deposition rate ratio of the compound (2-24): EMH-1=5:95. The characteristics of the organic EL device thus fabricated were measured in the atmosphere at an ordinary temperature. Table 1 summarizes the results of emission characteristics measurements performed by applying a DC voltage to the fabricated organic EL device.

Example 44

An organic EL device was fabricated under the same conditions used in Example 43, except that the second hole transport layer 5 was formed by forming the compound (1-11) of Example 2 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 45

An organic EL device was fabricated under the same conditions used in Example 43, except that the second hole transport layer 5 was formed by forming the compound (1-13) of Example 3 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Example 46

An organic EL device was fabricated under the same conditions used in Example 43, except that the second hole transport layer 5 was formed by forming the compound (1-15) of Example 4 in a film thickness of 5 nm, instead of using the compound (1-1) of Example 1. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 1

For comparison, an organic EL device was fabricated under the same conditions used in Example 32, except that the second hole transport layer 5 was formed by forming the arylamine compound (4'-2) of the structural formula below having two triphenylamine structures within a molecule in a film thickness of 5 nm, instead of using the compound (1-1) of Example 1, after the first hole transport layer 4 was formed by forming the arylamine compound (4'-2) of the structural formula below having two triphenylamine structures within a molecule in a film thickness of 60 nm. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 232]

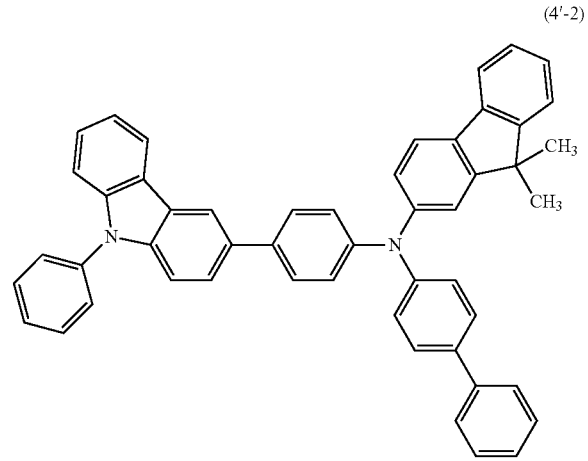

(4'-2)

Comparative Example 2

For comparison, an organic EL device was fabricated under the same conditions used in Example 39, except that the second hole transport layer 5 was formed by forming the arylamine compound (4'-2) of the structural formula having two triphenylamine structures within a molecule in a film thickness of 5 nm, instead of using the compound (1-1) of Example 1, after the first hole transport layer 4 was formed by forming the arylamine compound (4'-2) of the structural formula having two triphenylamine structures within a molecule in a film thickness of 60 nm. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 3

For comparison, an organic EL device was fabricated under the same conditions used in Example 43, except that the second hole transport layer 5 was formed by forming the arylamine compound (4'-2) of the structural formula having two triphenylamine structures within a molecule in a film thickness of 5 nm, instead of using the compound (1-1) of Example 1, after the first hole transport layer 4 was formed by forming the arylamine compound (4'-2) of the structural formula having two triphenylamine structures within a molecule in a film thickness of 60 nm. The characteristics of the organic EL device thus fabricated were measured in the atmosphere at an ordinary temperature. Table 1 summarizes the results of emission characteristics measurements performed by applying a DC voltage to the fabricated organic EL device.

Table 1 summarizes the results of the device lifetime measurements performed with the organic EL devices fabricated in Examples 32 to 46 and Comparative Examples 1 to 3. A device lifetime was measured as the time elapsed until the emission luminance of 2,000 cd/m$^2$ (initial luminance) at the start of emission was attenuated to 1,900 cd/m$^2$ (corresponding to attenuation to 95% when taking the initial luminance as 100%) when carrying out constant current driving.

TABLE 1

| | First hole transport layer | Second hole transport layer | Light emitting layer | Electron Transport layer | Voltage [V] (@10 mA/cm$^2$) | Luminance [cd/m$^2$] (@10 mA/cm$^2$) | Current efficiency [cd/A] (@10 mA/cm$^2$) | Power efficiency [lm/W] (@10 mA/cm$^2$) | Device lifetime (Attenuation to 95%) |
|---|---|---|---|---|---|---|---|---|---|
| Ex. 32 | Compound 4-1 | Compound 1-1 | Compound 2-1/ EMH-1 | Compound 3a-1/ ETM-1 | 4.00 | 829 | 8.28 | 6.51 | 106 h |
| Ex. 33 | Compound 4-1 | Compound 1-11 | Compound 2-1/ EMH-1 | Compound 3a-1/ ETM-1 | 4.04 | 789 | 7.89 | 6.14 | 133 h |
| Ex. 34 | Compound 4-1 | Compound 1-13 | Compound 2-1/ EMH-1 | Compound 3a-1/ ETM-1 | 3.99 | 768 | 7.68 | 6.05 | 118 h |
| Ex. 35 | Compound 4-1 | Compound 1-15 | Compound 2-1/ EMH-1 | Compound 3a-1/ ETM-1 | 4.06 | 790 | 7.89 | 6.12 | 154 h |
| Ex. 36 | Compound 4-1 | Compound 1-17 | Compound 2-1/ EMH-1 | Compound 3a-1/ ETM-1 | 3.91 | 780 | 7.78 | 6.26 | 126 h |
| Ex. 37 | Compound 4-1 | Compound 1-25 | Compound 2-1/ EMH-1 | Compound 3a-1/ ETM-1 | 3.97 | 834 | 8.34 | 6.60 | 122 h |
| Ex. 38 | Compound 4-1 | Compound 1-38 | Compound 2-1/ EMH-1 | Compound 3a-1/ ETM-1 | 3.97 | 816 | 8.15 | 6.44 | 128 h |
| Ex. 39 | Compound 4-1 | Compound 1-1 | Compound 2-9/ EMH-1 | Compound 3a-1/ ETM-1 | 3.99 | 761 | 7.61 | 5.98 | 155 h |
| Ex. 40 | Compound 4-1 | Compound 1-11 | Compound 2-9/ EMH-1 | Compound 3a-1/ ETM-1 | 4.00 | 825 | 8.24 | 6.48 | 138 h |
| Ex. 41 | Compound 4-1 | Compound 1-13 | Compound 2-9/ EMH-1 | Compound 3a-1/ ETM-1 | 3.97 | 816 | 8.15 | 6.44 | 141 h |

TABLE 1-continued

|   | First hole transport layer | Second hole transport layer | Light emitting layer | Electron Transport layer | Voltage [V] (@10 mA/cm²) | Luminance [cd/m²] (@10 mA/cm²) | Current efficiency [cd/A] (@10 mA/cm²) | Power efficiency [lm/W] (@10 mA/cm²) | Device lifetime (Attenuation to 95%) |
|---|---|---|---|---|---|---|---|---|---|
| Ex. 42 | Compound 4-1 | Compound 1-15 | Compound 2-9/ EMH-1 | Compound 3a-1/ ETM-1 | 4.06 | 746 | 7.45 | 5.77 | 121 h |
| Ex. 43 | Compound 4-1 | Compound 1-1 | Compound 2-24/ EMH-1 | Compound 3a-1/ ETM-1 | 3.87 | 804 | 8.03 | 6.52 | 187 h |
| Ex. 44 | Compound 4-1 | Compound 1-11 | Compound 2-24/ EMH-1 | Compound 3a-1/ ETM-1 | 3.89 | 828 | 8.27 | 6.68 | 145 h |
| Ex. 45 | Compound 4-1 | Compound 1-13 | Compound 2-24/ EMH-1 | Compound 3a-1/ ETM-1 | 3.98 | 871 | 8.71 | 6.87 | 135 h |
| Ex. 46 | Compound 4-1 | Compound 1-15 | Compound 2-24/ EMH-1 | Compound 3a-1/ ETM-1 | 3.91 | 848 | 8.47 | 6.81 | 166 h |
| Com. Ex. 1 | Compound 4'-2 | Compound 4'-2 | Compound 2-1/ EMH-1 | Compound 3a-1/ ETM-1 | 3.90 | 680 | 6.80 | 5.48 | 52 h |
| Com. Ex. 2 | Compound 4'-2 | Compound 4'-2 | Compound 2-9/ EMH-1 | Compound 3a-1/ ETM-1 | 3.94 | 685 | 6.85 | 5.46 | 63 h |
| Com. Ex. 3 | Compound 4'-2 | Compound 4'-2 | Compound 2-24/ EMH-1 | Compound 3a-1/ ETM-1 | 3.80 | 780 | 7.08 | 5.85 | 60 h |

As shown in Table 1, the current efficiency upon passing a current with a current density of 10 mA/cm² was 7.45 to 8.71 cd/A for the organic EL devices in Examples 32 to 46, which was higher than 6.80 to 7.08 cd/A for the organic EL devices in Comparative Examples 1 to 3. Further, the power efficiency was 5.77 to 6.87 lm/W for the organic EL devices in Examples 32 to 46, which was higher than 5.46 to 5.85 lm/W for the organic EL devices in Comparative Examples 1 to 3. Table 1 also shows that the device lifetime (attenuation to 95%) was 106 to 187 hours for the organic EL devices in Examples 32 to 46, showing achievement of a far longer lifetime than 52 to 63 hours for the organic EL devices in Comparative Examples 1 to 3.

In the organic EL devices of the present invention, the combination of specific arylamine compounds and specific amine derivatives having a condensed ring structure (and specific compounds having an anthracene ring structure) can improve carrier balance inside the organic EL devices. Further, the organic EL devices of the present invention can achieve high luminous efficiency and a long lifetime, compared to the conventional organic EL devices by combining those compounds in carrier balance matching characteristics of the light-emitting material.

INDUSTRIAL APPLICABILITY

In the organic EL devices of the present invention with the combination of specific arylamine compounds and specific amine derivatives having a condensed ring structure (and specific compounds having an anthracene ring structure), luminous efficiency and durability of an organic EL device can be improved to attain potential applications for, for example, home electric appliances and illuminations.

DESCRIPTION OF REFERENCE NUMERAL

1 Glass substrate
2 Transparent anode
3 Hole injection layer
4 First hole transport layer
5 Second hole transport layer
6 Light emitting layer
7 Electron transport layer
8 Electron injection layer
9 Cathode

The invention claimed is:
1. An organic electroluminescent device comprising at least an anode, a hole transport layer, a light emitting layer, an electron transport layer and a cathode in this order, wherein the hole transport layer comprises an arylamine compound of the following general formula (1), and the light emitting layer comprises an amine derivative of the following general formula (2a-a), (2a-b), (2b-a), (2b-b), (2b-c), (2b-d), (2c-a) or (2c-b) having a condensed ring structure:

[Chemical Formula 1]

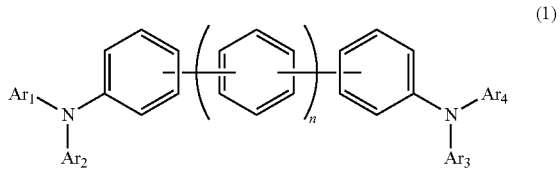

(1)

wherein $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group,
wherein the substituents of the substituted aromatic hydrocarbon groups, substituted aromatic heterocyclic groups, or substituted condensed polycyclic aromatic groups are one or more of a deuterium atom, cyano, nitro, a halogen atom, linear or branched alkyl of 1 to 6 carbon atoms, linear or branched alkyloxy of 1 to 6 carbon atoms, alkenyl, aryloxy, arylalkyloxy, an aromatic hydrocarbon group, a condensed polycyclic aromatic group, an aromatic heterocyclic group, arylvinyl, acyl, or silyl;

and n represents an integer of 2 to 4,

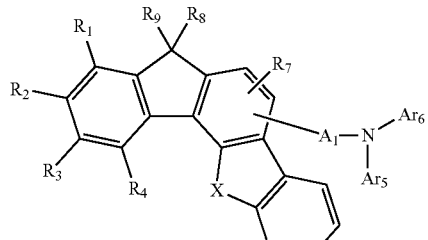
(2a-a)

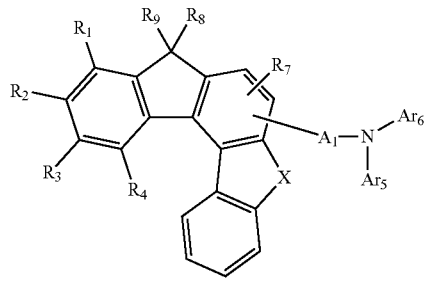
(2a-b)

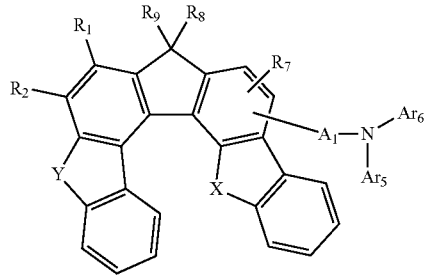
(2b-a)

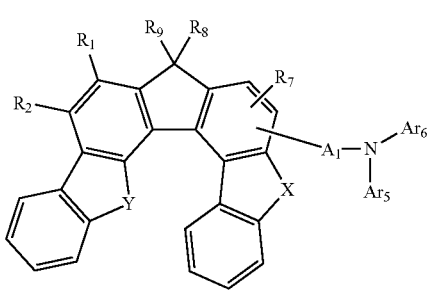
(2b-b)

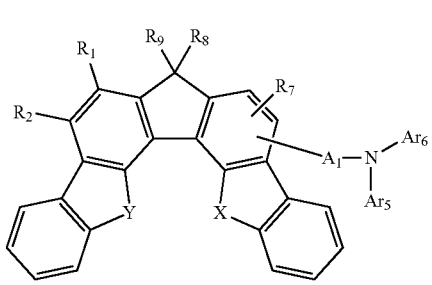
(2b-c)

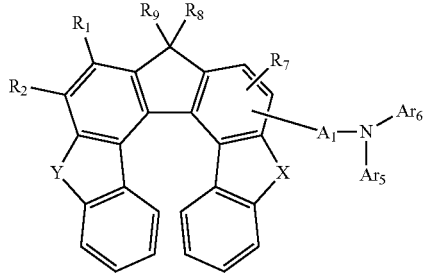
(2b-d)

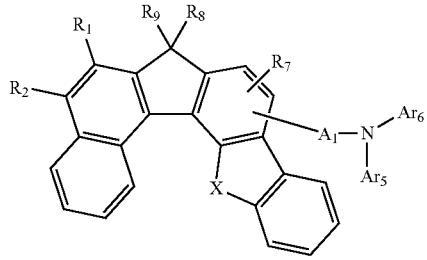
(2c-a)

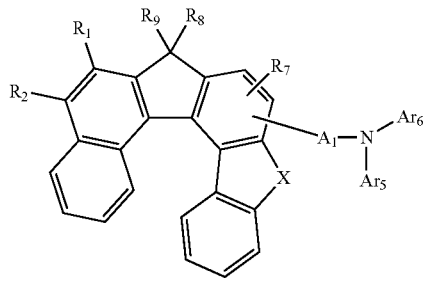
(2c-b)

wherein X and Y may be the same or different, each representing an oxygen atom or a sulfur atom; $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond; $Ar_5$ and $Ar_6$ may be the same or different, and represent a substituted or unsubstituted aromatic hydrocarbon group, a substituted or unsubstituted aromatic heterocyclic group, or a substituted or unsubstituted condensed polycyclic aromatic group, where $Ar_5$ and $Ar_6$ may bind to each other via a single bond, substituted or unsubstituted methylene, an oxygen atom, or a sulfur atom to form a ring; $R_1$ to $R_4$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R_1$ to $R_4$ may bind to each other via a single bond, substituted or unsubstituted methylene, an oxygen atom, or a sulfur atom to form a ring, and $R_1$ to $R_4$ and the benzene ring binding with $R_1$ to $R_4$ may bind to each other via substituted or unsubstituted methylene, an oxygen atom, a sulfur atom, or a mono-substituted amino group; $R_5$ to $R_7$ may be the same or different, represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_5$ to $R_7$ may bind to each other via a single bond, substituted or unsubstituted methylene, an oxygen atom, or a sulfur atom to form a ring, and $R_5$ to $R_7$ and the benzene ring binding with $R_5$ to $R_7$ may bind to each other via substituted or unsubstituted methylene, an oxygen atom, a sulfur atom, or a mono-substituted amino group; and $R_8$ and $R_9$ may be the same or different, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_8$ and $R_9$ may bind to each other via a single bond, substituted or unsubstituted methylene, an oxygen atom, a sulfur atom, or a mono-substituted amino group to form a ring.

2. The organic electroluminescent device according to claim 1, wherein the electron transport layer comprises a compound of the following general formula (3) having an anthracene ring structure,

[Chemical Formula 3]

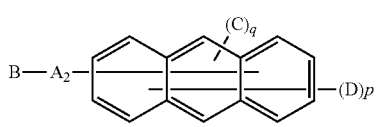

(3)

wherein $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond; B represents a substituted or unsubstituted aromatic heterocyclic group; C represents a substituted or unsubstituted aromatic hydrocarbon group, a substituted or unsubstituted aromatic heterocyclic group, or a substituted or unsubstituted condensed polycyclic aromatic group; D may be the same or different, and represents a hydrogen atom, a deuterium atom, a fluorine atom, a chlorine atom, cyano, trifluoromethyl, linear or branched alkyl of 1 to 6 carbon atoms, a substituted or unsubstituted aromatic hydrocarbon group, a substituted or unsubstituted aromatic heterocyclic group, or a substituted or unsubstituted condensed polycyclic aromatic group; and p represents 7 or 8, and q represents 1 or 2 while maintaining a relationship that a sum of p and q is 9.

3. The organic electroluminescent device according to claim 2, wherein the compound having an anthracene ring structure is a compound of the following general formula (3a) having an anthracene ring structure,

[Chemical Formula 4]

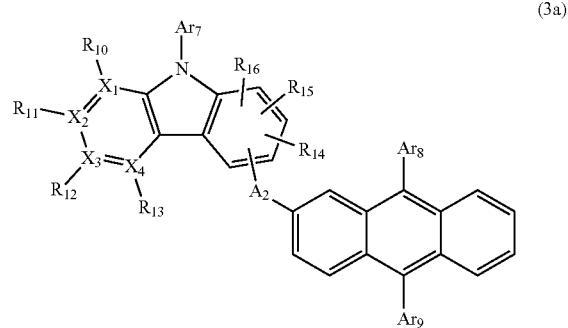

(3a)

wherein $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond; $Ar_7$, $Ar_8$, and $Ar_9$ may be the same or different, and represent a substituted or unsubstituted aromatic hydrocarbon group, a substituted or unsubstituted aromatic heterocyclic group, or a substituted or unsubstituted condensed polycyclic aromatic group; $R_{10}$ to $R_{16}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where $R_{10}$ to $R_{16}$ may bind to each other via a single bond, substituted or unsubstituted methylene, an oxygen atom, or a sulfur atom to form a ring; and $X_1$, $X_2$, $X_3$, and $X_4$ represent a carbon atom or a nitrogen atom, where only one of $X_1$, $X_2$, $X_3$, and $X_4$ is a nitrogen atom, and the nitrogen atom in this case does not have the hydrogen atom or the substituent for $R_{10}$ to $R_{13}$.

4. The organic electroluminescent device according to claim 3, wherein the hole transport layer has a two-layer structure of a first hole transport layer and a second hole transport layer, and the second hole transport layer comprises the arylamine compound of the general formula (1).

5. The organic electroluminescent device according to claim 3, wherein the light emitting layer comprises an anthracene derivative.

6. The organic electroluminescent device according to claim 5, wherein the light emitting layer comprises a host material that is an anthracene derivative.

7. The organic electroluminescent device according to claim 2, wherein the compound having an anthracene ring structure is a compound of the following general formula (3b) having an anthracene ring structure,

[Chemical Formula 5]

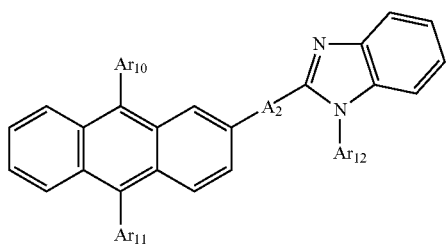

(3b)

wherein $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond; $Ar_{10}$, $Ar_{11}$, and $Ar_{12}$ may be the same or different, and represent a substituted or unsubstituted aromatic hydrocarbon group, a substituted or unsubstituted aromatic heterocyclic group, or a substituted or unsubstituted condensed polycyclic aromatic group.

8. The organic electroluminescent device according to claim 7, wherein the hole transport layer has a two-layer structure of a first hole transport layer and a second hole transport layer, and the second hole transport layer comprises the arylamine compound of the general formula (1).

9. The organic electroluminescent device according to claim 7, wherein the light emitting layer comprises an anthracene derivative.

10. The organic electroluminescent device according to claim 9, wherein the light emitting layer comprises a host material that is an anthracene derivative.

11. The organic electroluminescent device according to claim 2, wherein the compound having an anthracene ring structure is a compound of the following general formula (3c) having an anthracene ring structure,

[Chemical Formula 6]

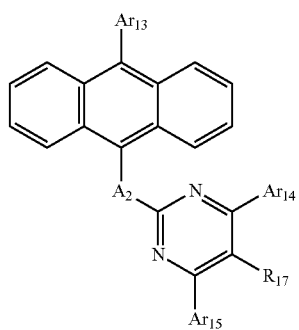

(3c)

wherein $A_2$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond; $Ar_{13}$, $Ar_{14}$, and $Ar_{15}$ may be the same or different, and represent a substituted or unsubstituted aromatic hydrocarbon group, a substituted or unsubstituted aromatic heterocyclic group, or a substituted or unsubstituted condensed polycyclic aromatic group; and $R_{17}$ represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy.

12. The organic electroluminescent device according to claim 11, wherein the hole transport layer has a two-layer structure of a first hole transport layer and a second hole transport layer, and the second hole transport layer comprises the arylamine compound of the general formula (1).

13. The organic electroluminescent device according to claim 11, wherein the light emitting layer comprises an anthracene derivative.

14. The organic electroluminescent device according to claim 2, wherein the hole transport layer has a two-layer structure of a first hole transport layer and a second hole transport layer, and the second hole transport layer comprises the arylamine compound of the general formula (1).

15. The organic electroluminescent device according to claim 2, wherein the light emitting layer comprises an anthracene derivative.

16. The organic electroluminescent device according to claim 15, wherein the light emitting layer comprises a host material that is an anthracene derivative.

17. The organic electroluminescent device according to claim 1, wherein the hole transport layer has a two-layer structure of a first hole transport layer and a second hole transport layer, and the second hole transport layer comprises the arylamine compound of the general formula (1).

18. The organic electroluminescent device according to claim 17, wherein the light emitting layer comprises an anthracene derivative.

19. The organic electroluminescent device according to claim 1, wherein the light emitting layer comprises an anthracene derivative.

20. The organic electroluminescent device according to claim 19, wherein the light emitting layer comprises a host material that is an anthracene derivative.

* * * * *